(12) United States Patent
Kayyem et al.

(10) Patent No.: US 9,891,215 B2
(45) Date of Patent: *Feb. 13, 2018

(54) METHODS FOR THE ELECTROCHEMICAL TREATMENT OF SELF-ASSEMBLED MONOLAYERS

(71) Applicant: GenMark Diagnostics, Inc., Carlsbad, CA (US)

(72) Inventors: Jon Faiz Kayyem, Pasadena, CA (US); Ken Rusterholz, Carlsbad, CA (US); William Bender, Encinitas, CA (US); Sean Ford, Oceanside, CA (US); Claudia C. Argueta, Vista, CA (US)

(73) Assignee: GENMARK DIAGNOSTICS, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/218,615

(22) Filed: Mar. 18, 2014

(65) Prior Publication Data

US 2014/0323326 A1    Oct. 30, 2014

Related U.S. Application Data

(60) Provisional application No. 61/798,260, filed on Mar. 15, 2013.

(51) Int. Cl.
*G01N 33/543* (2006.01)

(52) U.S. Cl.
CPC .................. *G01N 33/5438* (2013.01)

(58) Field of Classification Search
None
See application file for complete search history.

(56) References Cited

U.S. PATENT DOCUMENTS

| | | | |
|---|---|---|---|
| 5,776,672 A * | 7/1998 | Hashimoto | B01L 7/525 435/5 |
| 6,132,955 A * | 10/2000 | Talley et al. | 435/4 |
| 2003/0059929 A1* | 3/2003 | Heller | B01J 19/0046 435/287.2 |
| 2004/0110214 A1* | 6/2004 | Kim | B82Y 30/00 506/16 |
| 2006/0160205 A1 | 7/2006 | Blackburn et al. | |
| 2006/0197960 A1* | 9/2006 | Bazylenko | 356/491 |
| 2007/0207465 A1* | 9/2007 | Kayyem et al. | 435/6 |

OTHER PUBLICATIONS

Elena E. Ferapontova and Kurt V. Gothelf, "Effect of Serum on an RNA Aptamer-Based Electrochemical Sensor for Theophylline," *Langmuir*, 25(8):4279-4283 (2009).

Uhegbu, et al. "Transient data to predict steady-state responses for enzyme-based reactor-sensor systems," *Analytica Chimica Acta*, 281, pp. 549-555 (1993).

* cited by examiner

*Primary Examiner* — Robert T. Crow
(74) *Attorney, Agent, or Firm* — Klarquist Sparkman, LLP

(57) ABSTRACT

The present invention provides compositions and methods directed to an electrode initialization step for the electrochemical treatment of monolayers used in electrochemical detection of target analytes on the surface of a monolayer. Electrode initialization creates a more stable monolayer, and resolves variability within the electrochemical signal detected on the monolayer.

19 Claims, 41 Drawing Sheets

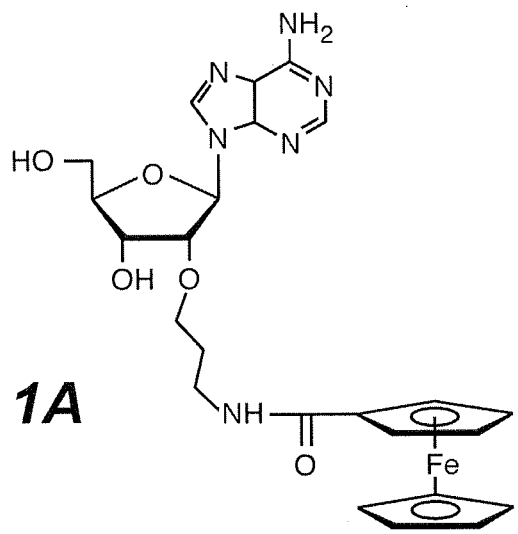
FIG. 1A
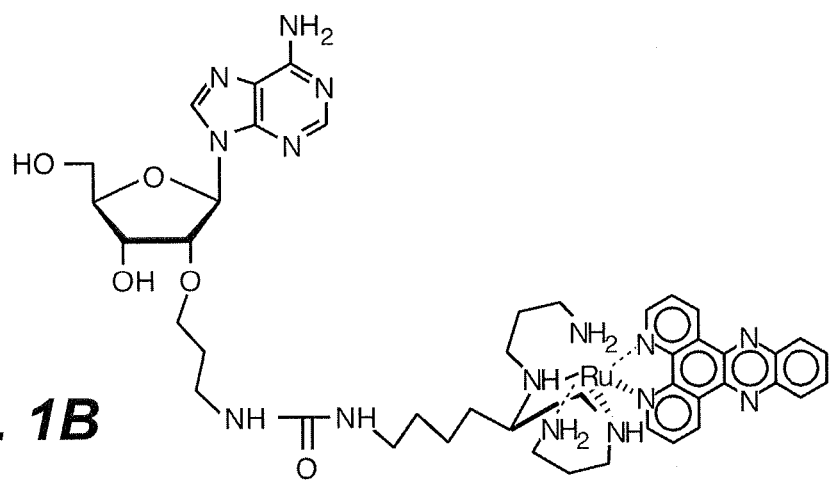
FIG. 1B
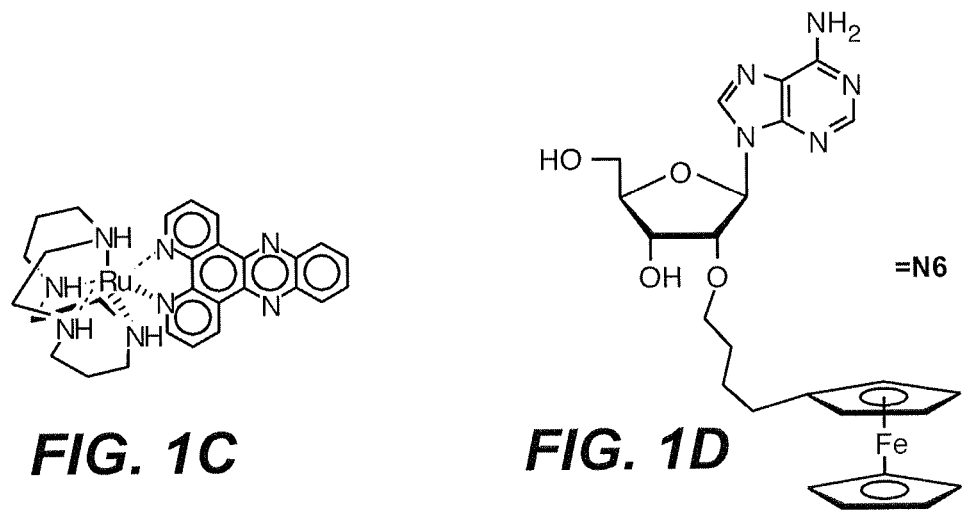
FIG. 1C     FIG. 1D

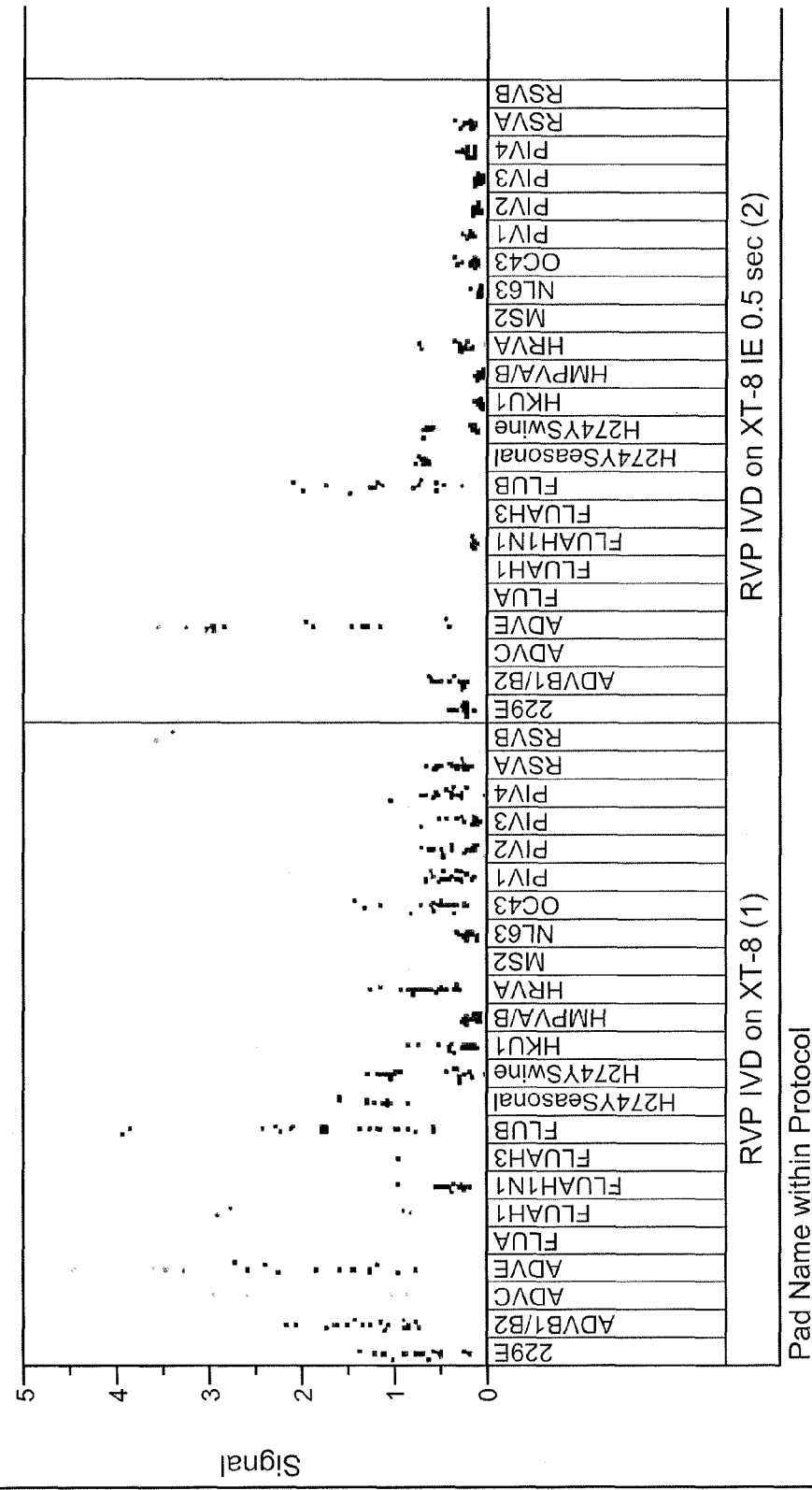

FIG. 13B

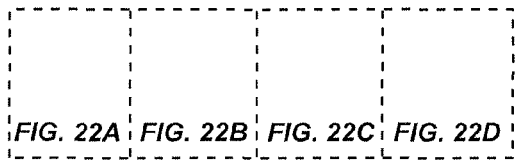
FIG. 22
FIG. 22A
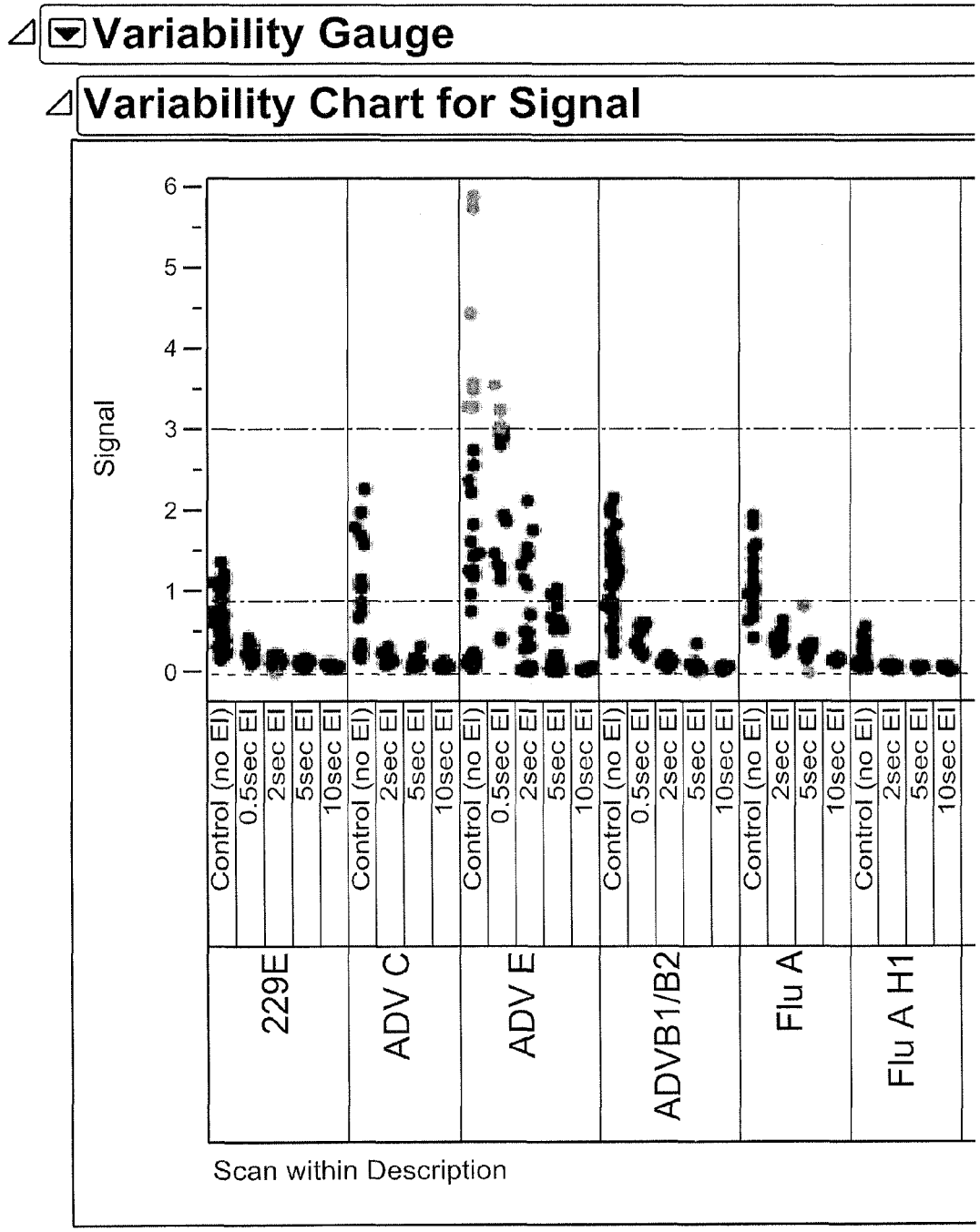

METHODS FOR THE ELECTROCHEMICAL TREATMENT OF SELF-ASSEMBLED MONOLAYERS

CROSS-REFERENCES TO RELATED APPLICATIONS

This patent application claims the benefit of U.S. Provisional Patent Application No. 61/798,260, filed Mar. 15, 2013, the claims of which are specifically incorporated by reference in their entirety.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (e.g. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

The detection of specific nucleic acids is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, *Current Opinion in Biotechnology* 4:48-51 (1993)). The requirement for sensitivity (e.g. low detection limits) has been greatly alleviated by the development of the polymerase chain reaction (PCR) and other amplification technologies which allow researchers to amplify exponentially a specific nucleic acid sequence before analysis as outlined below (for a review, see Abramson et al., *Current Opinion in Biotechnology*, 4:41-47 (1993)).

Sensitivity, e.g. detection limits, remain a significant obstacle in nucleic acid detection systems, and a variety of techniques have been developed to address this issue. Briefly, these techniques can be classified as either target amplification or signal amplification. Target amplification involves the amplification (e.g. replication) of the target sequence to be detected, resulting in a significant increase in the number of target molecules. Target amplification strategies include the polymerase chain reaction (PCR), strand displacement amplification (SDA), and nucleic acid sequence based amplification (NASBA).

Alternatively, rather than amplify the target, alternate techniques use the target as a template to replicate a signaling probe, allowing a small number of target molecules to result in a large number of signaling probes, that then can be detected. Signal amplification strategies include the ligase chain reaction (LCR), cycling probe technology (CPT), and the use of "amplification probes" such as "branched DNA" that result in multiple label probes binding to a single target sequence.

The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference.

Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

Nucleic acid sequence based amplification (NASBA) is generally described in U.S. Pat. No. 5,409,818 and "Profiting from Gene-based Diagnostics," CTB International Publishing Inc., N.J., 1996, both of which are incorporated by reference.

The ligation chain reaction (LCR) involves the ligation of two smaller probes into a single long probe, using the target sequence as the template for the ligase. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, all of which are incorporated by reference.

"Branched DNA" signal amplification relies on the synthesis of branched nucleic acids, containing a multiplicity of nucleic acid "arms" that function to increase the amount of label that can be put onto one probe. This technology is generally described in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

Similarly, dendrimers of nucleic acids serve to vastly increase the amount of label that can be added to a single molecule, using a similar idea but different compositions. This technology is as described in U.S. Pat. No. 5,175,270 and Nilsen et al., *J. Theor. Biol.* 187:273 (1997), both of which are incorporated herein by reference.

Other assays rely on electronic signals for detection. Of particular interest are biosensors. At least two types of biosensors are known; enzyme-based or metabolic biosensors and binding or bioaffinity sensors. See for example U.S. Pat. Nos. 4,713,347; 5,192,507; 4,920,047; 3,873,267; and references disclosed therein, all of which are hereby incorporated by reference. While some of these known sensors use alternating current (AC) techniques, these techniques are generally limited to the detection of differences in bulk (or dielectric) impedance.

There are a variety of nucleic acid biosensors currently known. These include nucleic acid biochips based on fluorescent detection; see for example materials developed by Affymetrix (including, but not limited to, U.S. Pat. Nos. 5,800,992, 5,445,934, 5,744,305, and related patents and materials), Nanogen (including, but not limited to, U.S. Pat. Nos. 5,532,129, 5,605,662, 5,565,322 and 5,632,957 and related patents and materials), Southern (EP 0 373 023 B1) and Synteni/Incyte (WO 95/35505 and related patents and materials). Similarly, electronic detection of nucleic acids using electrodes is also known; see for example U.S. Pat. Nos. 5,591,578; 5,824,473; 5,705,348; 5,780,234, 5,770, 369, 6,063,573, 6,686,150 and 7,090,804; U.S. Ser. Nos. 08/873,598 08/911,589; and WO 98/20162; PCT/US98/12430; PCT/US98/12082; PCT/US99/10104; PCT/US99/01705, and PCT/US99/01703 and related materials, of which hereby are incorporated by reference.

However, further methods are still needed to exploit signal processing advantages in detecting biomolecules such as target analytes. Accordingly, it is an object of the present invention to provide devices and methods for improved signal to noise detection of biomolecules.

BRIEF SUMMARY OF THE INVENTION

In various embodiments, the invention provides a method for detecting the presence of a target analyte in a sample. In an embodiment, the method comprises a) providing an electrode comprising a monolayer and a capture binding ligand; b) initializing the electrode; c) hybridizing a probe to said target analyte to form an assay complex; and d) detecting the presence or absence of said target analyte.

In an embodiment, the detecting provides a better signal to noise ratio than a method wherein no initializing step b) is performed.

In an embodiment, said target analyte is selected from the group consisting of a nucleic acid, a protein, and a combination thereof. In an embodiment, the monolayer is a self-assembled monolayer (SAM). In an embodiment, the SAM comprises insulators. In an embodiment, the SAM comprises conductive oligomers.

In an embodiment, the capture binding ligand further comprises an attachment linker. In an embodiment, the initialization step comprises applying an electronic signal to said electrode.

In an embodiment, said probe is attached to an electron transfer moiety (ETM). In an embodiment, the ETM is responsive to an input waveform. In an embodiment, the ETM is a metallocene. In an embodiment, the metallocene is a ferrocene. In an embodiment, the ferrocene is a ferrocene derivative. In an embodiment, the probe is covalently attached to the ETM.

In an embodiment, the detecting comprises applying an input signal to said electrode. In an embodiment, the input signal generates an output waveform based substantially on electron transfer between said ETM and said electrode.

In an embodiment, the electrode is gold.

In an embodiment, the input signal is AC/DC offset. In an embodiment, the AC frequency ranges from 90-1000 Hz. In an embodiment, the AC voltage ranges from −150 to 880 mV rms. In an embodiment, electrode initialization is performed for 0.5 seconds. In an embodiment, electrode initialization is performed for 1 second. In an embodiment, electrode initialization is performed for 2 seconds. In an embodiment, electrode initialization is performed for 5 seconds. In an embodiment, electrode initialization is performed for 10 seconds. In an embodiment, electrode initialization is performed for longer than 10 seconds.

BRIEF DESCRIPTION OF THE DRAWINGS

FIGS. 1A-1R illustrate a number of different compositions of the invention; the results are shown in Example 1 and 2 of PCT US99/01703, hereby expressly incorporated by reference. FIG. 1A depicts I, also referred to as P290. FIG. 1B depicts II, also referred to as P291. FIG. 1C depicts III, also referred to as W31. FIG. 1D depicts IV, also referred to as N6. FIGS. 1A to 1G and 1J are shown without the phosphoramidite and protecting groups (e.g. DMT) that are readily added. FIGS. 1P-1R show PS32, N6 and W97.

FIG. 2 depicts the use of an electrode 105 with a self-assembled monolayer 15 comprising passivation agents and a capture probe 20 attached via an attachment linker 10. The capture probe 20 has an interrogation position 25 that may comprise a mismatch with the detection position on the target sequence 120. FIG. 2A depicts the target sequence 120 comprising the ETMs 135; FIG. 2B depicts the use of a label probe 40 with the ETMs 135. As will be appreciated by those in the art, amplification probes, label extender probes, etc. can also be used. FIG. 2C utilizes a label probe 40 with the detection position 25. Again, amplification probes, label extender probes, etc. can also be used.

FIG. 3 illustrates different compositions of the invention.

FIG. 13 illustrates noise reduction at different electrode initialization time periods.

FIG. 22 shows that some targets are more affected than others and that different EI times can be used for different electrodes.

DETAILED DESCRIPTION OF THE INVENTION

Overview

Figure 1E:
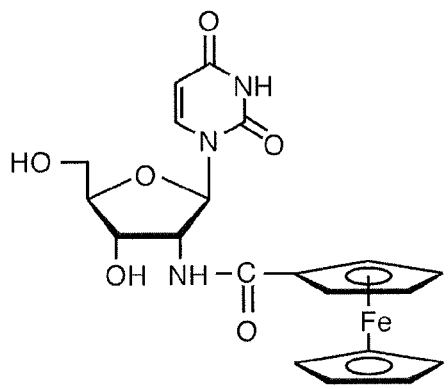
FIG. 1E depicts V, also referred to as P292.
Figure 1F:
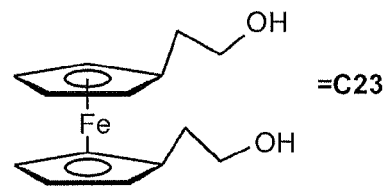
FIG. 1F depicts II, also referred to as C23.
Figure 1G:
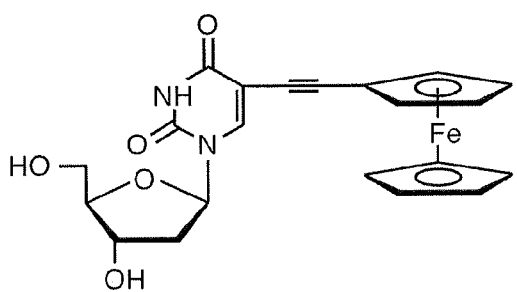
FIG. 1G depicts VII, also referred to as C15.
Figure 1H:
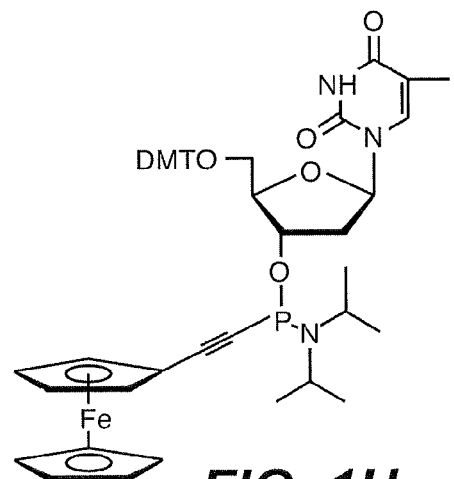
FIG. 1H depicts VIII, also referred to as C95.
Figure 1I:
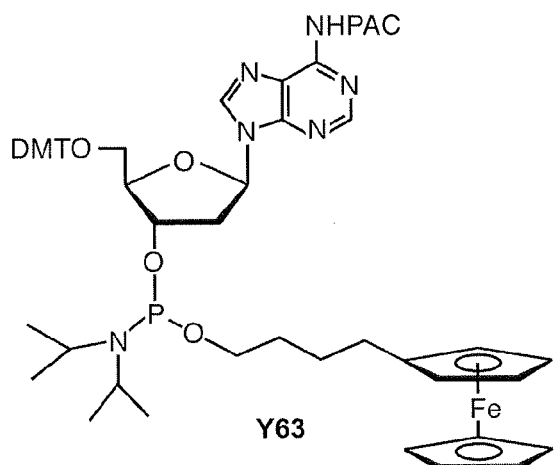
FIG. 1I depicts Y63.
Figure 1J:
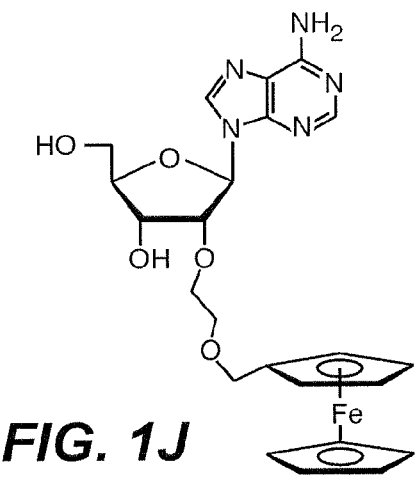
FIG. 1J depicts another compound of the invention.
Figure 1K:
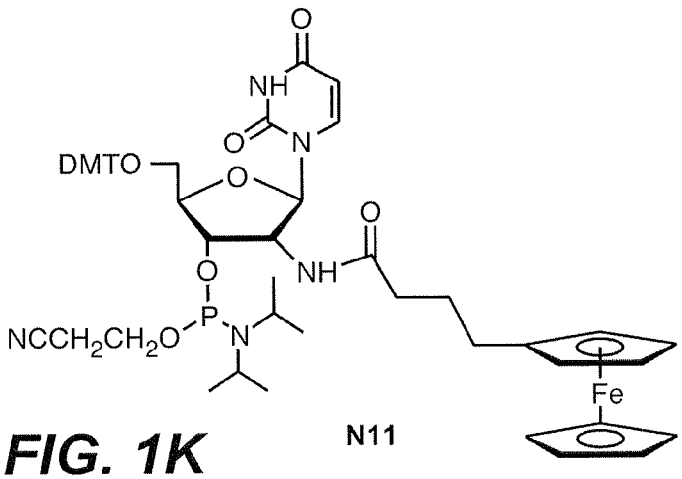
FIG. 1K depicts N11.
Figure 1L:
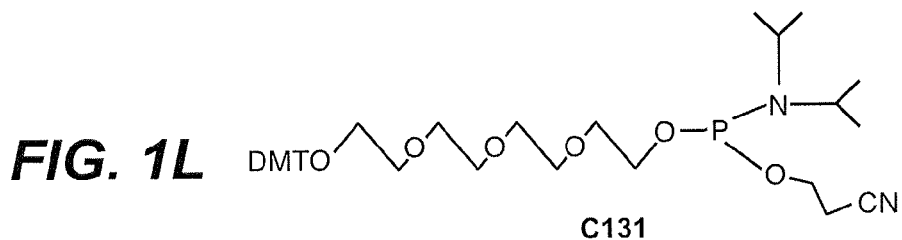
FIG. 1L depicts C131, with a phosphoramidite group and a DMT protecting group.
Figure 1M:
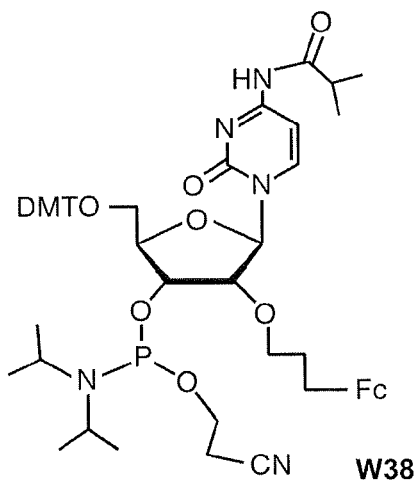
FIG. 1M depicts W38, also with a phosphoramidite group and a DMT protecting group.
Figure 1N:
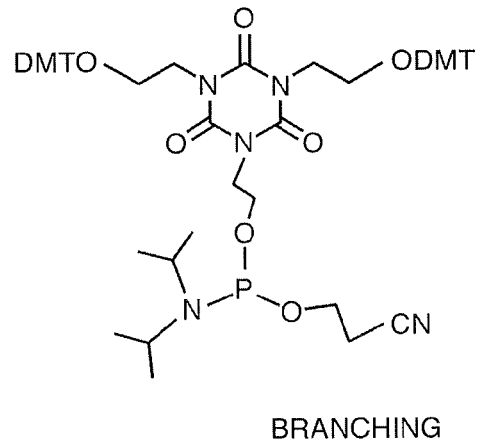
FIG. 1N depicts the commercially available moiety that enables "branching" to occur, as its incorporation into a growing oligonucleotide chain results in addition at both the DMT protected oxygens.
Figure 1O:
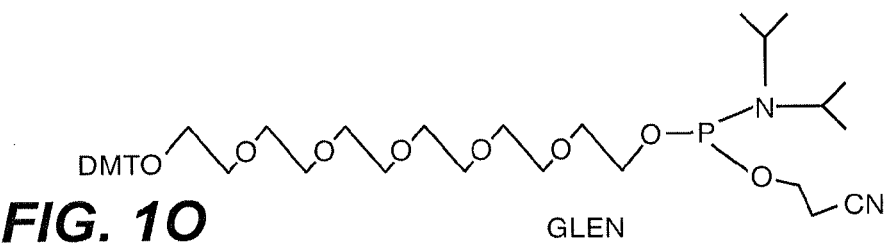
FIG. 1O depicts glen, also with a phosphoramidite group and a DMT protecting group, that serves as a non-nucleic acid linker.
Figure 1P:
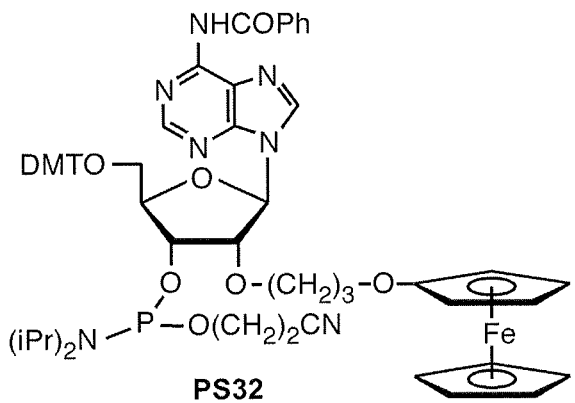
Figure 1Q:
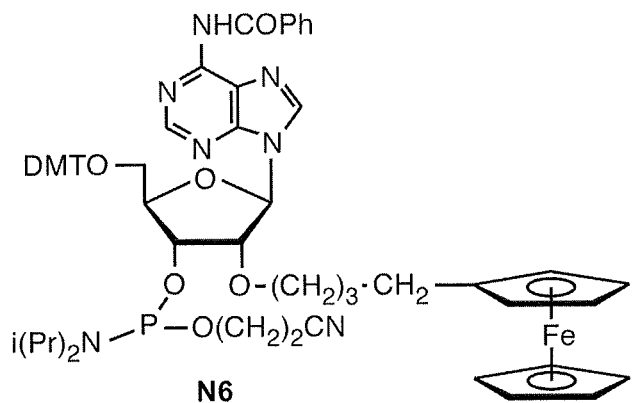
Figure 1R:
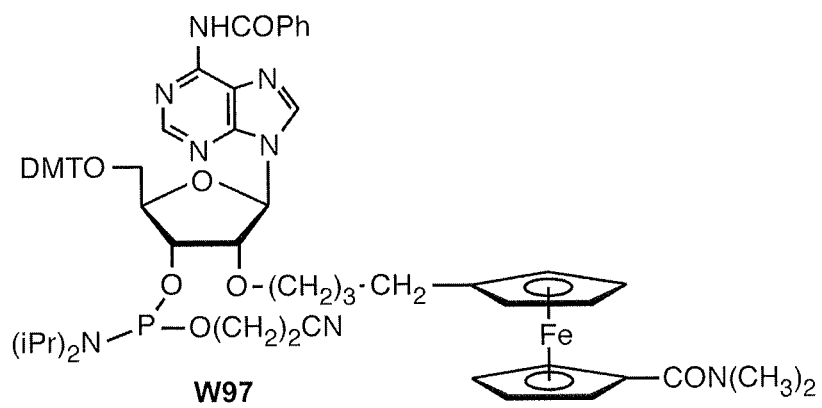

The present invention is directed to the use of signal processing methods for use in the electrochemical detection of target analytes on the surface of a monolayer. In general, in any system, the observed signal is a combination of signal from the target analyte (sample signal) and signal from the background, or noise. The present invention is directed to techniques that provide variations in initiation signals (e.g. varying the "input") that can be used to increase the signal, decrease the noise, or make the signal more obvious or detectable in a background of noise.

Accordingly, the present invention provides compositions and methods directed to an electrode initialization step for the electrochemical treatment of monolayers used in electron transfer detection methods. Electrode initialization creates a more stable monolayer, and resolves variability within the electrochemical signal detected on the monolayer.

In particular, the electrode initialization methods outlined herein provide surprising benefits in three separate ways. First of all, in some cases, due to variations in the reference electrode, the potential at which the electrochemical label oxidizes, usually ferrocene and ferrocene derivatives as outlined herein, is shifted as a result of the these variations in the reference electrode. This can result in a poor fit of the signal trace by the assay software, and can lead in some cases to miscalls of sequence. Secondly, due to the presence of non-specific labels which can settle near the electrode, the score is shifted closer to an indeterminate boundary of the assay's calling parameters. The score in this case (seen in the figures) is the ratio of the wild-type signal to the mismatch signal (WT:MT). This can result in a "no call", or in extreme cases, a miscall. Finally, if a sample is poorly processed, a signal can be generated which barely exceeds signal threshold, but is incorrectly fit due to the shape of the signal trace. As above, this can result in a "no call", or in extreme cases, a miscall. All three of these issues have been successfully and surprisingly addressed by the present invention.

Furthermore, due to the fact that the individual working electrodes in the systems of the invention are independently addressable, each "pad" or electrode can be initialized separately, depending on the capture ligands, probes, etc. That is, the affinity of different label probes within a multiplex assay to different electrodes with different capture probes may be different, as shown in the Figures. Thus, the ability to initialize different electrodes with different capture probes leads to increased signal to noise ratios.

In general, any assay that relies on electrochemical detection will benefit from the present invention. The present invention finds particular use in systems generally described in U.S. Pat. Nos. 5,591,578, 5,824,473, 5,770,369, 5,705,348 5,780,234, 6,686,150 and 7,090,804, 7,935,481, and PCT application WO98/20162, all of which are expressly incorporated herein by reference in their entirety. These systems rely on the use of capture binding ligands (called capture probes when the target analyte is a nucleic acid) to anchor target analytes to the electrode surface and form an assay complex. The assay complex further comprises an electron transfer moiety (ETM) that is directly or indirectly attached to the target analyte. That is, the presence of the ETM near the electrode surface is dependent on the presence of the target analyte. Electron transfer between the ETM and the electrode is initiated using a variety of techniques as outlined below, and the output signals received and optionally processed as further outlined below. Thus, by detecting electron transfer, the presence or absence of the target analyte is determined.

Samples

The compositions and methods provided herein are related to the detection of the presence of a target analyte in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (e.g. in the case of nucleic acids, the sample may be the products of an amplification reaction, including both target and signal amplification as is generally described in PCT/US99/01705, such as PCR amplification reaction); purified samples, such as purified genomic DNA, RNA, proteins, etc.; raw samples (bacteria, virus, genomic DNA, etc.; As will be appreciated by those in the art, virtually any experimental manipulation may have been done on the sample.

The compositions and methods are directed to the detection of target analytes. By "target analytes" or grammatical equivalents herein is meant any molecule or compound to be detected. As outlined below, target analytes preferably bind to binding ligands, as is more fully described below. As will be appreciated by those in the art, a large number of analytes may be detected using the present methods; basically, any target analyte for which a binding ligand, described below, may be made may be detected using the methods of the invention.

Suitable analytes include organic and inorganic molecules, including biomolecules. In an embodiment, the analyte may be an environmental pollutant (including pesticides, insecticides, toxins, etc.); a chemical (including solvents, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eucaryotic cells, including mammalian tumor cells); viruses (including retroviruses, herpesviruses, adenoviruses, lentiviruses, etc.); and spores; etc. Analytes can be environmental pollutants; nucleic acids; proteins (including enzymes, antibodies, antigens, growth factors, cytokines, etc); therapeutic and abused drugs; cells; and viruses.

Target analytes can include proteins and nucleic acids. "Protein" as used herein includes proteins, polypeptides, and peptides. The protein may be made up of naturally occurring amino acids and peptide bonds, or synthetic peptidomimetic structures. The side chains may be in either the (R) or the (S) configuration. In an embodiment, the amino acids are in the (S) or L-configuration. If non-naturally occurring side chains are used, non-amino acid substituents may be used, for example to prevent or retard in vivo degradations.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppressants, abused drugs (amphetamine, methamphetamine, cannabinoids, cocaine and opiates) and antibodies to any number of viruses (including orthomyxoviruses, (e.g. influenza virus), paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus*; *Vibrio*, e.g. *V. cholerae*; *Escherichia*, e.g. Enterotoxigenic *E. coli*, *Shigella*, e.g. *S. dysenteriae*; *Salmonella*, e.g. *S. typhi*; *Mycobacterium* e.g. *M. tuberculosis*, *M. leprae*; *Clostridium*, e.g. *C. botulinum*, *C. tetani*, *C. difficile*, *C. perfringens*; *Cornyebacterium*, e.g. *C. diphtheriae*; *Streptococcus*, *S. pyogenes*, *S. pneumoniae*; *Staphylococcus*, e.g. *S. aureus*; *Haemophilus*, e.g. *H. influenzae*; *Neisseria*, e.g. *N. meningitidis*, *N. gonorrhoeae*; *Yersinia*, e.g. *G. lamblia Y. pestis*, *Pseudomonas*, e.g. *P. aeruginosa*, *P. putida*; *Chlamydia*, e.g. *C. trachomatis*; *Bordetella*, e.g. *B. pertussis*; *Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α. and TGF-βhuman growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone and testosterone; and (4) other proteins (including α-fetoprotein, carcinoembryonic antigen CEA, cancer markers, etc.).

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), prostate cancer (PSA), CEA, and colorectal and pancreatic cancer (CA 19, CA 50, CA242).

Suitable target analytes include metal ions, particularly heavy and/or toxic metals, including but not limited to, aluminum, arsenic, cadmium, selenium, cobalt, copper, chromium, lead, silver and nickel.

Target analytes can be nucleic acids. In an embodiment, the target analyte is a nucleic acid, and target sequences are detected. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, e.g. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, a first target domain of the sample target sequence may hybridize to a capture probe or a portion of capture extender probe, a second target domain may hybridize to a portion of an amplifier probe, a label probe, or a different capture or capture extender probe, etc. The target domains may be adjacent or separated. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and U.S. Pat. No. 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of ETMs, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of an ETM attachment, or an analog structure may be used. Alternatively, mixtures of different nucleic acid analogs, and mixtures of naturally occurring nucleic acids and analogs may be made.

An embodiment includes peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. An embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The target analyte can be amplified when the target is a nucleic acid. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), and nucleic acid sequence based amplification (NASBA).

Electrodes

The compositions and methods of the present invention comprise electrodes. By "electrode" herein is meant a composition, which, when connected to an electronic device, is able to sense a current or charge and convert it to a signal. Alternatively an electrode can be defined as a composition which can apply a potential to and/or pass electrons to or from species in the solution. Thus, an electrode can be an ETM as described herein. Electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($MO_2O_6$), tungsten oxide ($WO_3$) and ruthenium oxides; and carbon (including glassy carbon electrodes, graphite and carbon paste). Electrodes include gold, silicon, platinum, carbon and metal oxide electrodes.

The conformation of the electrode will vary with the detection method used. For example, flat planar electrodes can be used for optical detection methods, or when arrays of nucleic acids are made, thus requiring addressable locations for both synthesis and detection. Alternatively, for single probe analysis, the electrode may be in the form of a tube, with SAMs comprising capture binding ligands to the inner surface. Electrode coils can be used in some embodiments as well. This allows a maximum of surface area containing the target analytes to be exposed to a small volume of sample.

In an embodiment, the detection electrodes are formed on a substrate. In addition, the discussion herein is generally directed to the formation of gold electrodes, but as will be appreciated by those in the art, other electrodes can be used as well. The substrate can comprise a wide variety of materials, as will be appreciated by those in the art, such as printed circuit board (PCB) materials. Thus, in general, the suitable substrates include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), GETEK (a blend of polypropylene oxide and fiberglass), etc. In some embodiments, glass may not be preferred as a substrate.

In general, materials can include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

The present system finds particular utility in array formats, e.g. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture ligands to many thousands can be made. Generally, the array will comprise from two to as many as 100,000 or more, depending on the size of the electrodes, as well as the end use of the array. Ranges can be from about 2 to about 10,000, from about 5 to about 1000, and from about 10 to about 100. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

Accordingly, in an embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In an embodiment, one of the monolayer-forming species comprises a capture ligand as outlined herein. In addition, each electrode has an interconnection that is attached to the electrode at one end and is ultimately attached to a device that can control the electrode sometimes through multiplexed devices, (e.g. MUX). That is, each electrode is independently addressable.

The substrates can be part of a larger device comprising a detection chamber that exposes a given volume of sample to the detection electrode. Generally, the detection chamber ranges from about 1 nL to 1 ml, with about 10 µL to 500 µL being preferred. As will be appreciated by those in the art, depending on the experimental conditions and assay, smaller or larger volumes may be used.

In some embodiments, the detection chamber and electrode are part of a cartridge that can be placed into a device comprising electronic components (an AC/DC voltage source, an ammeter, a processor, a read-out display, temperature controller, light source, etc.). In this embodiment, the interconnections from each electrode are positioned such that upon insertion of the cartridge into the device, connections between the electrodes and the electronic components are established. In some embodiments, the connections from the electrodes are made by passing through the substrate to produce a so called land grid array that can interface to a pogo pin or like connector to make connections from the chip to the instrument. In this embodiment, pogo pin connectors are used in place of edge card connectors. In this embodiment, rather than contain longer interconnects, the electrode array is one surface of the substrate, such as a PCR board or ceramic substrate, and there are "through board" or "through substrate" interconnects ending in pads. When the cartridge is placed in the device, these pads contact "pogo pin" type connectors, thus saving space on the chip and allowing for higher density arrays, if desired. In some embodiments, switching circuitry (multiplexers) can be built into the pogo pin connector. These embodiments are described in US publication 2011/0180425, herein incorporated by reference in its entirety.

Detection electrodes on circuit board material (or other substrates) are generally prepared in a wide variety of ways. In general, high purity gold is used, and it may be deposited on a surface via vacuum deposition processes (sputtering and evaporation) or solution deposition (electroplating or electroless processes). When electroplating is done, the substrate must initially comprise a conductive material; fiberglass circuit boards are frequently provided with copper foil. Frequently, depending on the substrate, an adhesion layer between the substrate and the gold in order to insure good mechanical stability is used. Thus, embodiments utilize a deposition layer of an adhesion metal such as chromium, titanium, titanium/tungsten, tantalum, nickel or palladium, which can be deposited as above for the gold. When electroplated metal (either the adhesion metal or the electrode metal) is used, grain refining additives, frequently referred to in the trade as brighteners, can optionally be added to alter surface deposition properties. Brighteners are mixtures of organic and inorganic species, with cobalt and nickel being preferred.

In general, the adhesion layer is from about 100 Å thick to about 25 microns (1000 microinches). If the adhesion metal is electrochemically active, the electrode metal must be coated at a thickness that prevents "bleed-through"; if the adhesion metal is not electrochemically active, the electrode metal may be thinner. Generally, the electrode metal (preferably gold) is deposited at thicknesses ranging from about 500 Å to about 5 microns (200 microinches), with from about 30 microinches to about 50 microinches being preferred. In general, the gold is deposited to make electrodes ranging in size from about 5 microns to about 5 mm in diameter, with about 100 to 250 microns being preferred. The detection electrodes thus formed are then preferably cleaned and SAMs added, as is discussed below.

Thus, the present invention provides methods of making a substrate comprising a plurality of gold electrodes. The methods first comprise coating an adhesion metal, such as nickel or palladium (optionally with brightener), onto the substrate. Electroplating is preferred. The electrode metal, preferably gold, is then coated (again, with electroplating preferred) onto the adhesion metal. Then the patterns of the device, comprising the electrodes and their associated interconnections are made using lithographic techniques, particularly photolithographic techniques as are known in the art, and wet chemical etching. Frequently, a non-conductive chemically resistive insulating material such as solder mask or plastic is laid down using these photolithographic techniques, leaving only the electrodes and a connection point to the leads exposed; the leads themselves are generally coated.

Monolayers

In addition to electronic components, the electrodes of the invention comprise monolayers, which can include self-assembled monolayers (SAMs). This basic mechanism is described in U.S. Pat. Nos. 5,591,578, 5,770,369, 5,705,348, and PCT US97/20014. Briefly, previous work has shown that electron transfer can proceed rapidly through the stacked n-orbitals of double stranded nucleic acid, and significantly more slowly through single-stranded nucleic acid. Accordingly, this can serve as the basis of an assay.

Thus, by adding ETMs (either covalently to one of the strands or non-covalently to the hybridization complex through the use of hybridization indicators, described below) to a nucleic acid that is attached to a detection electrode, electron transfer between the ETM and the electrode, through the nucleic acid, may be detected.

Alternatively, the ETM can be detected, not necessarily via electron transfer through nucleic acid, but rather can be directly detected on an electrode comprising a SAM; that is, the electrons from the ETMs need not travel through the stacked π orbitals in order to generate a signal. As above, in this embodiment, the detection electrode preferably comprises a self-assembled monolayer (SAM) that serves to shield the electrode from redox-active species in the sample.

Thus, in either embodiment, as is more fully outlined below, an assay complex is formed that contains an ETM, which is then detected using the detection electrode.

Thus, in an embodiment, the electrode comprises a monolayer. As outlined herein, the efficiency of target analyte binding (for example, oligonucleotide hybridization) may increase when the analyte is at a distance from the electrode. Similarly, non-specific binding of biomolecules, including the target analytes, to an electrode is generally reduced when a monolayer is present. Thus, a monolayer facilitates the maintenance of the analyte away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accessibility to the electrode.

By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. A majority of the molecules include a functional group that adheres to the surface, and a portion that interacts with neighboring molecules in the monolayer to form the relatively ordered array. A "mixed" monolayer comprises a heterogeneous monolayer, that is, where at least two different molecules make up the monolayer.

In some embodiments, the monolayer comprises conductive oligomers. By "conductive oligomer" herein is meant a substantially conducting oligomer, preferably linear, some embodiments of which are referred to in the literature as "molecular wires." By "substantially conducting" herein is meant that the oligomer is capable of transferring electrons at 100 Hz. Generally, the conductive oligomer has substantially overlapping n-orbitals, e.g. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons. A variety of conductive oligomers are described in U.S. Pat. No. 6,740,518, hereby incorporated by reference in their entirety.

In an embodiment, the monolayer may comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferably slower than the rate through the conductive oligomers described herein.

It will be appreciated that the monolayer may comprise different insulatory species, although preferably the different species are chosen such that a reasonably uniform SAM can be formed. Thus, for example, when nucleic acids are covalently attached to the electrode using insulators, it is possible to have one type of insulator used to attach the nucleic acid, and another type functioning to detect the ETM. Similarly, the use of different insulators may be done to facilitate monolayer formation, or to make monolayers with altered properties. In one embodiment, it is possible to use mixtures of insulators with different types of terminal groups, e.g. polyethylene glycol. Thus, for example, some of the terminal groups may facilitate detection, and some may prevent non-specific binding.

In an embodiment, the insulators have a conductivity, S, of about $10^{-7}$ $\Omega^{-1}$ $cm^{-1}$ or lower, with less than about $10^{-8}$ $\Omega^{-1}$ $cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, e.g. nitrogen, oxygen, sulfur, phosphorus, silicon or boron included in the chain.

Suitable insulators are known in the art, and include, but are not limited to, $-(CH_2)_n-$, $-(CRH)_n-$, and $-(CR_2)_n-$, ethylene glycol or derivatives using other heteroatoms in place of oxygen, e.g. nitrogen or sulfur (sulfur derivatives are not preferred when the electrode is gold).

The insulators may be substituted with R groups as defined herein to alter the packing of the moieties on an electrode, the hydrophilicity or hydrophobicity of the insulator, and the flexibility, e.g. the rotational, torsional or longitudinal flexibility of the insulator. For example, branched alkyl groups may be used. Similarly, the insulators may contain terminal groups, as outlined above, particularly to influence the surface of the monolayer.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups may be different, e.g. a heterooligomer. That is, an oligomer may comprise an oligomer of a single type of Y groups, or of multiple types of Y groups.

The aromatic group may be substituted with a substitution group, generally depicted herein as R. R groups may be added as necessary to affect the packing of the insulator, e.g. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In an embodiment, when the insulator is greater than three subunits, R groups are preferred to increase solubility when solution synthesis is done. However, the R groups, and their positions, are chosen to minimally affect the packing of the insulator on a surface, particularly within a monolayer, as described below. In general, only small R groups are used within the monolayer, with larger R groups generally above the surface of the monolayer. Thus for example the attachment of methyl groups to the portion of the insulator within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with an embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —$NH_2$, —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Ethers can include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Substituted alkyls can partially or fully halogenated alkyls such as $CF_3$, etc.

By "aldehyde" herein is meant —RCHO groups.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —$(O-CH_2-CH_2)_n$— group, although each carbon atom of the ethylene group may also be singly or doubly substituted, e.g. —$(O-CR_2-CR_2)_n$—, with R as described above. Ethylene glycol derivatives with other heteroatoms in place of oxygen (e.g. —$(N-CH_2-CH_2)_n$— or —$(S-CH_2-CH_2)_n$—, or with substitution groups) are also preferred.

Substitution groups can include, but are not limited to, methyl, ethyl, propyl, alkoxy groups such as —O—$(CH_2)_2CH_3$ and —O—$(CH_2)_4CH_3$ and ethylene glycol and derivatives thereof.

Aromatic groups can include, but are not limited to, phenyl, naphthyl, naphthalene, anthracene, phenanthroline, pyrole, pyridine, thiophene, porphyrins, and substituted derivatives of each of these, included fused ring derivatives.

In an embodiment, the insulator species included in the SAM utilizes novel methods and compositions comprising asymmetric disulfides. As outlined herein, the signals generated from label probes can be dependent on the behavior or properties of the SAM. SAMs comprising "nanoconduits" or "electroconduits," as outlined in U.S. Ser. No. 60/145,912 hereby expressly incorporated herein by reference in its entirety, give good signals. Thus, the present invention provides asymmetric insulators based on disulfides, wherein one of the arms being a longer alkyl chain (or other SAM forming species) and the other arm comprising either a shorter alkyl chain or a bulky group, such as a branched alkyl group, that can be polar or nonpolar) for creating the nanoconduits. Exemplary species and methods of making are described in U.S. Ser. No. 09/847,113. See also Mukaiyama Tetrahedron Lett. 1968, 5907; Boustany Tetrahedron Lett. 1970 3547; Harpp Tetrahedron Lett. 1970 3551; and Oae, J. Chem. Soc. Chem. Commun, 1977, 407, all of which are expressly incorporated herein by reference.

The length of the species making up the monolayer will vary as needed. As outlined above, it appears that hybridization is more efficient at a distance from the surface. The species to which nucleic acids are attached can be basically the same length as the monolayer forming species or longer than them, resulting in the nucleic acids being more accessible to the solvent for hybridization.

As will be appreciated by those in the art, the actual combinations and ratios of the different species making up the monolayer can vary widely. Two component systems utilize a first species comprising a capture probe containing species, attached to the electrode via either an insulator. The second species are insulators. In this embodiment, the first species can comprise from about 90% to about 1%, with from about 20% to about 40% being preferred. For nucleic acids, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. To achieve these approximate proportions, preferred ratios of first:second: third species in SAM formation solvents are 2:2:1 for short targets, 1:3:1 for longer targets, with total thiol concentration (when used to attach these species, as is more fully outlined below) in the 500 μM to 1 mM range, and 833 μM being preferred.

Alternatively, two component systems can be used. In one embodiment, the two components are the first and second species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred. Alternatively, the two components are the first and the third species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred.

In an embodiment, the deposition of the SAM is done using aqueous solvents. As is generally described in Steel et al., *Anal. Chem.* 70:4670 (1998), Herne et al., J. Am. Chem. Soc. 119:8916 (1997), and Finklea, Electrochemistry of Organized Monolayers of Thiols and Related Molecules on Electrodes, from A. J. Bard, *Electroanalytical Chemistry: A Series of Advances*, Vol. 20, Dekker N.Y. 1966-, all of which are expressly incorporated by reference, the deposition of the SAM-forming species can be done out of aqueous solutions, frequently comprising salt.

The covalent attachment of the insulators may be accomplished in a variety of ways, depending on the electrode and the composition of the insulators used. In an embodiment, the attachment linkers with covalently attached nucleosides or nucleic acids as depicted herein are covalently attached to an electrode. Thus, one end or terminus of the attachment linker is attached to the nucleoside or nucleic acid, and the other is attached to an electrode. In some embodiments it may be desirable to have the attachment linker attached at a position other than a terminus, or even to have a branched attachment linker that is attached to an electrode at one terminus and to two or more nucleosides at other termini, although this is not preferred. Similarly, the attachment linker may be attached at two sites to the electrode, as is generally depicted in Structures 2-4. Generally, some type of linker is used, as depicted below as "A" in Structure 1, where "X" is A a conductive oligomer, "I" is an insulator and the hatched surface is the electrode:

Structure 1

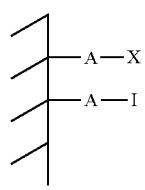

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., *Langmuir* 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., *Langmuir* 10:1306-1313 (1994)). Thus, A moieties include, but are not limited to, silane moieties, sulfur moieties (including alkyl sulfur moieties), and amino moieties. In an embodiment, epoxide type linkages with redox polymers such as are known in the art are not used.

Although depicted herein as a single moiety, insulators may be attached to the electrode with more than one "A" moiety; the "A" moieties may be the same or different. Thus, for example, when the electrode is a gold electrode, and "A" is a sulfur atom or moiety, multiple sulfur atoms may be used to attach an insulator to the electrode, such as is generally depicted below in Structures 2, 3 and 4. As will be appreciated by those in the art, other such structures can be made. In Structures 2, 3 and 4, the A moiety is just a sulfur atom, but substituted sulfur moieties may also be used.

Many of the structures herein depict conductive oligomers as the attachment linkers, or provide an option as a conductive oligomer or insulator (e.g. "X or I"), but insulators such as alkyl chains are preferred in many embodiments.

Structure 2

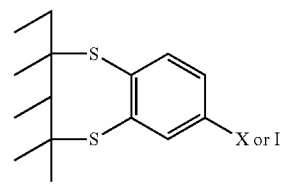

Structure 3

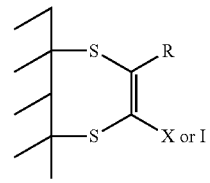

Structure 4

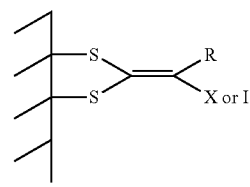

It should also be noted that similar to Structure 4, it may be possible to have an insulator terminating in a single carbon atom with three sulfur moieties attached to the electrode. Additionally, although not always depicted herein, the insulators may also comprise a "Q" terminal group.

In an embodiment, the electrode is a gold electrode, and attachment is via a sulfur linkage as is well known in the art, e.g. the A moiety is a sulfur atom or moiety. Although the exact characteristics of the gold-sulfur attachment are not known, this linkage is considered covalent for the purposes of this invention. A representative structure is depicted in Structure 5. Similarly, any of the insulators may also comprise terminal groups as described herein. Structure 5 depicts the "A" linker as comprising just a sulfur atom, although additional atoms may be present (e.g. substitution groups). In addition, Structure 5 shows the sulfur atom attached to the Y aromatic group, but as will be appreciated by those in the art, it may be attached to the B-D group (e.g. an acetylene) as well.

Structure 5

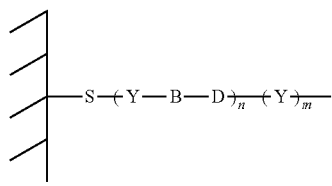

In an embodiment, the electrode is a carbon electrode, e.g. a glassy carbon electrode, and attachment is via a nitrogen of an amine group. A representative structure is depicted in Structure 6. Again, additional atoms may be present, e.g. Z type linkers and/or terminal groups.

Structure 6

Structure 7

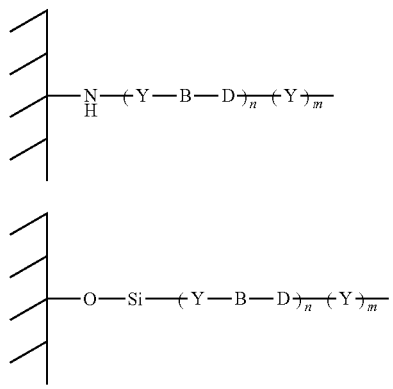

In Structure 7, the oxygen atom is from the oxide of the metal oxide electrode. The Si atom may be combined with other atoms, e.g. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

The SAMs of the invention can be made in a variety of ways, including deposition out of organic solutions and deposition out of aqueous solutions. The methods outlined herein use a gold electrode as the example, although as will be appreciated by those in the art, other metals and methods may be used as well. In one embodiment, indium-tin-oxide (ITO) is used as the electrode.

In an embodiment, a gold surface is first cleaned. A variety of cleaning procedures may be employed, including, but not limited to, chemical cleaning or etchants including Piranha solution (hydrogen peroxide/sulfuric acid) or aqua regia (hydrochloric acid/nitric acid), electrochemical methods, flame treatment, plasma treatment or combinations thereof.

Following cleaning, the gold substrate is exposed to the SAM species. When the electrode is ITO, the SAM species are phosphonate-containing species. This can also be done in a variety of ways, including, but not limited to, solution deposition, gas phase deposition, microcontact printing, spray deposition, deposition using neat components, etc. An embodiment utilizes a deposition solution comprising a mixture of various SAM species in solution, generally thiol-containing species. Mixed monolayers that contain nucleic acids are usually prepared using a two step procedure. The thiolated nucleic acid is deposited during the first deposition step (generally in the presence of at least one other monolayer-forming species) and the mixed monolayer formation is completed during the second step in which a second thiol solution minus nucleic acid is added. Optionally, a second step utilizing mild heating to promote monolayer reorganization.

In an embodiment, the deposition solution is an organic deposition solution. In this embodiment, a clean gold surface is placed into a clean vial. A binding ligand deposition solution in organic solvent is prepared in which the total thiol concentration is between micromolar to saturation; preferred ranges include from about 1 µM to 10 mM, with from about 400 uM to about 1.0 mM being especially preferred. In an embodiment, the deposition solution contains thiol modified DNA (e.g. nucleic acid attached to an attachment linker) and thiol diluent molecules. The ratio of nucleic acid to diluent (if present) is usually between 1000:1 to 1:1000, with from about 10:1 to about 1:10 being preferred and 1:1 being especially preferred. Solvents can be tetrahydrofuran (THF), acetonitrile, dimethylforamide (DMF), ethanol, or mixtures thereof; generally any solvent of sufficient polarity to dissolve the capture ligand can be used, as long as the solvent is devoid of functional groups that will react with the surface. Sufficient nucleic acid deposition solution is added to the vial so as to completely cover the electrode surface. The gold substrate is allowed to incubate at ambient temperature or slightly above ambient temperature for a period of time ranging from seconds to hours, with 5-30 minutes being preferred. After the initial incubation, the deposition solution is removed and a solution of diluent molecule only (from about 1 µM to 10 mM, with from about 100 uM to about 1.0 mM being preferred) in organic solvent is added. The gold substrate is allowed to incubate at room temperature or above room temperature for a period of time (seconds to days, with from about 10 minutes to about 24 hours being preferred). The gold sample is removed from the solution, rinsed in clean solvent and used.

In an embodiment, an aqueous deposition solution is used. As above, a clean gold surface is placed into a clean vial. A nucleic acid deposition solution in water is prepared in which the total thiol concentration is between about 1 uM and 10 mM, with from about 1 µM to about 200 uM being preferred. The aqueous solution frequently has salt present (up to saturation, with approximately 1M being preferred), however pure water can be used. The deposition solution contains thiol modified nucleic acid and often a thiol diluent molecule. The ratio of nucleic acid to diluent is usually between 1000:1 to 1:1000, with from about 10:1 to about 1:10 being preferred and 1:1 being especially preferred. The nucleic acid deposition solution is added to the vial in such a volume so as to completely cover the electrode surface. The gold substrate is allowed to incubate at ambient temperature or slightly above ambient temperature for 1-30 minutes with 5 minutes usually being sufficient. After the initial incubation, the deposition solution is removed and a solution of diluent molecule only (10 uM-1.0 mM) in either water or organic solvent is added. The gold substrate is allowed to incubate at room temperature or above room temperature until a complete monolayer is formed (10 minutes-24 hours). The gold sample is removed from the solution, rinsed in clean solvent and used.

In an embodiment, the deposition solution comprises a zwitterionic compound, preferably betaine. Preferred embodiments utilize betaine and Tris-HCl buffers.

In an embodiment, as outlined herein, a circuit board is used as the substrate for the gold electrodes. Formation of the SAMs on the gold surface is generally done by first cleaning the boards, for example in a 10% sulfuric acid solution for 30 seconds, detergent solutions, aqua regia, plasma, etc., as outlined herein. Following the sulfuric acid treatment, the boards are washed, for example via immersion in two Milli-Q water baths for 1 minute each. The boards are then dried, for example under a stream of nitrogen. Spotting of the deposition solution onto the boards is done using any number of known spotting systems, generally by placing the boards on an X-Y table, preferably in a humidity chamber. The size of the spotting drop will vary with the size of the electrodes on the boards and the equipment used for delivery of the solution; for example, for 250 μM size electrodes, a 30 nanoliter drop is used. The volume should be sufficient to cover the electrode surface completely. The drop is incubated at room temperature for a period of time (sec to overnight, with 5 minutes preferred) and then the drop is removed by rinsing in a Milli-Q water bath. The boards are then optionally treated with a second deposition solution, generally comprising insulator in organic solvent, preferably acetonitrile, by immersion in a 45° C. bath. After 30 minutes, the boards are removed and immersed in an acetonitrile bath for 30 seconds followed by a milli-Q water bath for 30 seconds. The boards are dried under a stream of nitrogen. Preferably, only the water rinse is employed.

Capture Binding Ligands

In an embodiment, the detection electrode comprising the SAM further comprises capture binding ligands, preferably covalently attached. By "binding ligand" or "binding species" herein is meant a compound that is used to probe for the presence of the target analyte that will bind to the target analyte. In general, for most of the embodiments described herein, there are at least two binding ligands used per target analyte molecule; a "capture" or "anchor" binding ligand (also referred to herein as a "capture probe", particularly in reference to a nucleic acid binding ligand) that is attached to the detection electrode as described herein, and a soluble binding ligand (frequently referred to herein as a "signaling probe" or a "label probe"), that binds independently to the target analyte, and either directly or indirectly comprises at least one ETM. However, it should be noted that for some nucleic acid detection systems, the target sequence is generally amplified, and during amplification, a label is added; thus these systems generally comprise only two elements, the capture probe and the labeled target. The discussion below is directed to the use of electrodes and electrochemical detection, but as will be appreciated by those in the art, fluorescent based systems can be used as well.

Generally, the capture binding ligand allows the attachment of a target analyte to the detection electrode, for the purposes of detection. As is more fully outlined below, attachment of the target analyte to the capture binding ligand may be direct (e.g. the target analyte binds to the capture binding ligand) or indirect (one or more capture extender ligands may be used).

In an embodiment, the binding is specific, and the binding ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding that is not highly specific; for example, the systems may use different binding ligands, for example an array of different ligands, and detection of any particular analyte is via its "signature" of binding to a panel of binding ligands, similar to the manner in which "electronic noses" work. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about $10^{-4}$ to $10^{-9}$ $M^{-1}$, with at least about $10^{-5}$ to $10^{-9}$ being preferred and at least about $10^{-7}$ to $10^{-9}$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins (particularly including antibodies or fragments thereof (FAbs, etc.)), small molecules, or aptamers, described above. Binding ligands can include proteins include peptides. For example, when the analyte is an enzyme, suitable binding ligands include substrates, inhibitors, and other proteins that bind the enzyme, e.g. components of a multienzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences. In an embodiment, the binding ligands are portions (particularly the extracellular portions) of cell surface receptors that are known to multimerize, such as the growth hormone receptor, glucose transporters (particularly GLUT4 receptor), transferrin receptor, epidermal growth factor receptor, low density lipoprotein receptor, high density lipoprotein receptor, leptin receptor, interleukin receptors including IL-1, IL-2, IL-3, IL-4, IL-5, IL-6, IL-7, IL-8, IL-9, IL-11, IL-12, IL-13, IL-15 and IL-17 receptors, VEGF receptor, PDGF receptor, EPO receptor, TPO receptor, ciliary neurotrophic factor receptor, prolactin receptor, and T-cell receptors. Similarly, there is a wide body of literature relating to the development of binding partners based on combinatorial chemistry methods.

In this embodiment, when the binding ligand is a nucleic acid, compositions and techniques are outlined in U.S. Pat. Nos. 5,591,578; 5,824,473; 5,705,348; 5,780,234 and 5,770, 369; U.S. Ser. Nos. 08/873,598 08/911,589; WO 98/20162; WO98/12430; WO98/57158; WO 00/16089) WO99/57317; WO99/67425; WO00/24941; PCT US00/10903; WO00/38836; WO99/37819; WO99/57319 and PCTUS00/20476; and related materials, all of which are expressly incorporated by reference in their entirety.

The method of attachment of the capture binding ligands to the attachment linker will generally be done as is known in the art, and will depend on both the composition of the attachment linker and the capture binding ligand. In general, the capture binding ligands are attached to the attachment linker through the use of functional groups on each that can then be used for attachment. Functional groups for attachment can be amino groups, carboxy groups, oxo groups and thiol groups. These functional groups can then be attached, either directly or indirectly through the use of a linker, sometimes depicted herein as "Z". Linkers are well known in the art; for example, homo- or hetero-bifunctional linkers as are well known (see 1994 Pierce Chemical Company catalog, technical section on cross-linkers, pages 155-200, incorporated herein by reference). Z linkers can include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages.

In this way, capture binding ligands comprising proteins, lectins, nucleic acids, small organic molecules, carbohydrates, etc. can be added.

An embodiment utilizes proteinaceous capture binding ligands. As is known in the art, any number of techniques may be used to attach a proteinaceous capture binding ligand to an attachment linker. A wide variety of techniques are known to add moieties to proteins.

An embodiment utilizes nucleic acids as the capture binding ligand. While most of the following discussion focuses on nucleic acids, as will be appreciated by those in the art, many of the techniques outlined below apply in a similar manner to non-nucleic acid systems as well, and to systems that rely on attachment to surfaces other than metal electrodes.

The capture probe nucleic acid is covalently attached to the electrode, via an "attachment linker", that can be an insulator. By "covalently attached" herein is meant that two moieties are attached by at least one bond, including sigma bonds, pi bonds and coordination bonds.

Thus, one end of the attachment linker is attached to a nucleic acid (or other binding ligand), and the other end (although as will be appreciated by those in the art, it need not be the exact terminus for either) is attached to the electrode. Thus, any of the structures depicted herein may further comprise a nucleic acid effectively as a terminal group. Thus, the present invention provides compositions comprising nucleic acids covalently attached to electrodes as is generally depicted below in Structure 8:

Structure 8

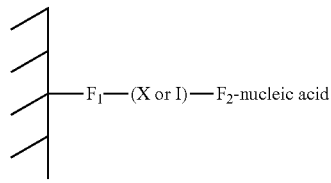

$F_1$—(X or I)—$F_2$-nucleic acid

In Structure 8, the hatched marks on the left represent an electrode. X is a conductive oligomer and I is an insulator as defined herein. $F_1$ is a linkage that allows the covalent attachment of the electrode and the insulator, including bonds, atoms or linkers such as is described herein, for example as "A", defined below. $F_2$ is a linkage that allows the covalent attachment of the insulator to the nucleic acid, and may be a bond, an atom or a linkage as is herein described. $F_2$ may be part of the insulator, part of the nucleic acid, or exogeneous to both, for example, as defined herein for "Z".

In an embodiment, the capture probe nucleic acid is covalently attached to the electrode via an attachment linker. The covalent attachment of the nucleic acid and the attachment linker may be accomplished in several ways. In an embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occurring nucleic acids, although as will be appreciated by those in the art, similar techniques may be used with nucleic acid analogs, and in some cases with other binding ligands. Similarly, most of the structures herein depict conductive oligomers as the attachment linkers, but insulators such as alkyl chains are preferred in many embodiments.

In an embodiment, the attachment linker is attached to the base of a nucleoside of the nucleic acid. This may be done in several ways, depending on the linker, as is described below. In one embodiment, the linker is attached to a terminal nucleoside, e.g. either the 3' or 5' nucleoside of the nucleic acid. Alternatively, the linker is attached to an internal nucleoside.

The point of attachment to the base will vary with the base. Generally, attachment at any position is possible. In some embodiments, for example when the probe containing the ETMs may be used for hybridization, it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In an embodiment, the attachment linker is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4): 714 (1977); Verheyden et al., J. Org. Chem. 36(2):250 (1971); McGee et al., J. Org. Chem. 61:781-785 (1996); Mikhailopulo et al., Liebigs. Ann. Chem. 513-519 (1993); McGee et al., Nucleosides & Nucleotides 14(6):1329 (1995), all of which are incorporated by reference). These modified nucleosides are then used to add the attachment linkers.

An embodiment utilizes amino-modified nucleosides. These amino-modified riboses can then be used to form either amide or amine linkages to an insulator. In an embodiment, the amino group is attached directly to the ribose, although as will be appreciated by those in the art, short linkers such as those described herein for "Z" may be present between the amino group and the ribose.

Thus the present invention provides substrates comprising at least one detection electrode comprising monolayers and capture binding ligands, useful in target analyte detection systems.

Electron Transfer Moieties

The terms "electron donor moiety", "electron acceptor moiety", and "ETMs" (ETMs) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. ETMs can include, but are not limited to, transition metal complexes, organic ETMs, and electrodes.

In an embodiment, the ETMs are transition metal complexes. Transition metals are those whose atoms have a partial or complete d shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinum, cobalt and iron.

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the insulator, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the insulator and the ligand attached to the nucleic acid are at least bidentate; that is, r is preferably zero, one (e.g. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetraazacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In an embodiment, organometallic ligands are used. In addition to purely organic compounds for use as redox moieties, and various transition metal coordination complexes with σ-bonded organic ligand with donor atoms as heterocyclic or exocyclic substituents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion [$C_5H_5(-1)$] and various ring substituted and ring fused derivatives, such as the indenylide (−1) ion, that yield a class of bis(cyclopentadieyl) metal compounds, (e.g. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene [$(C_5H_5)_2Fe$] and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(−1) ion, or butadiene yield potentially suitable organometallic compounds, and all such ligands, in conjunction with other π-bonded and σ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In an embodiment, only one of the two metallocene ligands of a metallocene are derivatized.

Again, other attachment linkers such as alkyl groups may also be utilized.

In an embodiment, the ligands used in the invention show altered fluorescent properties depending on the redox state of the chelated metal ion. As described below, this thus serves as an additional mode of detection of electron transfer between the ETM and the electrode.

In addition, similar methods can be used to attach proteins to the detection electrode; see for example U.S. Pat. No. 5,620,850, hereby incorporated by reference.

In an embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other ligands can include cyclopentadiene and phenanthroline.

In an embodiment, the capture probe nucleic acids (or other binding ligands) are covalently attached to the electrode via an insulator (e.g. the attachment linker is an insulator). The attachment of nucleic acids (and other binding ligands) to insulators such as alkyl groups is well known, and can be done to the base or the backbone, including the ribose or phosphate for backbones containing these moieties, or to alternate backbones for nucleic acid analogs.

In an embodiment, there may be one or more different capture probe species on the surface. In some embodiments, there may be one type of capture probe, or one type of capture probe extender, as is more fully described below. Alternatively, different capture probes, or one capture probe with a multiplicity of different capture extender probes can be used. Similarly, it may be desirable to use auxiliary capture probes that comprise relatively short probe sequences, that can be used to "tack down" components of the system, for example the recruitment linkers, to increase the concentration of ETMs at the surface.

In an embodiment, a number of capture probes are designed and used for each target sequence. That is, a single electrode pad of the array may have 1 probe to the target analyte, or a plurality of probes to the same target sequence, preferably (but not required to be) non-overlapping. This is particularly preferred for long target sequences. In this embodiment, at least two different capture probes are used, with at least 3, 4, 5, 6, 7, 8, 9 or 10 being preferred, and 8 being particularly preferred.

Generally, where a biochip is used for measurements of protein and nucleic acid biomarkers, the protein biomarkers are measured on a chip separate from that used to measure the nucleic acid biomarkers. For nonlimiting examples of additional platforms and methods useful for measuring nucleic acids, see Publications US 2006/0275782 and US2005/0064469. In various embodiments, biomarkers are measured on the same platform, such as on one chip. In various embodiments, biomarkers are measured using different platforms and/or different experimental runs.

In an embodiment, the compositions further comprise a solution or soluble binding ligand. Solution binding ligands are similar to capture binding ligands, in that they bind, preferably specifically, to target analytes. The solution binding ligand (generally referred to herein as label probes when the target analytes are nucleic acids) may be the same or different from the capture binding ligand. Generally, the solution binding ligands are not directly attached to the surface. The solution binding ligand either directly comprises a recruitment linker that comprises at least one ETM (FIG. 4A from 60/190,259), or the recruitment linker binds, either directly or indirectly, to the solution binding ligand.

Thus, "solution binding ligands" or "soluble binding ligands" or "signal carriers" or "label probes" or "label binding ligands" with recruitment linkers comprising covalently attached ETMs are provided. That is, one portion of the label probe or solution binding ligand directly or indirectly binds to the target analyte, and one portion comprises a recruitment linker comprising covalently attached ETMs. In some systems, these may be the same. Similarly, the recruitment linker comprises nucleic acid that will hybridize to detection probes.

Figure 2A:
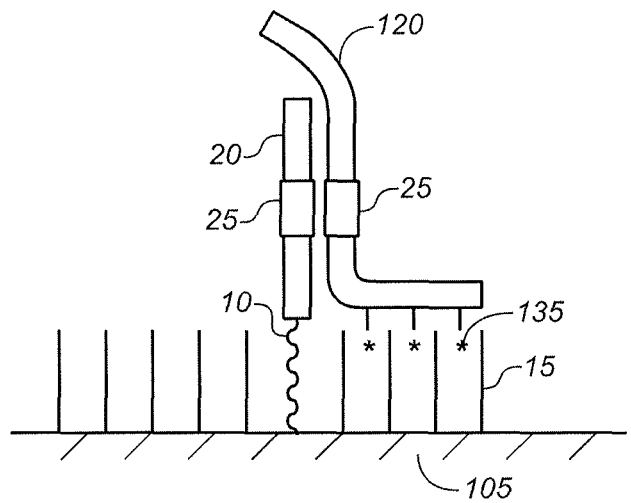
FIGS. 2A-2C illustrate several embodiments for mismatch detection.
Figure 2B:
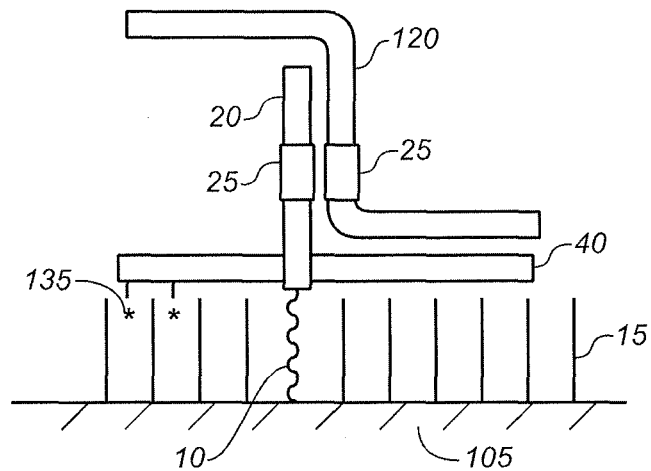
Figure 2C:
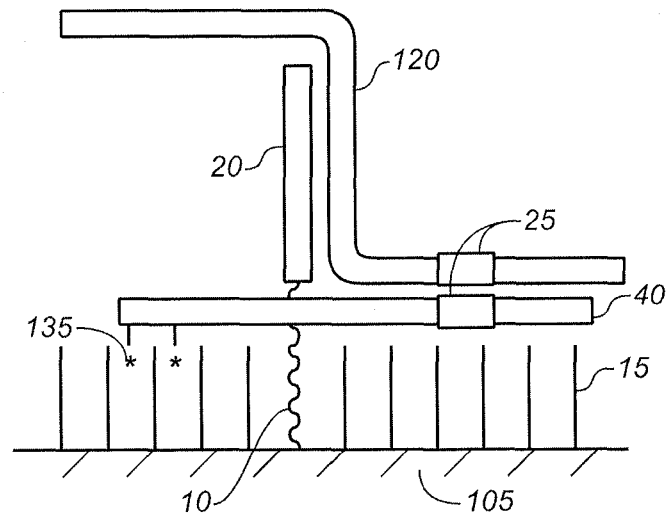
Figure 3A:
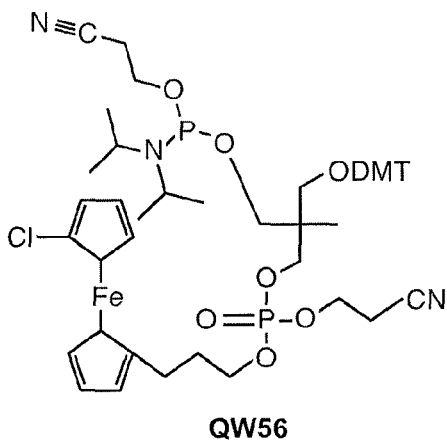
FIG. 3A depicts QW56 and FIG. 3B depicts QW80.
Figure 3B:
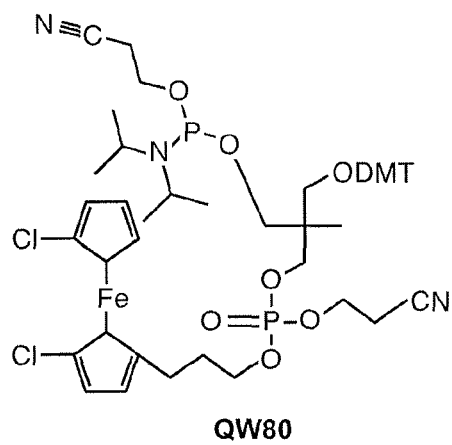

Preferred ETMs comprise metallocenes, particularly ferrocene or ferrocene derivatives (FIG. 1). Preferred ferrocene derivatives can be N6 (FIG. 1D), QW56 (FIG. 2A), and QW80 (FIG. 2B).

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2,1,9-def:6,5,10-d'e'f')diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetraene, naphthalene, acenaphthalene, perylene, TMPD and analogs and substituted derivatives of these compounds.

In one embodiment, the electron donors and acceptors are redox proteins as are known in the art. However, redox proteins in many embodiments are not preferred.

The choice of the specific ETMs will be influenced by the type of electron transfer detection used, as is generally outlined below. ETMs can include are metallocenes, with ferrocene or ferrocene derivatives being particularly preferred.

Without being bound by theory, in some embodiments, electron transfer is facilitated when the ETM is able to penetrate ("snuggle") into the monolayer to some degree. That is, in general, it appears that hydrophobic ETMs used with hydrophobic SAMs give rise to better (greater) signals than ETMs that are charged or more hydrophilic. Thus, for example, ferrocene in solution can penetrate the monolayers of the examples and give a signal when electroconduits are present, while ferrocyanide in solution gives little or no signal. Thus, in general, hydrophobic ETMs are preferred in some embodiments; however, transition metal complexes, although charged, with one or more hydrophobic ligands, such as Ru and Os complexes, also give rise to good signals. Similarly, electron transfer between the ETM and the electrode is facilitated by the use of linkers or spacers that allow the ETM some flexibility to penetrate into the monolayer; thus the N6 compositions of the invention have a four carbon linker attaching the ETM to the nucleic acid.

In an embodiment, a plurality of ETMs is used. The use of multiple ETMs provides signal amplification and thus allows more sensitive detection limits. As discussed below, while the use of multiple ETMs on nucleic acids that hybridize to complementary strands can cause decreases in $T_m$s of the hybridization complexes depending on the number, site of attachment and spacing between the multiple ETMs, this is not a factor when the ETMs are on the recruitment linker, since this does not hybridize to a complementary sequence. Accordingly, pluralities of ETMs are preferred, with at least about 2 ETMs per recruitment linker being preferred, and at least about 10 being particularly preferred, and at least about 20 to 50 being especially preferred. In some instances, very large numbers of ETMs (100 to 1000) can be used.

As will be appreciated by those in the art, the portion of the label probe (or target, in some embodiments) that comprises the ETMs (termed herein a "recruitment linker" or "signal carrier") can be nucleic acid, or it can be a non-nucleic acid linker that links the first hybridizable portion of the label probe to the ETMs. That is, since this portion of the label probe is not required for hybridization, it need not be nucleic acid, although this may be done for ease of synthesis. In some embodiments, as is more fully outlined below, the recruitment linker may comprise double-stranded portions. Thus, as will be appreciated by those in the art, there are a variety of configurations that can be used. In an embodiment, the recruitment linker is nucleic acid (including analogs), and attachment of the ETMs can be via (1) a base; (2) the backbone, including the ribose, the phosphate, or comparable structures in nucleic acid analogs; (3) nucleoside replacement, described below; or (4) metallocene polymers, as described below. In an embodiment, the recruitment linker is non-nucleic acid, and can be either a metallocene polymer or an alkyl-type polymer (including heteroalkyl, as is more fully described below) containing ETM substitution groups.

In an embodiment, the recruitment linker is a nucleic acid, and comprises covalently attached ETMs. The ETMs may be attached to nucleosides within the nucleic acid in a variety of positions. Embodiments can include, but are not limited to, (1) attachment to the base of the nucleoside, (2) attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers, with the latter being preferred.

Figure 16:
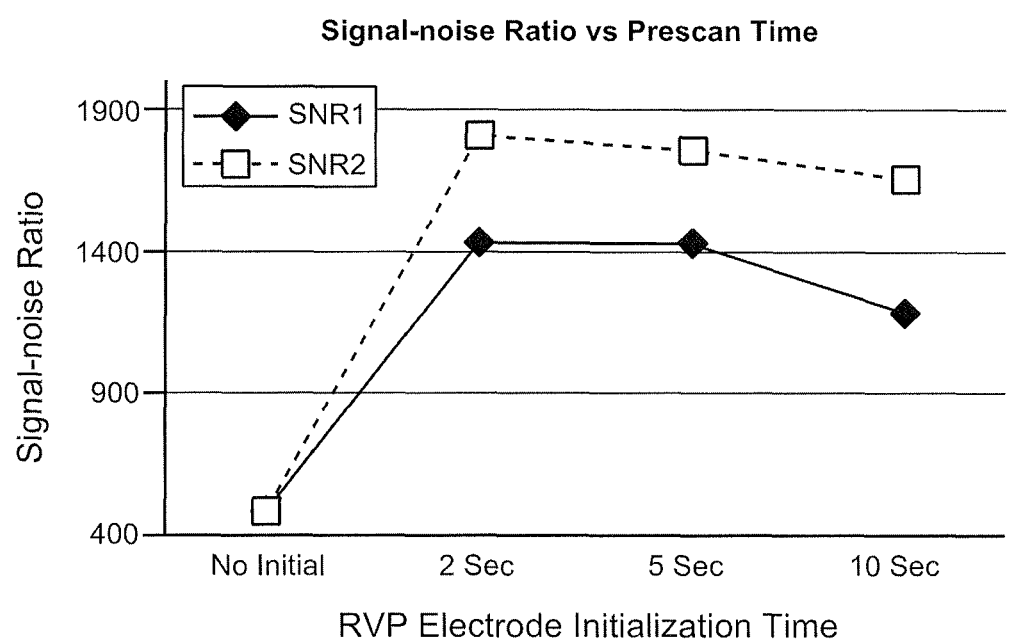
FIG. 16 illustrates increased signal-noise ratios at 2 and 5 second electrode initialization periods.
Figure 17:
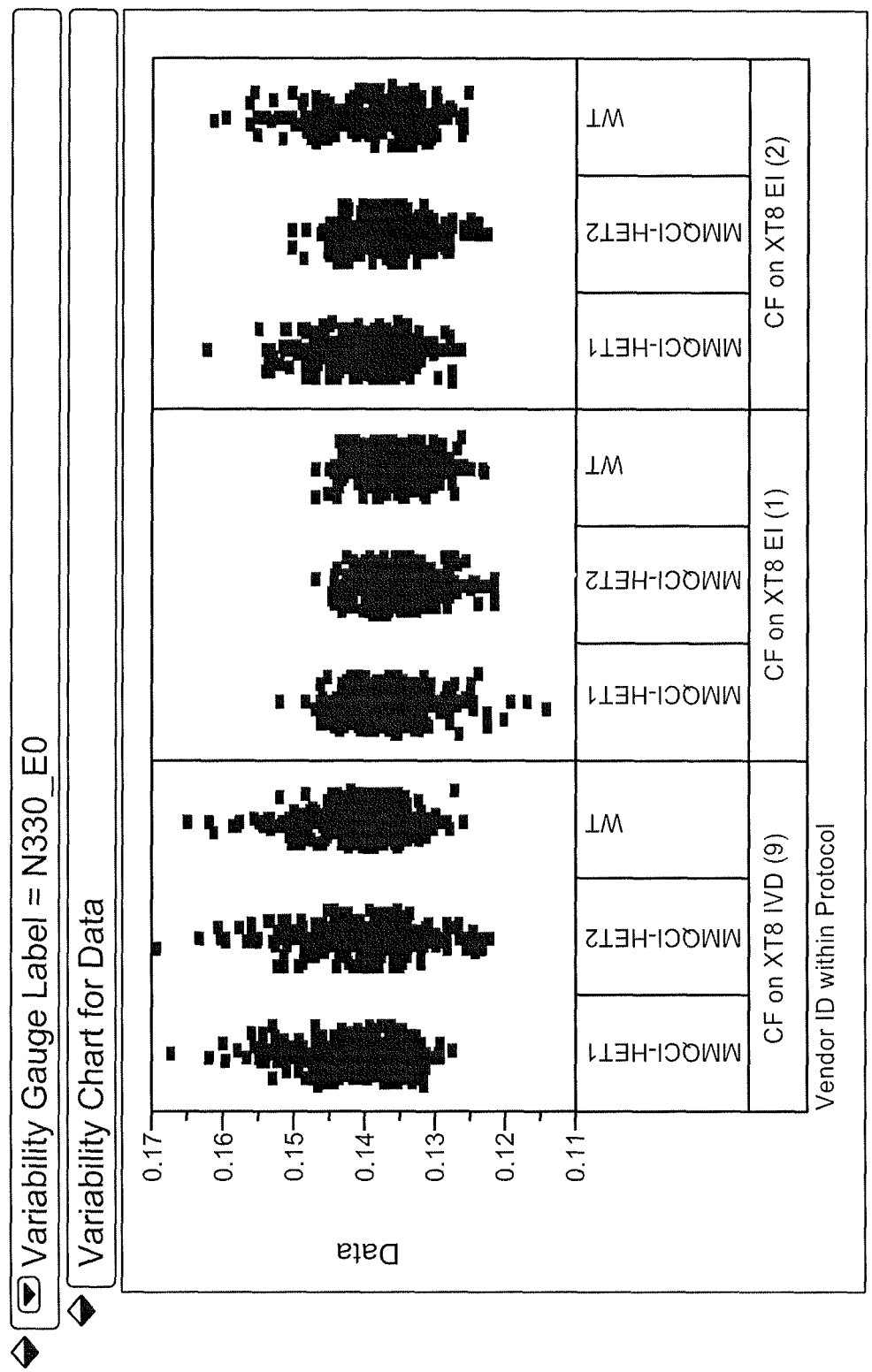
FIG. 17 depicts a cystic fibrosis chip analysis showing that the electrode initialization reduces E0 variability and localizes it to the expected E0 of the ferrocene label. There are three identified probes, the wild type and two different alleles, MMQC1 HET1 and MMQC1 HET2. The control, e.g. no initialization, are the three left hand data samples. The EI(1) protocol is a sweep of 150 to +750 mV for 5 seconds, and the EI(2) protocol is a sweep of 150 to +750 mV for 2 seconds. In this case, the 5 second sweep localizes the E0 better than either no EI or a 2 second EI.
Figure 18:
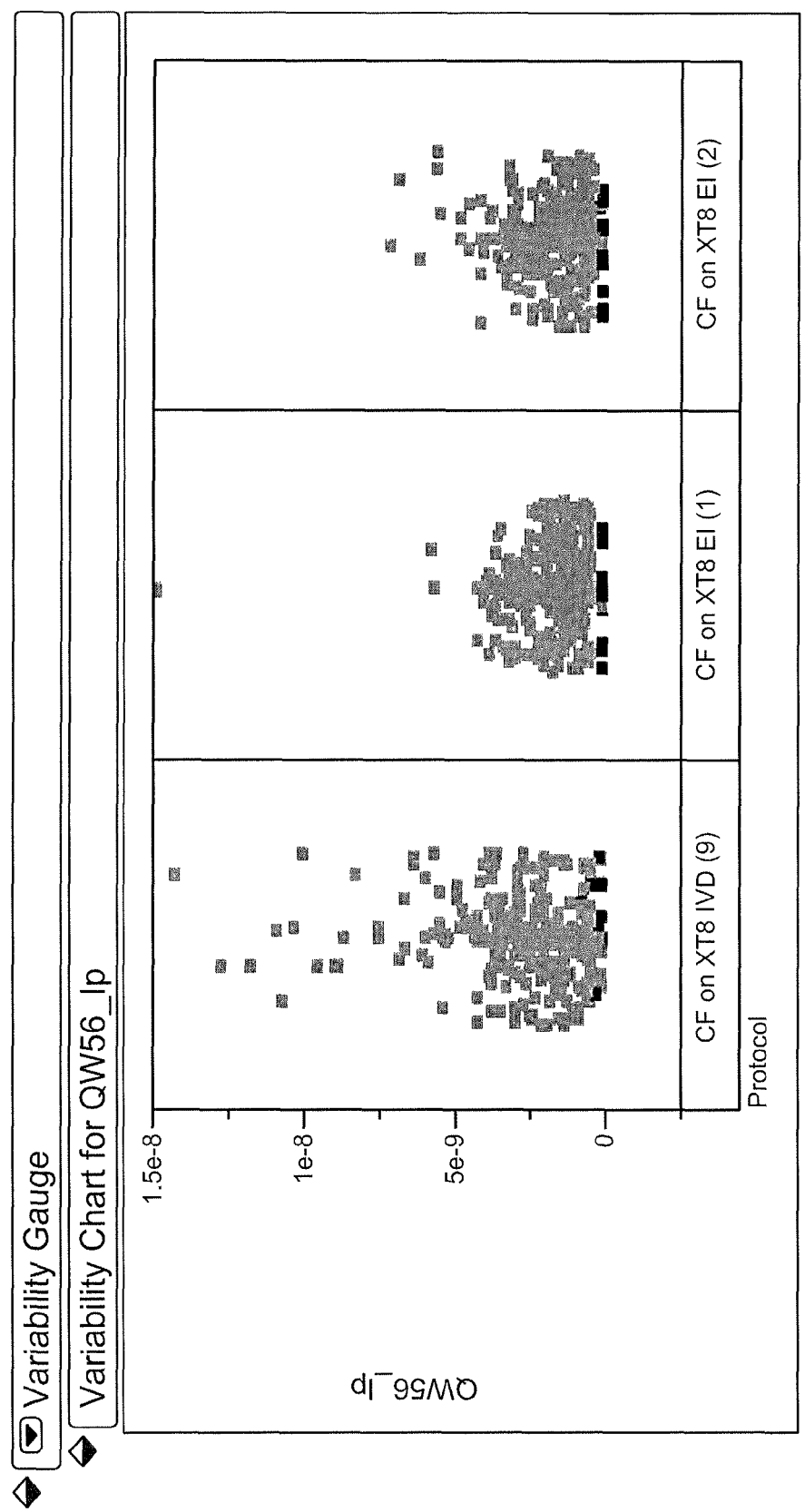
FIG. 18 shows the score shifting that happens on a cystic fibrosis chip, as the EI reduces non-specific binding (FIG. 18) and improves scores for the affected analytes (see FIG. 19). The EI protocols are as described in FIG. 17.
Figure 19A:
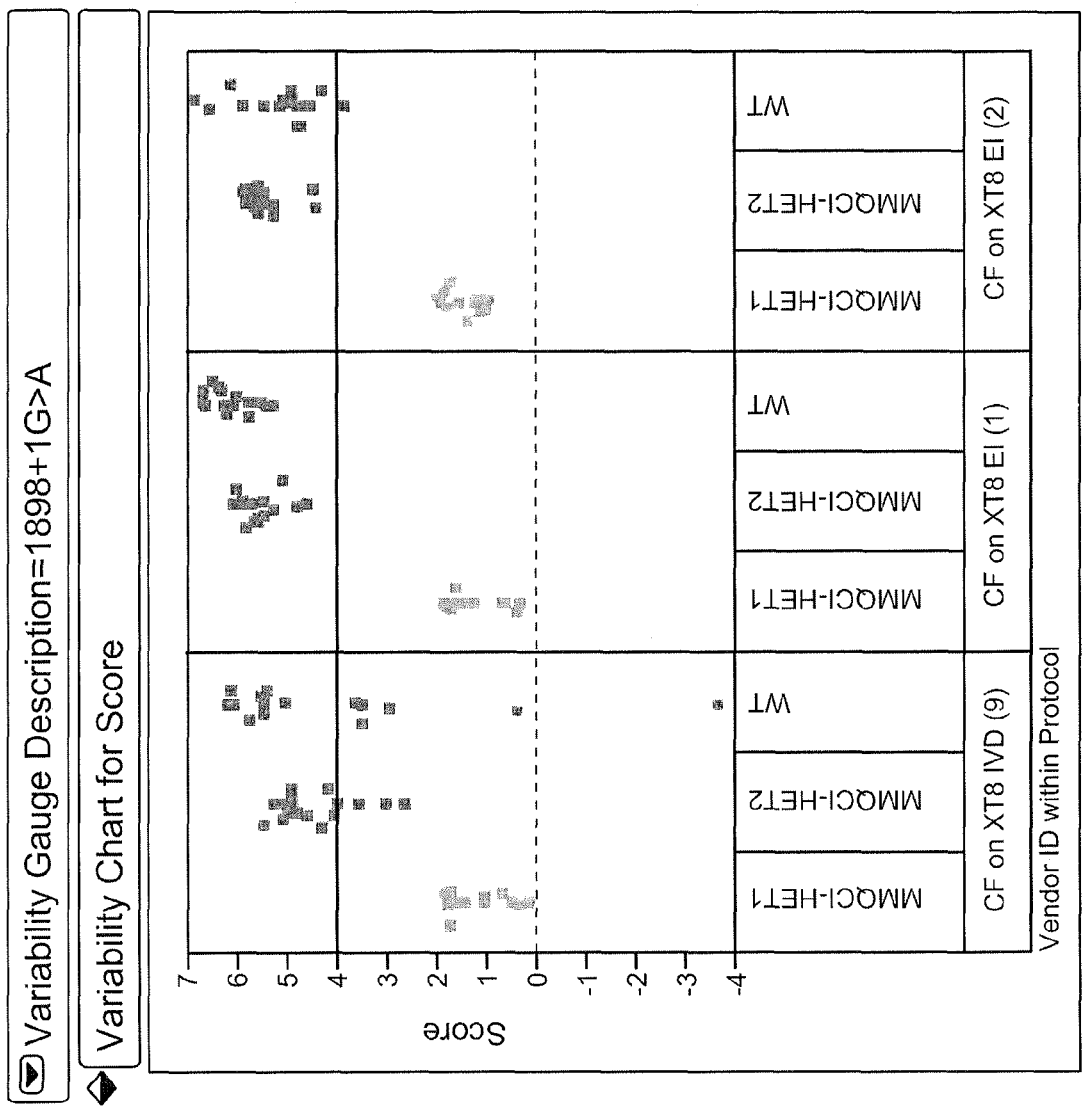
FIGS. 19A and 19B show the improved scores for particular analytes.
Figure 19B:
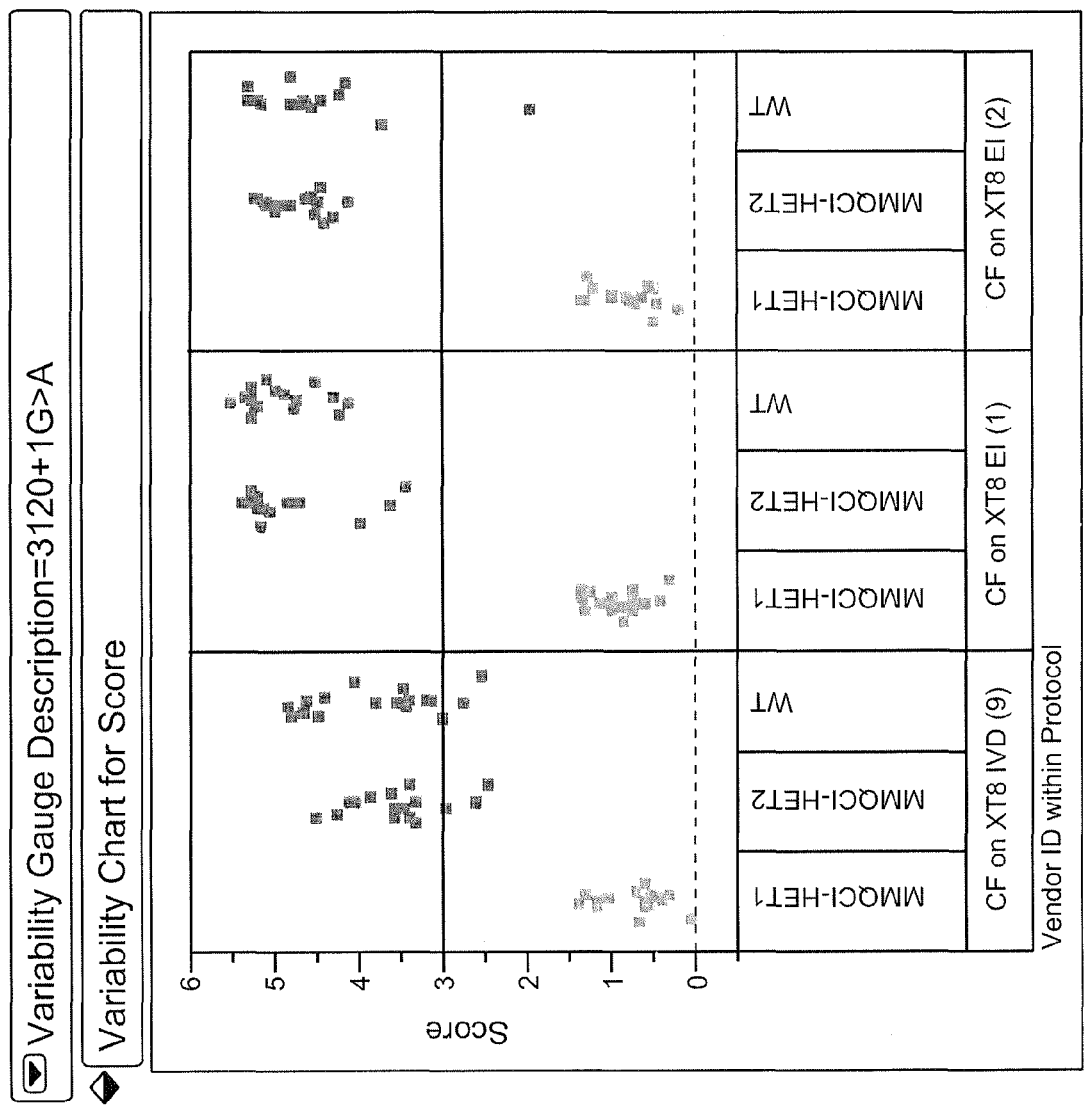
Figure 20A:
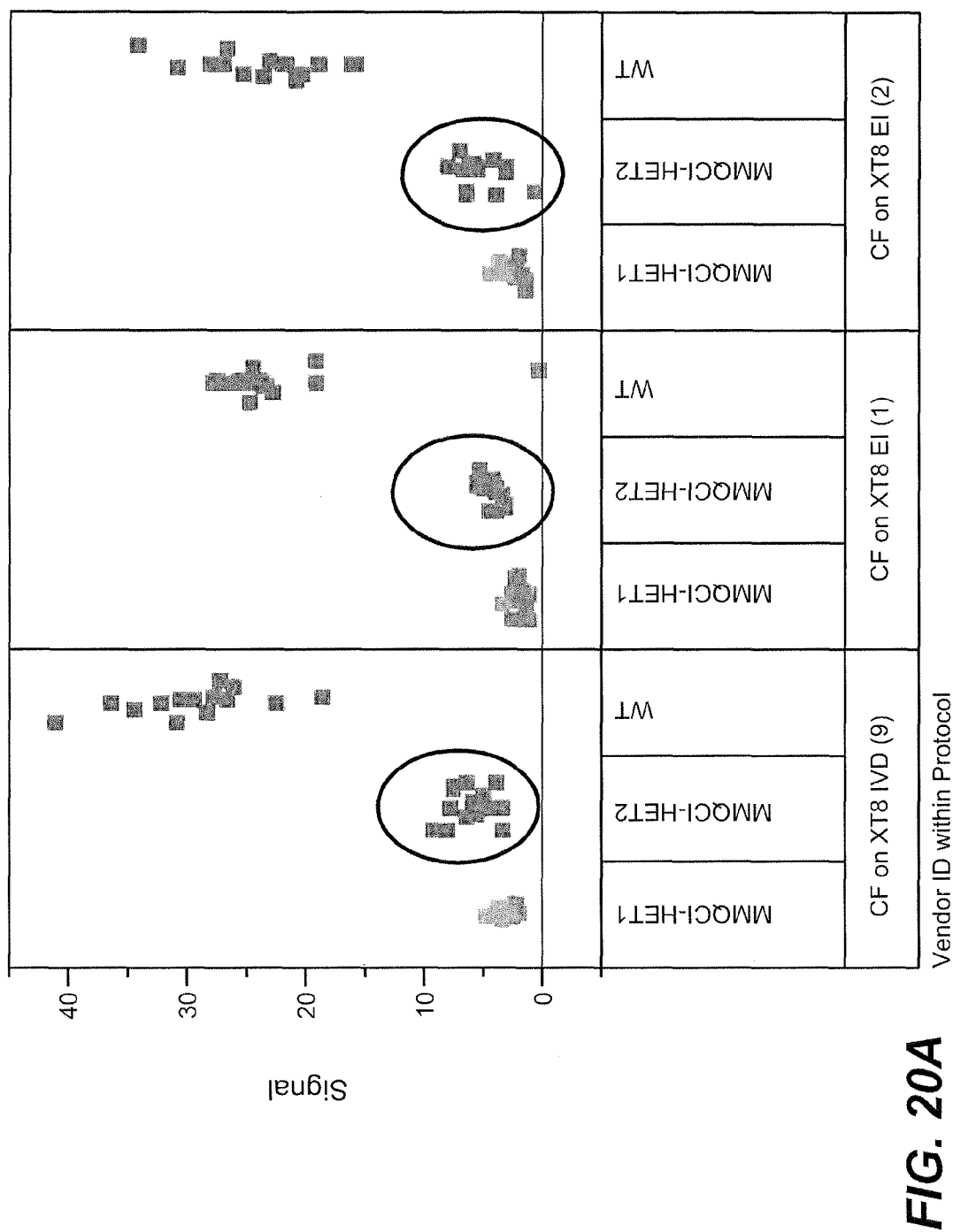
FIGS. 20A and 20B depicts the reduction of low signal miscalls, as EI improves the scores, as signals just above threshold show improved scores.
Figure 20B:
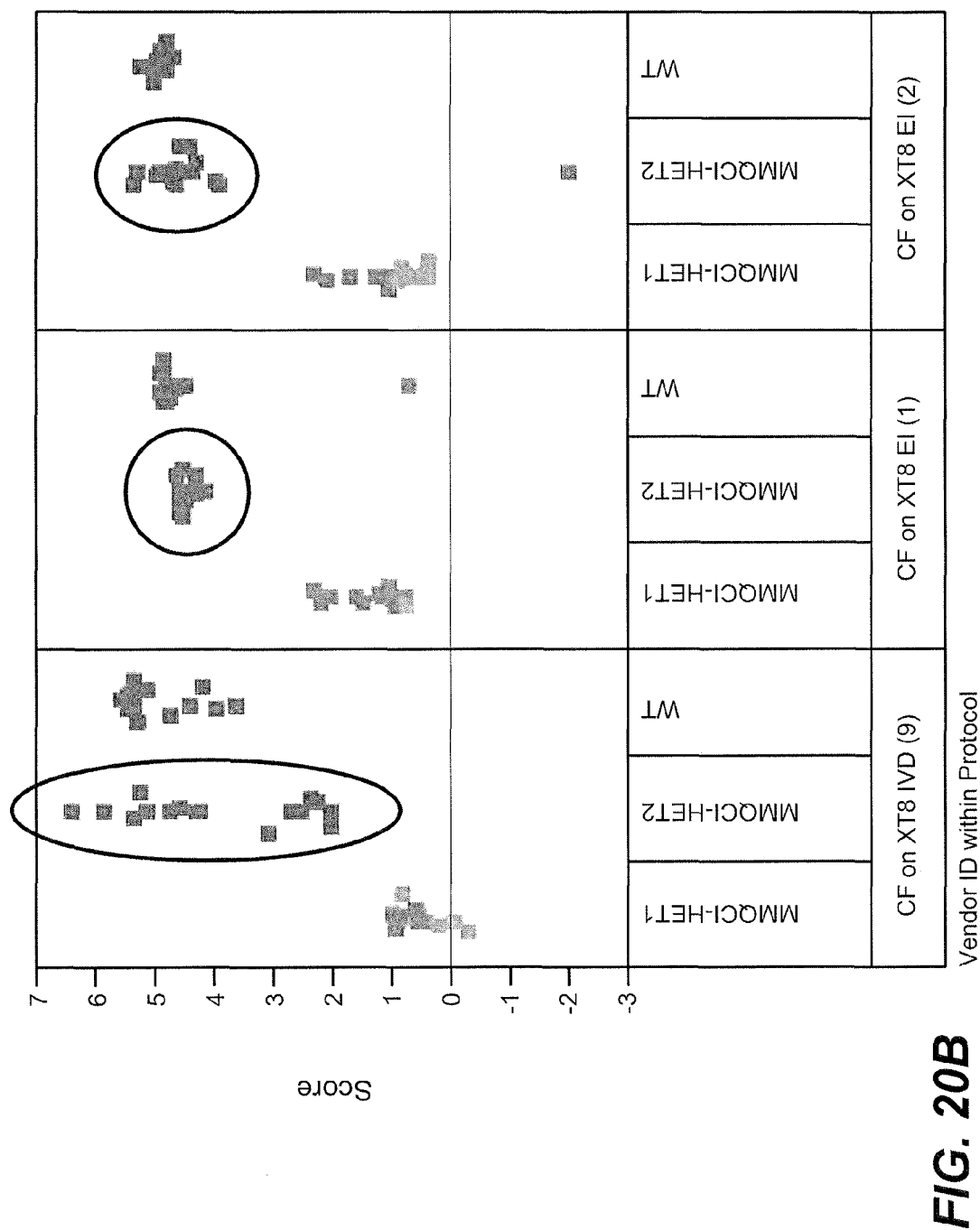
Figure 21A:
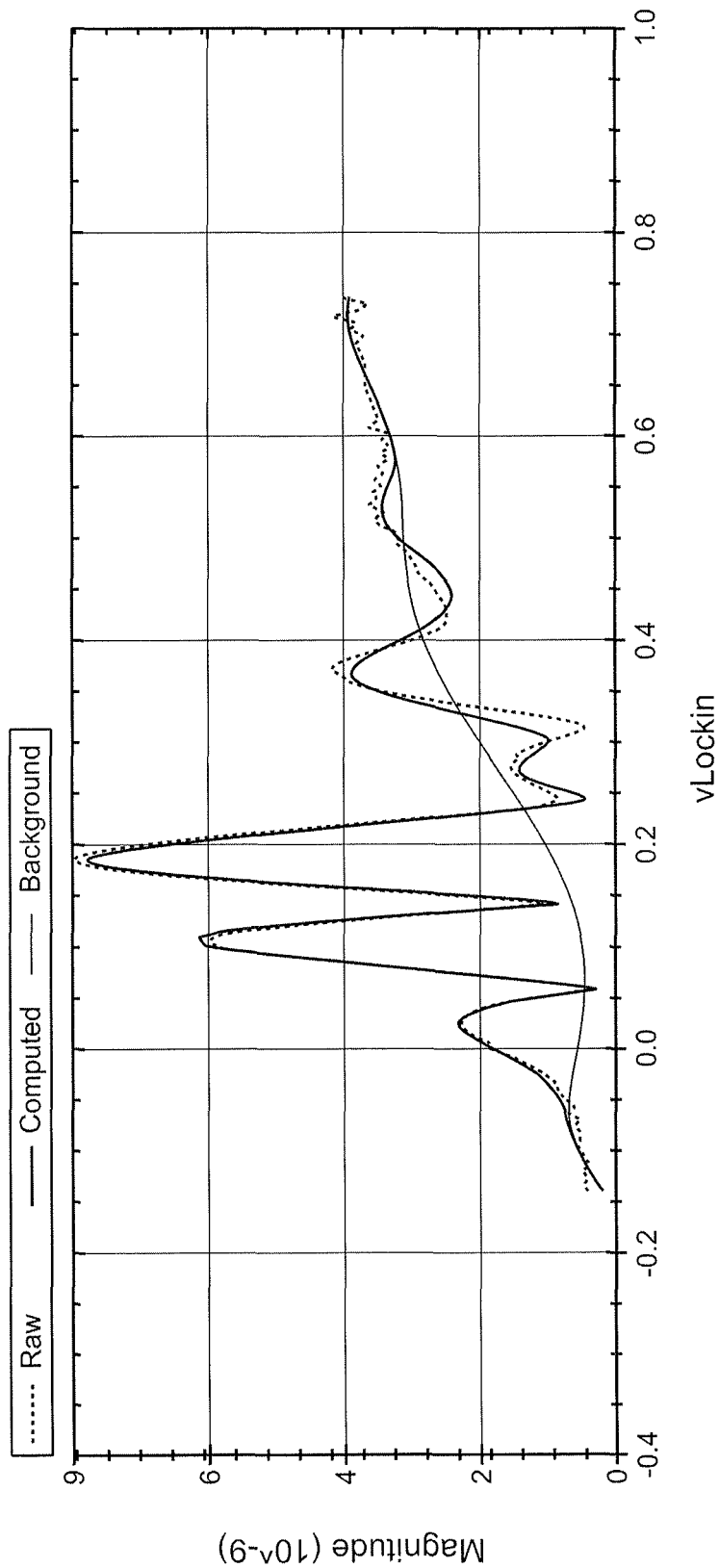
FIGS. 21A and 21B show the elimination of the tailing effect in signal trace that can cause poor curve fit.
Figure 21B:
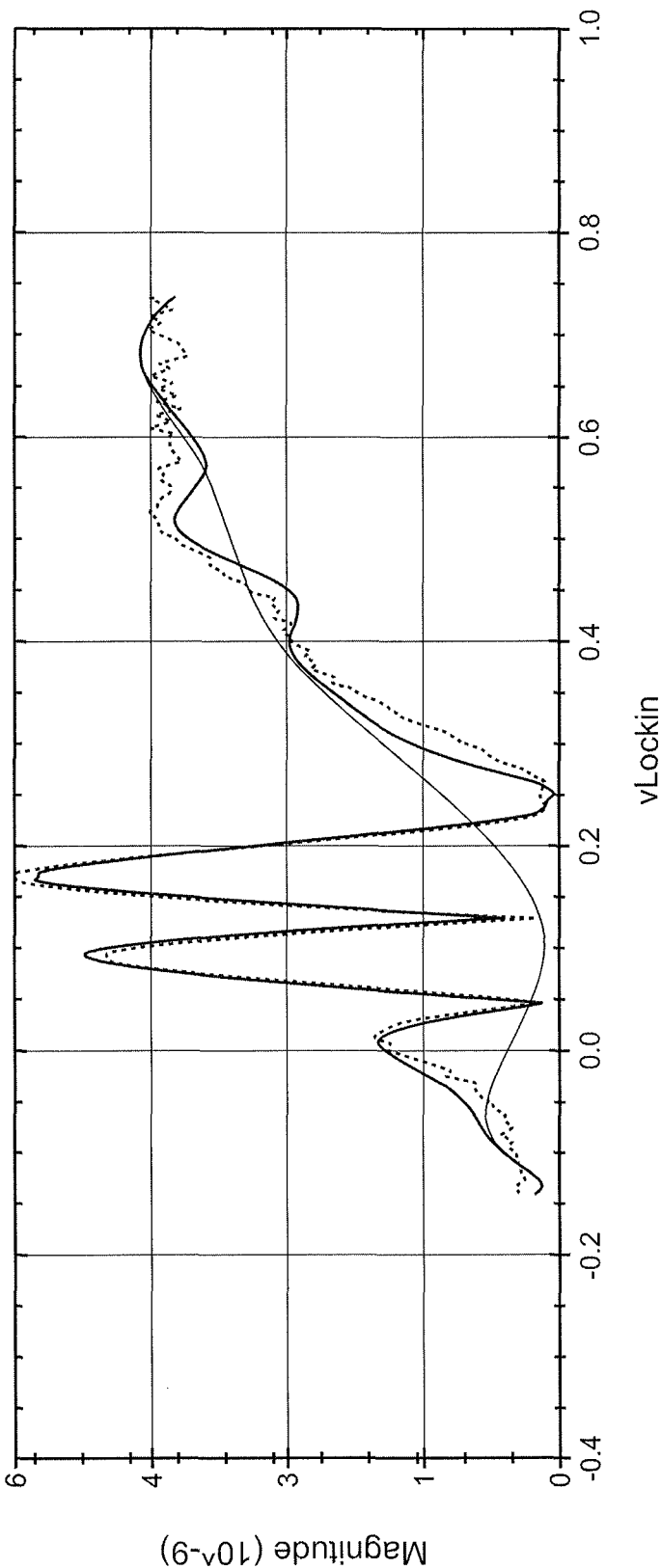
Figure 22B:
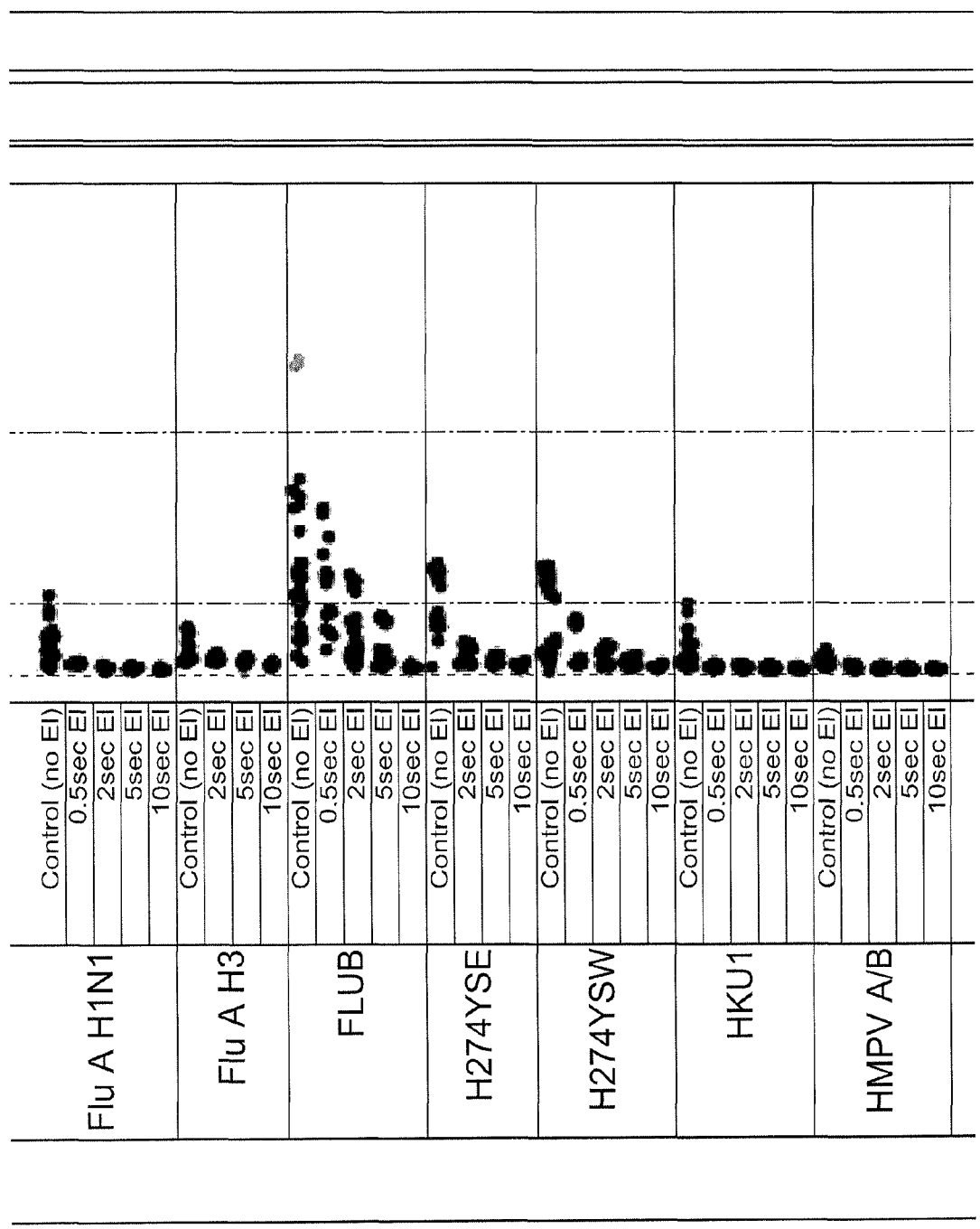
FIG. 22, from a respiratory viral panel chip, shows the effectiveness of the EI protocols (in this case using 0.5, 2, 5 and 10 second sweep) in reducing the variability of the signals. In addition.
Figure 22C:
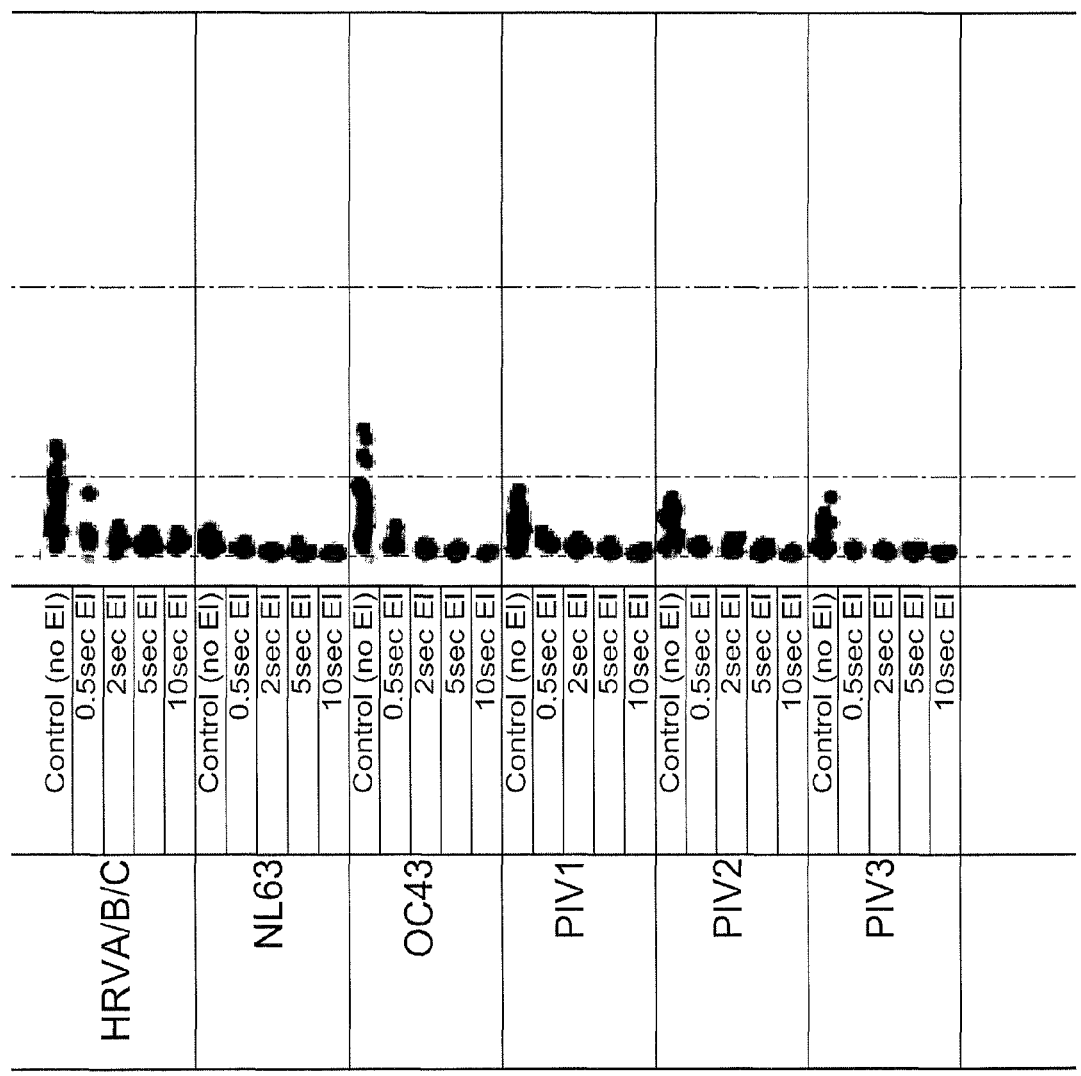
Figure 22D:
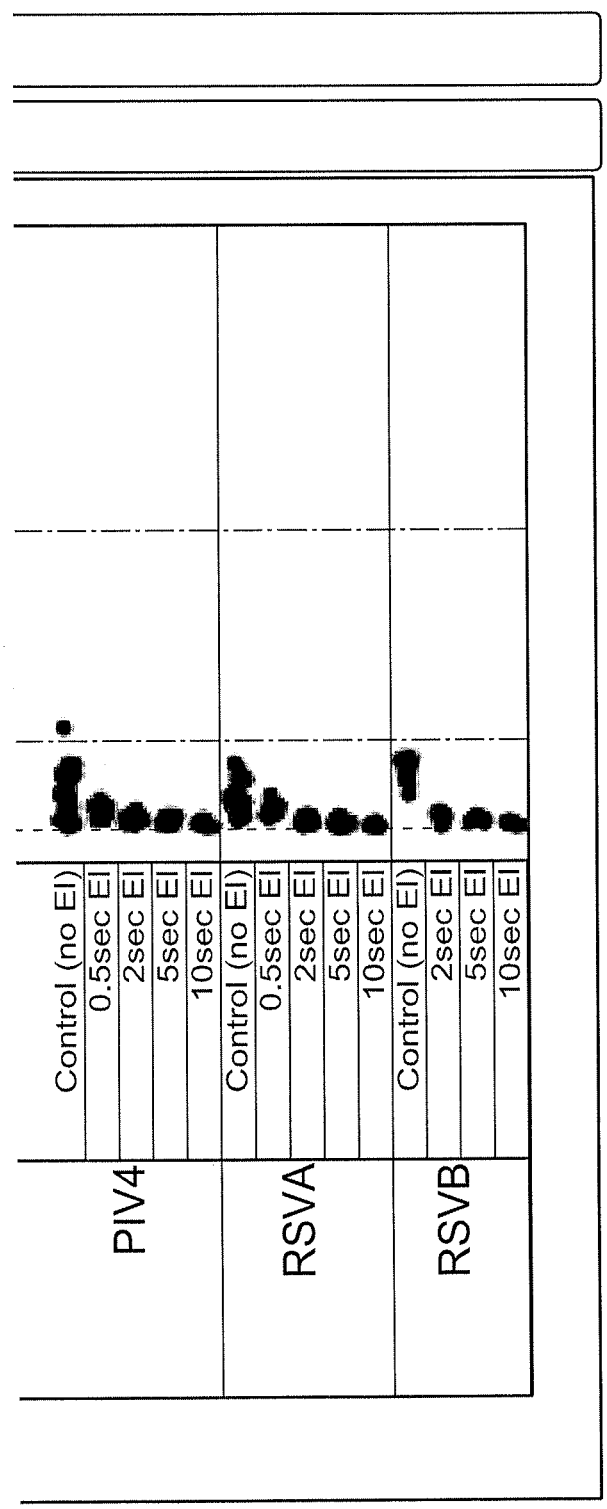
Figure 23:
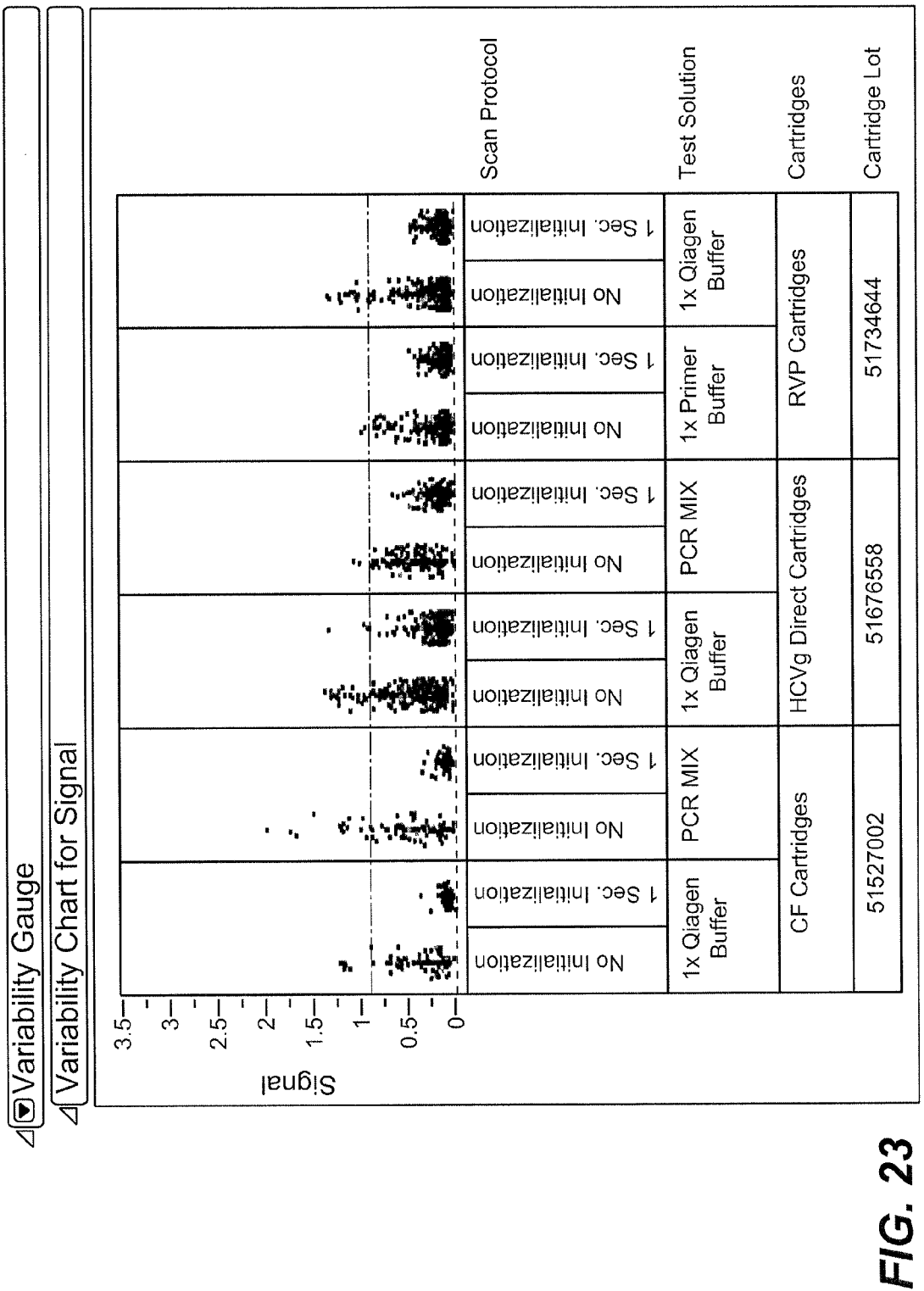
FIG. 23, also a RVP chip, shows that the EI protocols background signal improves signals across different chips and samples. The background is observed with non-amplified PCR buffers or Qiagen buffer.

In addition, as is described below, when the recruitment linker is nucleic acid, it may be desirable to use secondary label probes, that have a first portion that will hybridize to a portion of the primary label probes and a second portion comprising a recruitment linker as is defined herein. This is generally depicted in FIG. 16H of U.S. Ser. No. 60/190,259.

In an embodiment, the ETM is attached to the base of a nucleoside as is generally outlined above for attachment of the attachment linkers. Attachment can be to an internal nucleoside or a terminal nucleoside.

The covalent attachment to the base will depend in part on the ETM chosen. Attachment may generally be done to any position of the base. In an embodiment, the ETM is a transition metal complex, and thus attachment of a suitable metal ligand to the base leads to the covalent attachment of the ETM. Alternatively, similar types of linkages may be used for the attachment of organic ETMs, as will be appreciated by those in the art.

In one embodiment, the C4 attached amino group of cytosine, the C6 attached amino group of adenine, or the C2 attached amino group of guanine may be used as a transition metal ligand.

Ligands containing aromatic groups can be attached via acetylene linkages as is known in the art (see Comprehensive Organic Synthesis, Trost et al., Ed., Pergamon Press, Chapter 2.4: Coupling Reactions Between $sp^2$ and sp Carbon Centers, Sonogashira, pp 521-549, and pp 950-953, hereby incorporated by reference). Structure 9 depicts a representative structure in the presence of the metal ion and any other necessary ligands; Structure 30 depicts uridine, although as for all the structures herein, any other base may also be used.

Structure 9

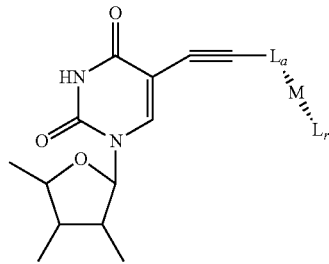

$L_a$ is a ligand, which may include nitrogen, oxygen, sulfur or phosphorus donating ligands or organometallic ligands such as metallocene ligands. Suitable $L_a$ ligands include, but are not limited to, phenanthroline, imidazole, bpy and terpy. $L_r$ and M are as defined above. Again, it will be appreciated by those in the art, that a linker ("Z") may be included between the nucleoside and the ETM.

Similarly, as for the attachment linkers, the linkage may be done using a linker, which may utilize an amide linkage (see generally Telser et al., J. Am. Chem. Soc. 111:7221-7226 (1989); Telser et al., J. Am. Chem. Soc. 111:7226-7232 (1989), both of which are expressly incorporated by reference). These structures are generally depicted below in Structure 10, which again uses uridine as the base, although as above, the other bases may also be used:

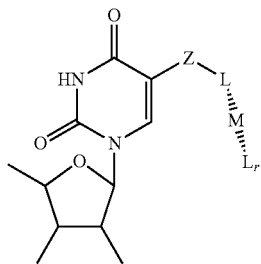

Structure 10

In this embodiment, L is a ligand as defined above, with $L_r$ and M as defined above as well. Preferably, L is amino, phen, byp and terpy.

In an embodiment, the ETM attached to a nucleoside is a metallocene; e.g. the L and $L_r$ of Structure 10 are both metallocene ligands, $L_m$, as described above. Structure 11 depicts an embodiment wherein the metallocene is ferrocene, and the base is uridine, although other bases may be used:

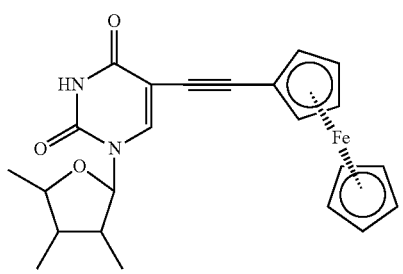

Structure 11

Preliminary data suggest that Structure 11 may cyclize, with the second acetylene carbon atom attacking the carbonyl oxygen, forming a furan-like structure. Metallocenes can include ferrocene, cobaltocene and osmiumocene.

In an embodiment, the ETM is attached to a ribose at any position of the ribose-phosphate backbone of the nucleic acid, e.g. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well. Embodiments can utilize attachment at the 2' or 3' position of the ribose, with the 2' position being preferred.

In an embodiment, a metallocene serves as the ETM, and is attached via an amide bond as depicted below in Structure 12. The examples outline the synthesis of a compound when the metallocene is ferrocene.

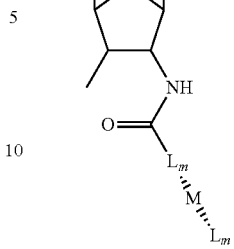

Structure 12

In an embodiment, amine linkages are used, as is generally depicted in Structure 13.

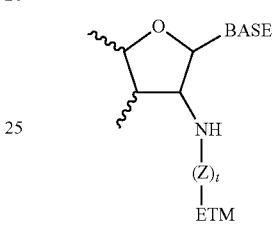

Structure 13

Z is a linker, as defined herein, with 1-16 atoms being preferred, and 2-4 atoms being particularly preferred, and t is either one or zero.

In an embodiment, oxo linkages are used, as is generally depicted in Structure 14.

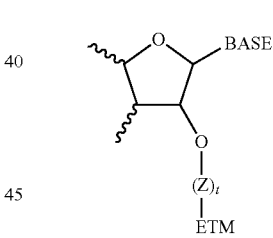

Structure 14

In Structure 14, Z is a linker, as defined herein, and t is either one or zero. Z linkers can include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

Linkages utilizing other heteroatoms are also possible.

In an embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (e.g. nitrogen) serves as a transition metal ligand (see PCT publication WO 95/15971, incorporated by reference). In an embodiment, the composition has the structure shown in Structure 15.

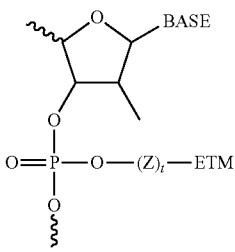

Structure 15

In Structure 15, the ETM is attached via a phosphate linkage, generally through the use of a linker, Z. Z linkers can include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred.

When the ETM is attached to the base or the backbone of the nucleoside, it is possible to attach the ETMs via "dendrimer" structures, as is more fully outlined below. Alkyl-based linkers can be used to create multiple branching structures comprising one or more ETMs at the terminus of each branch (although internal ETMs can be used as well). Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions. The branch point can be an internal one or a terminal one, and can be a chemical branch point or a nucleoside branch point.

In an embodiment, an ETM such as a metallocene is used as a "nucleoside replacement", serving as an ETM. For example, the distance between the two cyclopentadiene rings of ferrocene is similar to the orthongonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 16 (nucleic acid with a ribose-phosphate backbone) and Structure 38 (peptide nucleic acid backbone). Structures 16 and 17 depict ferrocene, although as will be appreciated by those in the art, other metallocenes may be used as well. In general, air stable metallocenes can include metallocenes utilizing ruthenium and cobalt as the metal.

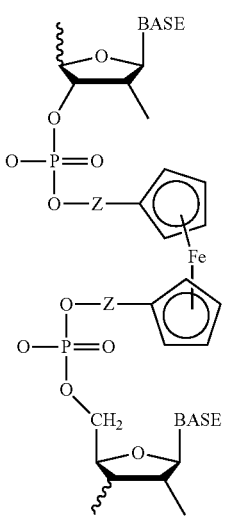

Structure 16

In Structure 16, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 16 depicts a ribose-phosphate backbone, although as will be appreciated by those in the art, nucleic acid analogs may also be used, including ribose analogs and phosphate bond analogs.

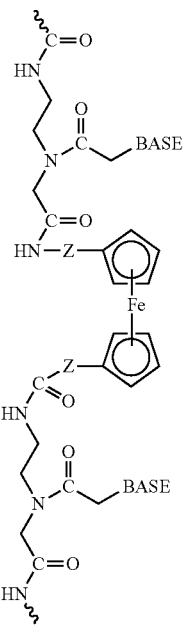

Structure 17

In Structure 17, Z groups are as listed above, and again, each Z linker can be the same or different. As above, other nucleic acid analogs may be used as well.

In addition, although the structures and discussion above depict metallocenes, and particularly ferrocene, this same general idea can be used to add ETMs in addition to metallocenes, as nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Complexes comprising at least two ring (for example, aryl and substituted aryl) ligands can include, where each of the ligands comprises functional groups for attachment via phosphoramidite chemistry. As will be appreciated by those in the art, this type of reaction, creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

Thus, by inserting a metallocene such as ferrocene (or other ETMs) into the backbone of a nucleic acid, nucleic acid analogs are made; that is, the invention provides nucleic acids having a backbone comprising at least one metallocene. This is distinguished from nucleic acids having metallocenes attached to the backbone, e.g. via a ribose, a phosphate, etc. That is, two nucleic acids each made up of a traditional nucleic acid or analog (nucleic acids in this case including a single nucleoside), may be covalently attached to each other via a metallocene. Viewed differently, a metallocene derivative or substituted metallocene is provided, wherein each of the two aromatic rings of the metallocene has a nucleic acid substitutent group.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers"; that is, there are areas of metallocene polymers within the backbone.

In addition to the nucleic acid substituent groups, it is also desirable in some instances to add additional substituent groups to one or both of the aromatic rings of the metallocene (or ETM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substituent groups include, but are not limited to, amide groups, amine groups, carboxylic acids, and alcohols, including substituted alcohols. In addition, these substitutent groups can be attached via linkers as well, although in general this is not preferred.

In addition, substituent groups on an ETM, particularly metallocenes such as ferrocene, may be added to alter the redox properties of the ETM. Thus, for example, in some embodiments, as is more fully described below, it may be desirable to have different ETMs attached in different ways (e.g. base or ribose attachment), on different probes, or for different purposes (for example, calibration or as an internal standard). Thus, the addition of substituent groups on the metallocene may allow two different ETMs to be distinguished.

In order to generate these metallocene-backbone nucleic acid analogs, the intermediate components are also provided. Thus, In an embodiment, the invention provides phosphoramidite metallocenes, as generally depicted in Structure 18:

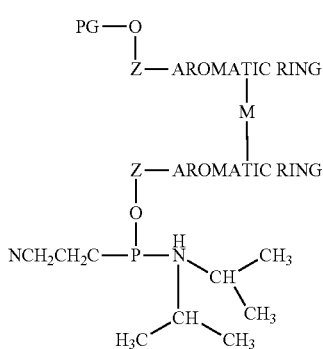

Structure 18

In Structure 18, PG is a protecting group, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein.

Structure 19 depicts the ferrocene derivative:

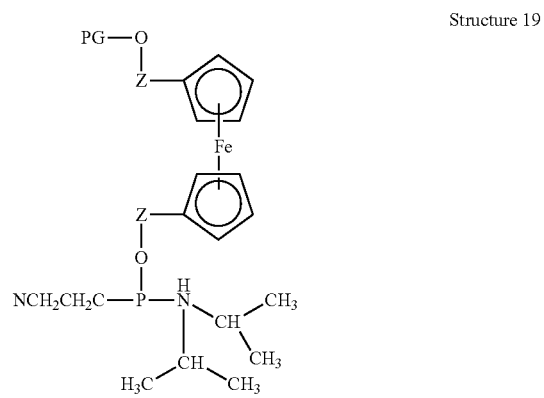

Structure 19

These phosphoramidite analogs can be added to standard oligonucleotide syntheses as is known in the art.

Structure 20 depicts the ferrocene peptide nucleic acid (PNA) monomer, that can be added to PNA synthesis as is known in the art:

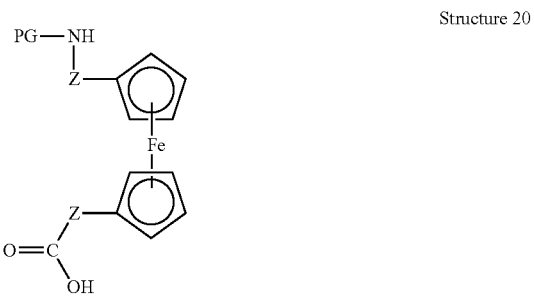

Structure 20

In Structure 20, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In an embodiment, the ETMs are attached as polymers, for example as metallocene polymers, in a "branched" configuration similar to the "branched DNA" embodiments herein and as outlined in U.S. Pat. No. 5,124,246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in structures 18 and 19, ETMs, such as metallocene ETMs, are added. Additional phosphoramidite ETMs such as metallocenes can be added, to form "ETM polymers", including "metallocene polymers" as depicted herein, particularly for ferrocene. In addition, in some embodiments, it is desirable to increase the solubility of the polymers by adding a "capping" group to the terminal ETM in the polymer, for example a final phosphate group to the metallocene. Other suitable solubility enhancing "capping" groups will be appreciated by those in the art. It should be noted that these solubility enhancing groups can be added to the polymers in other places, including to the ligand rings, for example on the metallocenes as discussed herein In an embodiment, (as depicted in the figures of U.S. Ser. No. 09/626,096) the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a growing nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 20, peptide nucleic acid structures containing metallocene polymers could be generated.

Thus, the present invention provides recruitment linkers of nucleic acids comprising "branches" of metallocene polymers. Embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done.

In an embodiment, the recruitment linker is not nucleic acid, and instead can be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contains functional groups for the covalent attachment of ETMs. In some embodiments coupling moieties are used to covalently link the subunits with the ETMs. Functional groups for attachment can include amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo- or hetero-bifunctional linkers as are well known (see 1994 Pierce Chemical Company catalog, technical section on cross-linkers, pages 155-200, incorporated herein by reference).

Suitable recruitment polymers include, but are not limited to, functionalized styrenes, such as amino styrene, functionalized dextrans, and polyamino acids. Polymers can include polyamino acids (both poly-D-amino acids and poly-L-amino acids), such as polylysine, and polymers containing lysine and other amino acids being particularly preferred. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In an embodiment, the recruitment linker comprises a metallocene polymer, as is described above.

The attachment of the recruitment linkers to the first portion of the label probe will depend on the composition of the recruitment linker, as will be appreciated by those in the art. When the recruitment linker is nucleic acid, it is generally formed during the synthesis of the first portion of the label probe, with incorporation of nucleosides containing ETMs as required. Alternatively, the first portion of the label probe and the recruitment linker may be made separately, and then attached. For example, there may be an overlapping section of complementarity, forming a section of double stranded nucleic acid that can then be chemically cross-linked, for example by using psoralen as is known in the art.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (e.g. nucleic acid segments linked together with alkyl linkers) or in branched forms (nucleic acids with alkyl "branches" that may contain ETMs and may be additionally branched).

In an embodiment, it is the target sequence itself that carries the ETMs, rather than the recruitment linker of a label probe. For example, as is more fully described below, it is possible to enzymatically add triphosphate nucleotides comprising the ETMs of the invention to a growing nucleic acid, for example during a polymerase chain reaction (PCR). As will be recognized by those in the art, while several enzymes have been shown to generally tolerate modified nucleotides, some of the modified nucleotides of the invention, for example the "nucleoside replacement" embodiments and putatively some of the phosphate attachments, may or may not be recognized by the enzymes to allow incorporation into a growing nucleic acid. Therefore, attachments in this embodiment are to the base or ribose of the nucleotide.

Thus, for example, PCR amplification of a target sequence, as is well known in the art, will result in target sequences comprising ETMs, generally randomly incorporated into the sequence. The system of the invention can then be configured to allow detection using these ETMs, as is generally depicted in FIGS. 16A, 16B and 16D of U.S. Ser. No. 60/190,259.

Alternatively, it is possible to enzymatically add nucleotides comprising ETMs to the terminus of a nucleic acid, for example a target nucleic acid. In this embodiment, an effective "recruitment linker" is added to the terminus of the target sequence, that can then be used for detection. Thus the invention provides compositions utilizing electrodes comprising monolayers and capture probes, and target sequences that comprise a first portion that is capable of hybridizing to a component of an assay complex, and a second portion that does not hybridize to a component of an assay complex and comprises at least one covalently attached electron transfer moiety. Similarly, methods utilizing these compositions are also provided.

It is also possible to have ETMs connected to probe sequences, e.g. sequences designed to hybridize to complementary sequences. Thus, ETMs may be added to non-recruitment linkers as well. For example, there may be ETMs added to sections of label probes that do hybridize to components of the assay complex, for example the first portion, or to the target sequence as outlined above. These ETMs may be used for electron transfer detection in some embodiments, or they may not, depending on the location and system. For example, in some embodiments, when for example the target sequence containing randomly incorporated ETMs is hybridized directly to the capture probe, as is depicted in FIG. 16A of U.S. Ser. No. 60/190,259, there may be ETMs in the portion hybridizing to the capture probe.

Similarly, in some embodiments, when the recruitment linker is nucleic acid, it may be desirable in some instances to have some or all of the recruitment linker be double stranded. In one embodiment, there may be a second recruitment linker, substantially complementary to the first recruitment linker that can hybridize to the first recruitment linker. In an embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, e.g. the $T_m$ may be decreased, depending on the site of attachment and the characteristics of the ETM. Thus, in general, when multiple ETMs are used on hybridizing strands, generally there are less than about 5, with less than about 3 being preferred, or alternatively the ETMs should be spaced sufficiently far apart that the intervening nucleotides can sufficiently hybridize to allow good kinetics.

In one embodiment, non-covalently attached ETMs may be used. In one embodiment, the ETM is a hybridization indicator. Hybridization indicators serve as ETMs that will preferentially associate with double stranded nucleic acid, usually reversibly, similar to the method of Millan et al., *Anal. Chem.* 65:2317-2323 (1993); Millan et al., *Anal. Chem.* 662943-2948 (1994), both of which are hereby expressly incorporated by reference. In this embodiment, increases in the local concentration of ETMs, due to the association of the ETM hybridization indicator with double stranded nucleic acid at the surface, can be monitored using the monolayers comprising insulators. Hybridization indicators include intercalators and minor and/or major groove binding moieties. In an embodiment, intercalators may be used; since intercalation generally only occurs in the presence of double stranded nucleic acid, only in the presence of double stranded nucleic acid will the ETMs concentrate. Intercalating transition metal complex ETMs are known in the art. Similarly, major or minor groove binding moieties, such as methylene blue, may also be used in this embodiment.

Similarly, the systems of the invention may utilize non-covalently attached ETMs, as is generally described in Napier et al., *Bioconj. Chem.* 8:906 (1997), hereby expressly incorporated by reference. In this embodiment, changes in the redox state of certain molecules as a result of the presence of DNA (e.g. guanine oxidation by ruthenium complexes) can be detected using SAMs.

Thus, the present invention provides electrodes comprising monolayers, generally including capture probes, and either target sequences or label probes comprising recruitment linkers containing ETMs. Probes of the present invention are designed to be complementary to a target sequence (either the target sequence of the sample or to other probe sequences, as is described below), such that hybridization of the target sequence and the probes of the present invention occurs. This complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

Electrode Initialization

In an embodiment the electrode is initialized prior to the formulation of an assay complex. As used herein, "initialization" and all grammatical equivalents thereof refer to the process of applying an electronic scan to a monolayer-containing cartridge prior to hybridization of an analyte and formation of an assay complex. Electrode initialization (EI) is a step that can be used to promote specific signal, and/or decrease the noise, and/or make the signal more obvious or detectable in a background of noise.

Without being bound by theory, EI uses an electronic signal to treat a monolayer by preventing non-specific binding of free-floating ETM probes. Without EI, probes that would normally hybridize to a target analyte sometimes diffuse toward the monolayer without hybridizing to the target. This creates non-specific signals and variable signal potentials. In contrast, if EI is utilized by applying, for example, a short voltage scan to a monolayer-containing cartridge post initial wetting, the voltage pulses drives non-specific probes away from the monolayer and prevents significant amounts non-specific signals and current potential variability. The prevention of non-specific signals results in a higher signal to noise ratio observed during the detection steps described herein.

In an embodiment, EI improves $E_0$ stability. In this EI context, "$E_0$" refers to the redox potential, which refers to the voltage which must be applied to an electrode (relative to a standard reference electrode such as a normal hydrogen electrode) such that the ratio of oxidized and reduced ETMs is one in the solution near the electrode. An improved $E_0$ stability results in a lower $E_0$ that is shifted less from an expected $E_0$ range relative to samples tested without EI. $E_0$ shifting, e.g., can result from variations in the reference electrode, which occurs when the potential at which an ETM label is shifting, thus resulting in a poor fit of a signal trace. $E_0$ shifting can result in no calls and miscalls as described below.

In an embodiment, EI improves score shift. As used herein "score shift" refers to a wild-type:mutant signal ratio. Score shifting can occur, for example, when the presence of non-specific labels settle near the surface of an electrodes. Detection of these non-specific labels result in the score being shifted closer to an indeterminate boundary of an assay's calling parameters. Score shifting can result in no calls and miscalls as described below.

In an embodiment, EI reduces low signal miscalls. Low signal miscalls can result from a poorly processed sample, which in turn results in a signal that while barely exceeds a signal threshold, the signal is incorrectly fit due to the shape of the signal trace. Score shifting can result in no calls and miscalls as described below.

During analyte detection, the combined major allele and minor allele current (signal) generated for each electrode is usually evaluated against a pre-established signal threshold. The genotyping score, which is derived from the ratio of different ETM signals for each electrode passing the signal strength threshold parameter, can be evaluated and compared to different boundaries. These boundaries are unique for each polymorphism and can be determined empirically using test performance data. The boundaries define zones for classification of scores for a homozygous major allele, a homozygous minor allele and heterozygote genotypes. There can be two 'indeterminate' zones; one between the homozygous major allele and heterozygote boundaries, and a second between the heterozygote and homozygous minor allele boundaries. If the score from an electrode falls in this zone, it cannot be classified as a specific genotype, and is considered a no-call due to "indeterminate score." An indeterminate score can be considered a no call to prevent miscalls, as only robust scores can be used to assign a genotype.

Without being bound by theory, by combating $E_0$ shifting and non-specific signal, EI promotes a more robust genotype score by eliminating a signal that can be measured with signal strength, evaluated within genotype score logic, and potentially shift an ETM ratio into an indeterminate score zone or into the incorrect ratio zone, resulting in no calls and miscalls.

EI can be accomplished, for example, by applying an electronic signal prior to running the detection assays as described herein. Briefly, an electronic initialization signal can be applied via at least a sample electrode (containing the complexes of the invention) and a counter electrode to initiate electron transfer between an electrode and non-specific probes.

In an embodiment, the electronic initialization signal can comprise at least an AC component. In an embodiment, the AC frequency is varied. In an embodiment, multiple frequencies of AC voltage are applied. In an embodiment, several frequencies with a large AC voltage can be applied. The AC frequency can range from 90-1000 Hz. The AC voltage can range from −150 to 880 mV rms. EI can be completed in 0.5 seconds, 2 seconds, 5 seconds, 10 seconds, or longer than 10 seconds.

In an embodiment, combinations of AC and DC signals, such as AC/CD offset described below, can be used for EI. Thus, the invention can provide voltage sources capable of delivering both AC and DC currents.

In an embodiment, a plurality of electronic initialization signals is applied. As outlined herein, this may take a variety of forms, including using multiple frequencies, multiple DC offset voltages at a single or two or more frequencies, or multiple AC amplitudes, or combinations of any or all of these.

A skilled artisan will appreciate that a variety of electronic initialization signals, many of which are described in detail herein, can be used that function to drive non-specific probes away from a monolayer and prevent non-specific detectable signals.

Assay Complex

In general, for all the systems outlined herein, both for nucleic acids and other target analytes, the invention provides assay complexes that minimally comprise a target analyte and a capture binding ligand. For nucleic acid target sequences, by "assay complex" herein is meant the collection of hybridization complexes comprising nucleic acids, including probes and targets that contains at least one label (preferably an ETM in the electronic methods of the present invention) and thus allows detection. The composition of the assay complex depends on the use of the different probe components outlined herein. The assay complexes may also include label probes, capture extender probes, label extender probes, and amplifier probes, as outlined herein and in U.S. Ser. No. 09/626,096, depending on the configuration used.

The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions; for example, when an initial hybridization step is done between the target sequence and the label extender and capture extender probes. Running this step at conditions which favor specific binding can allow the reduction of non-specific binding.

The reactions outlined herein may be accomplished in a variety of ways, as will be appreciated by those in the art. Components of the reaction may be added simultaneously, or sequentially, in any order, with embodiments outlined below. In addition, the reaction may include a variety of other reagents. These include reagents like salts, buffers, neutral proteins (e.g. albumin), detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Analyte Detection

Detection of electron transfer, e.g. the presence of the ETMs, is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the other system components, the composition and integrity of the monolayer, and what type of reference electrode is used. As described herein, ferrocene is an ETM.

In some embodiments, co-reductants or co-oxidants are used as is generally described in WO00/16089, hereby expressly incorporated by reference.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedance. These methods include time or frequency dependent methods based on AC or DC currents, pulsed methods, lock-in techniques, filtering (high pass, low pass, band pass), and time-resolved techniques including time-resolved fluorescence.

In one embodiment, the efficient transfer of electrons from the ETM to the electrode results in stereotyped changes in the redox state of the ETM. With many ETMs including the complexes of ruthenium containing bipyridine, pyridine, and imidazole rings, these changes in redox state are associated with changes in spectral properties. Significant differences in absorbance are observed between reduced and oxidized states for these molecules. See for example Fabbrizzi et al., *Chem. Soc. Rev.* 1995 pp 197-202). Such differences can be monitored using a spectrophotometer or simple photomultiplier tube device.

In this embodiment, possible electron donors and acceptors include all the derivatives listed above for photoactivation or initiation. Electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics.

In an embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with $Ru(4,7\text{-biphenyl}_2\text{-phenanthroline})_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with nucleic acid probes in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. *Coord. Chem. Rev.*, V. 84, p. 85-277, 1988). Examples display efficient fluorescence (reasonably high quantum yields) as well as low reorganization energies. These include $Ru(4,7\text{-biphenyl}_2\text{-phenanthroline})_3^{2+}$, $Ru(4,4'\text{-diphenyl-2,2'-bipyridine})_3^{2+}$ and platinum complexes (see Cummings et al., *J. Am. Chem. Soc.* 118:1949-1960 (1996), incorporated by reference). Alternatively, a reduction in fluorescence associated with hybridization can be measured using these systems.

In a further embodiment, electrochemiluminescence is used as the basis of the electron transfer detection. With some ETMs such as $Ru^{2+}(bpy)_3$, direct luminescence accompanies excited state decay. Changes in this property are associated with nucleic acid hybridization and can be monitored with a simple photomultiplier tube arrangement (see Blackburn, G. F. *Clin. Chem.* 37: 1534-1539 (1991); and Juris et al., supra.

In an embodiment, electronic detection is used, including amperommetry, voltammetry, capacitance, and impedence. Suitable techniques include, but are not limited to, electrogravimetry; coulometry (including controlled potential coulometry and constant current coulometry); voltammetry (cyclic voltammetry, pulse voltammetry (normal pulse voltammetry, square wave voltammetry, differential pulse voltammetry, Osteryoung square wave voltammetry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltammetry; and photoelectrochemistry.

In an embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In an embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators and of conductors (such as resistance conductivity, impedance and capacitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In an embodiment, electron transfer is initiated using alternating current (AC) methods. Without being bound by theory, it appears that ETMs, bound to an electrode, generally respond similarly to an AC voltage across a circuit containing resistors and capacitors.

There are a variety of techniques that can be used to increase the signal, decrease the noise, or make the signal more obvious or detectable in a background of noise in addition to the electrode initialization steps described herein. That is, any technique that can serve to better identify a signal in the background noise may find use in the present invention. These techniques are generally classified in three ways: (1) variations in the type or methods of applying the initiation signals (e.g. varying the "input" to maximize or identify the sample signal); (2) data processing, e.g. techniques used on the "output" signals to maximize or identify the sample signal; and (3) variations in the assay itself, e.g. to the electrode surface or to the components of the system, that allow for better identification of the sample signal. Thus, for example, suitable "input" AC methods include, but are not limited to, using multiple frequencies; increasing the AC amplitude; the use of square wave ACV; the use of special or complicated waveforms; etc. Similarly, suitable "output" AC techniques include, but are not limited to, monitoring higher harmonic frequencies; phase analysis or filters; background subtraction techniques (including but not limited to impedance analysis and the use of signal recognition or peak recognition techniques); digital filtering techniques; bandwidth narrowing techniques (including lock-in detection schemes particularly digital lock in); Fast Fourier Transform (FFT) methods; correlation and/or convolution techniques; signal averaging; spectral analysis; etc. Additionally, varying components of the assay can be done to result in the sample signal and the noise signal being altered in a non-parallel fashion; that is, the two signals respond non-linearly with respect to each other. These techniques are described in WO00/16089 and O'Connor et al., *J. Electroanal. Chem.* 466(2):197-202 (1999), hereby expressly incorporated by reference.

In general, non-specifically bound label probes/ETMs show differences in impedance (e.g. higher impedances) than when the label probes containing the ETMs are specifically bound in the correct orientation. In an embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Input Signal

Once the assay complex including the target sequence and label probe is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In an embodiment, the first input signal comprises a DC component and an AC component, which is known at AC/DC offset. That is, a DC offset voltage between the working and counter electrodes is swept through the electrochemical potential of the ETM (for example, when ferrocene is used, the sweep is generally from 0 to 500 mV) (or alternatively, the working electrode is grounded and the counter electrode is swept from 0 to −500 mV). The sweep is used to identify the DC voltage at which the maximum response of the system is seen. This is generally at or about the electrochemical potential of the ETM. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In an embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM. These voltages are meaningful numbers for a Ag vs an AgCl reference electrode.

Thus, the devices of the invention preferably provide voltage sources capable of delivering both AC and DC currents.

For defined systems, it may be sufficient to apply a single input signal to differentiate between the presence and absence of the ETM (e.g. the presence of the target sequence) nucleic acid. Alternatively, a plurality of input signals is applied. As outlined herein, this may take a variety of forms, including using multiple frequencies, multiple DC offset voltages, or multiple AC amplitudes, or combinations of any or all of these.

Thus, In an embodiment, multiple DC offset voltages are used, although as outlined above, DC voltage sweeps are preferred. This may be done at a single frequency, or at two or more frequencies.

In an embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In an embodiment, multiple frequencies with a small AC voltage are applied and the fundamental of each is evaluated. Alternatively, an embodiment utilizes several frequencies with a large AC voltage, and the harmonics of each are evaluated. Similarly, embodiments utilize several frequencies with a large AC voltage where the effect of the different frequencies on the system can result in an output that is different from the sum of the outputs at individual frequencies.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input frequency, and any changes in frequency response is an indication that the ETM is present, and thus that the target sequence is present.

In an embodiment, the input signals and data processing steps are done to increase the non-linearity of the system. That is, for example, the ferrocene response reacts non-linearly, producing a harmonic response in the signal above that in the background; this harmonic signal from AC voltammetry is most likely the result of a harmonic distortion due to the nonlinear response of the electrochemical cell; see Yap, *J. of Electroanalytical Chem.* 454:33 (1998); hereby incorporated by reference. Thus, any techniques that increase this non-linearity are desirable. In an embodiment, techniques are used to increase the higher harmonic signals; thus, frequency and phase-sensitive lock-in detection is performed at both the fundamental frequency of the applied waveform and also at multiples of the fundamental frequency (e.g. the higher harmonics) or just one. Since the background capacitance responds relatively linearly to AC signals (a sine wave input AC voltage results in a relatively nondistorted sine wave output), very little upper harmonic current is produced in the background. This gives a dramatic increase in the signal to noise ratio. Thus, detection at the higher harmonic frequencies, particularly the third, fourth and fifth harmonics (although the harmonics from second to tenth or greater can also be used) is shown to result in dramatic suppression of the background currents associated with non-Faradaic processes (like double layer charging) that can overwhelm the signal from the target molecules. In this way, the evaluation of the system at higher harmonic frequencies and phases can lead to significant improvements in the detection limits and clarity of signal. However, in some embodiments, the analysis of higher harmonics is not desired.

Thus, In an embodiment, one method of increasing the non-linear harmonic response is to increase or vary the amplitude of the AC perturbation, although this may also be used in monitoring the fundamental frequency as well. Without being bound by theory, it appears that increasing the amplitude increases the driving force nonlinearly. Thus, generally, the same system gives an improved response (e.g. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In an embodiment, measurements of the system are taken at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In an embodiment, harmonic square wave AC voltage is used; see Baranski et al., *J. Electroanal. Chem.* 373:157 (1994), incorporated herein by reference, although in some embodiments this is not preferred. This gives several potential advantages. For example, square waves are easier to create digitally and the pulse shape of the square wave can allow for better discrimination against charging capacitance. In sinusoidal harmonic AC voltammetry, harmonic signals provide better signal to background since faradaic response can be more nonlinear than charging capacitance. The same concept applies to SW harmonic AC voltage. The key difference between the two techniques is the frequency spectrum of the AC waveform. A singular frequency sinusoidal waveform contains just the fundamental frequency whereas a singular square wave contains the fundamental frequency as well as all odd harmonics. The technique looks at the even harmonics where the ratio of faradaic current to capacitance current is enhanced. All the odd harmonics have single AC voltage peaks while all the even harmonics have double AC voltage peaks. This is opposite to the case of sinusoidal harmonic AC voltage of a system that has a non-reversible redox couple.

In an embodiment, multiple frequency AC voltage is used. The idea is to create a waveform consisting of multiple frequencies with the same amplitude or different amplitudes to excite an electrochemical cell in an AC voltage fashion. The method benefits from fast Fourier transform or joint time-frequency transform to analyze the cell response. A JTFT spectrogram of a multiple frequencies AC voltage provides information on the driven (or fundamental) frequencies as well as their harmonic components. Some possible data analyses are: 1) comparison of response of fundamental frequencies, 2) comparison of all harmonic frequencies, 3) comparison of the response of one particular harmonic frequency of all excited frequencies, and 4) all analyses possible by standard single frequency AC voltage.

Accordingly, In an embodiment, a fast Fourier transform is done, as is generally outlined in the examples. Fourier transform analysis is a method for improving signal to noise and isolating desired signals when sinusoidal electrochemistry is done. Typical AC techniques rely on measurements of the primary frequency only. With sinusoidal voltammetry (and other inputs) observation at higher harmonics allows discrimination of signals primarily based on kinetics. For example, both fast and slow redox events would give similar peaks (provided the AC frequency was not too high) at the primary frequency. However, at higher harmonics, some redox molecules would generate signals while others would not. Using FFT analysis, all the various frequency components of a response to a sinusoidal input can be observed at once.

Similarly, in an embodiment, a joint time-frequency transform (JTFT) is done.

In an embodiment, digital lock-in techniques are used. In the past, digitized raw data from the electrochemical cell have been analyzed by either fast Fourier transform or some complex form of joint time-frequency transform analysis. The major drawback of these methods is the enormous computational time associated with frequency transformation techniques. Digital lock-in, on the other hand, is simple and fast. In principle, digital lock-in is identical to analog lock-in. In the former case, the bandwidth narrowing process is done mathematically by multiplying the cell response by a sinusoidal with the same frequency as the input voltage, but with 90 phase shift. The technique has the same limitation as its analog counterpart since only one frequency can be analyzed at a time. However, unlike analog lock-in, other frequencies can also be analyzed sequentially (or in parallel with a more powerful processor) since the raw data is archived. For an input voltage of $$V_{in} = E_{dc} + rt + E_{ac} \sin(\omega t) \tag{1}$$

the cell's response is essentially $$I(t) = \sum_n I_n(v)\mathrm{Sin}(n\omega t - \phi_n) = \sum_n I'_n(v)\mathrm{Sin}(n\omega t) - I''_n(v)\mathrm{Cos}(n\omega t) \quad (2)$$

To find the voltage dependent coefficients $I_n$ for the frequency ($n_0$ w) we multiply the response by 2 Sin($\_n_0$ t) and $-2$ Cos($\_n_0$ t) and apply a low pass filter to get the real and imaginary components. The low pass filtering used in this example is a simple moving average. Mathematically, the process is expressed as $$\frac{1}{t1-t0}\int_{t0}^{t1}\left(\sum_n I'_n(v)\mathrm{Sin}(n\omega t) - I''_n(v)\mathrm{Cos}(n\omega t)\right)2\mathrm{Sin}(wn_0 t)dt = \quad (3)$$

$$\left.\frac{I'_n(v)}{t1-t0}\left(t - \frac{\mathrm{Sin}(2n_0\omega t)}{2}\right)\right|_{t1,t0} = I'_n(v),$$

for $$t_1 - t_0 \gg T$$

In an embodiment, background subtraction of the current vector and phase optimization is done.

In an embodiment, correlation and/or convolution techniques are used. In this embodiment, many scans of the same electrode. Rather than looking for a peak in a single scan, many scans are viewed and a common correlation between the scans. For instance, it is possible that a bump in the noise appears near 180 mV for a negative, even if no ferrocene is present. However, it is unlikely that the same bump will appear in the same place if the frequencies are scanned. Thus, embodiments take scans at many frequencies and only count a positive if a peak occurs in all of them. This is a very simple correlation; more complex correlations may be done as well.

In an embodiment, signal recovery is done using signal recognition and background subtraction. In this embodiment, the idea is to fit the cell response to two summed functions, one that describes the signal and the other that models the background capacitive current. Once the functions are constructed, the signal is easily recovered from the response by subtracting the fitted background capacitive current. This signal recognition scheme is applicable to any system where the signal has a behavior and shape that is relatively well known.

The response from an electrochemical cell can be processed with a lock-in amplifier or equivalent bandwidth-narrowing technique. This is one of many methods of increasing signal to background using some form of bandwidth-narrowing technique.

In an embodiment, spectral analysis of the signal is done. In this embodiment, filtering techniques in the frequency domain make use of means, variances, densities, autocorrelation functions, and power spectral densities of the signal and apply it to the present systems to enhance the signal to noise ratio (see Schwartz et al., Signal Processing: Discrete Spectral Analysis, Detection, and Estimation, N.Y. McGraw Hill, 1975, hereby incorporated by reference).

In an embodiment, digital filtering techniques are used. These include, but are not limited to, match filter, Weiner filtering, Kalman, Finite Impulse Response, infinite impulse response, narrow band filtering, etc.

In an embodiment, a match filter is used; see Ziemer et al., "Principles of Communication Systems, Modulation and Noise", 4th Ed. John Wiley & Sons Inc., New York, 465-471, 1988; and Helstrom, C. W., "Statistical Theory of Signal Detection", Pergamon Press, Oxford, 112-115, 1968, both of which are incorporated by reference. In its simplest form, a match filter is a signal processing technique that "weights" the measured response (signal plus noise) samples by some corresponding known signal amplitude and convolutes the two signals to enhance signal to noise.

In an embodiment, a Weiner filter is used (see Press, supra; and Elliot et al., Fast Transforms: Algorithm, Analysis, Applications N.Y. Academic Press (1982), both of which are incorporated by reference). Weiner filtering involves finding an optimal filter that removes noise or background from the "corrupted" signal. This signal processing method works in conjunction with Fourier transform techniques. The idea is as follows. Due to poor signal to noise or a large background, the output from the instrument is a "corrupted" signal $$c(t)=s(t)+n(t)$$

where s(t) is the signal and n(t) is the noise. Note that s(t) is not the desired signal, it is composed of the true uncorrupted signal u(t) convolved with some known response function r(t) (In the case of the CMS system with a redox couple, u(t) is the Nernstian). In other words, $$s(t)=\int_{-\infty}^{\infty} r(t-\tau)u(\tau)d\tau.$$

In frequency space, the relation is $$S(\omega)=R(\omega)U(\omega)$$

where S, R, and U are the Fourier transform of s, r, and u, respectively. The uncorrupted signal can be recovered by finding the optimal filter $\varphi(t)$ or its Fourier counterpart $\Phi(\omega)$ which when applied to the measured signal c(t) or C($\omega$), and then deconvolved by r(t) or R($\omega$), produces a signal that approximates the uncorrupted signal u(t) or U($\omega$) with $$U(\omega) = \frac{C(\omega)\Phi(\omega)}{R(\omega)}.$$

In general the optimal filter is defined as $$\Phi(\omega) = \frac{|S(\omega)|^2}{|S(\omega)|^2 + |N(\omega)|^2}.$$

In an embodiment, a Kalman filter is used, which is a recursive-estimation filtering technique that tracks the current value of a changing signal in the presence of noise. See Kalman et al., A New Approach to Linear Filtering and Prediction Problems, Trans. ASME J. Basic Engineering, Series D, 82, Mar. 35, 1960; Elliot Ed. Handbook of Digital Signal Processing: Engineering Applications," Academic Press, San Diego, p 908, 1987; Chui et al., Kalman Filtering: with Real Time Applications", Springer-Verlag, New York, 1987; all of which are expressly incorporated by reference.

In an embodiment, the non-linear harmonic response is increased by inducing an asymmetrical response. In an embodiment, this is done by using a system that has a non-reversible redox couple. For example, ferrocene is a redox couple that is very reversible. Thus, the ferrocenes subtended by the ac voltage at a given point, get oxidized on the upswing of the ac voltage and reduced on the down swing. However, if a semi-reversible or non-reversible redox couple is used, for example, the molecule will get oxidized on the upswing and not reduced (or a portion) on the downswing; or vice versa. This will produce even greater non-linearities at certain frequencies.

Three examples of ways to perform this are: use an ETM molecule that gets degraded in the oxidized form, like luminol, use co-reduction or redox mediation, and use enzyme coupled mediation, as generally described in WO00/16089.

In an embodiment, electron transfer is initiated using alternating current (AC) methods. In addition, the use of AC techniques allows the significant reduction of background signals at any single frequency due to entities other than the ETMs, e.g. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, e.g. have partial or insufficient monolayers, e.g. where the solvent is accessible to the electrode. As outlined above, in DC techniques, the presence of "holes" where the electrode is accessible to the solvent can result in solvent charge carriers "short circuiting" the system, e.g. they reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In an embodiment, measurements of the system are taken at least two separate frequencies, with measurements at a plurality of frequencies being preferred. A plurality of frequencies includes a scan. For example, measuring the output signal, e.g., the AC current, at a low input frequency such as 1-20 Hz, and comparing the response to the output signal at high frequency such as 10-100 kHz will show a frequency response difference between the presence and absence of the ETM. In an embodiment, the frequency response is determined at at least two, preferably at least about five, and more preferably at least about ten frequencies.

Output Signal

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In an embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In an embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In an embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not affect the bulk impedance, and vice versa. Thus, the assay complexes comprising the nucleic acids in this system have certain faradaic impedance that will depend on the distance between the ETM and the electrode, their electronic properties, and the composition of the intervening medium, among other things. Of importance in the methods of the invention is that the faradaic impedance between the ETM and the electrode is significantly different depending on whether the label probes containing the ETMs are specifically or non-specifically bound to the electrode.

Accordingly, the present invention further provides electronic devices or apparatus for the detection of analytes using the compositions of the invention. The apparatus includes a test chamber for receiving a sample solution which has at least a first measuring or sample electrode, and a second measuring or counter electrode. Three electrode systems are also useful. The first and second measuring electrodes are in contact with a test sample receiving region, such that in the presence of a liquid test sample, the two electrophoresis electrodes may be in electrical contact.

In an embodiment, the apparatus also includes detection electrodes comprising a single stranded nucleic acid capture probe covalently attached via an attachment linker, and a monolayer, such as are described herein.

The apparatus further comprises an AC voltage source electrically connected to the test chamber; that is, to the measuring electrodes. Preferably, the AC voltage source is capable of delivering DC offset voltage as well.

In an embodiment, the apparatus further comprises a processor capable of comparing the input signal and the output signal. The processor is coupled to the electrodes and configured to receive an output signal, and thus detect the presence of the target nucleic acid.

EXAMPLES

The methods and compositions described are further illustrated in the following example, which is provided by way of illustration and is not intended to be limiting.

Example 1: Implementation of Electrode Initialization

Figure 4:
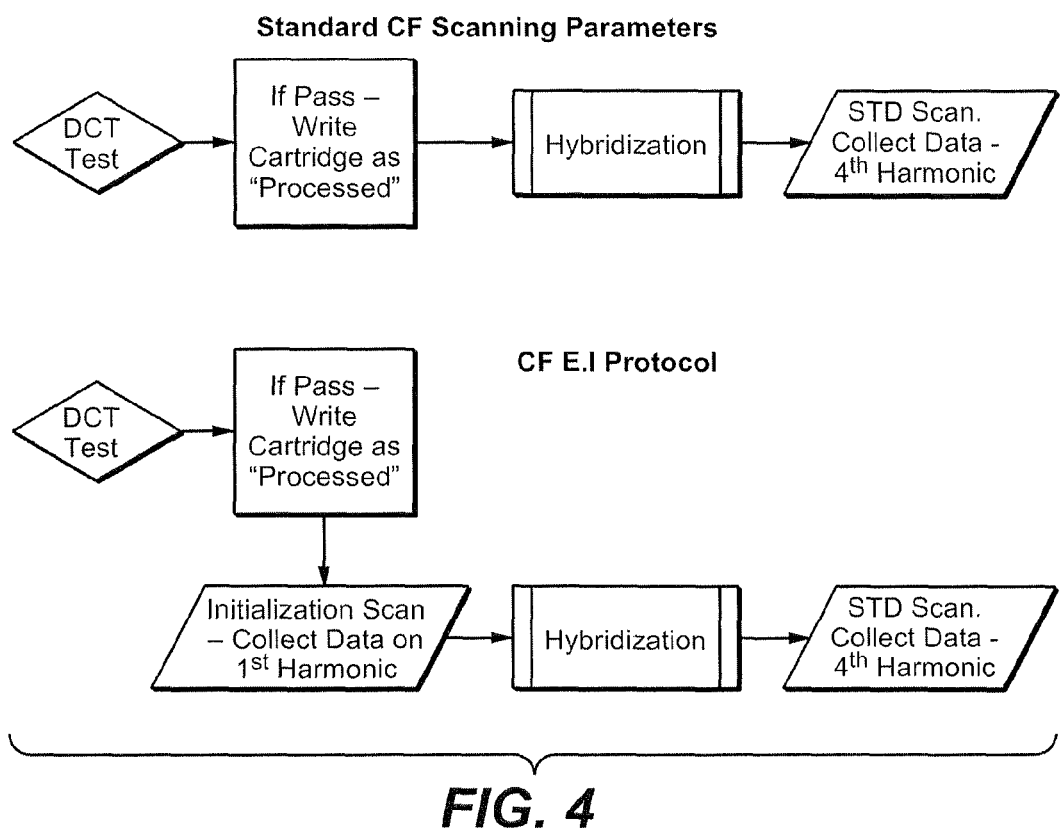
FIG. 4 illustrates an overview of the electrode initialization protocol described by the present invention.

Implementation of electrode initialization (EI) was performed to validate that EI resolves the following failure modes: $E_0$ shifting, score shifting, and low signal miscalls. EI treats a self-assembled monolayer (SAM) by combating non-specific binding of free-floating electron transfer moiety (ETM) probes. EI was tested against a standard cystic fibrosis protocol (FIG. 4). The validation study further demonstrated that implementation of EI does not negatively impact the ability of an assay to call wild-type, heterozygous, and mutant genotypes.

Methods

An eSensor®CF Genotyping Test was used for determining the genotyping status of a defined panel of CF mutations. Purified genomic DNA was isolated from the patient specimen. The eSensor® Cystic Fibrosis Genotyping Test generated single stranded target DNA from the genomic DNA by multiplex PCR amplification followed by exonuclease digestion. The specimen was combined with a signal buffer containing a pair of allele-specific oligonucleotide signal probes for each polymorphism, where each pair of signal probes was labeled with a genotype-specific ferrocene derivative. The mixture of amplified sample and signal buffer was loaded onto a cartridge containing single stranded oligonucleotide capture probes bound to gold-plated electrodes. The cartridge was inserted into an XT-8 instrument where the single stranded targets hybridized to the complementary sequences of the capture probes and signal probes.

The ferrocene label was detected at the electrode surface using voltammetry. The resulting current was interpreted by the XT-8 system and reporting software to evaluate signal strength and genotyping score. The combined major allele and minor allele current (signal) generated for each electrode was evaluated against a pre-established signal threshold.

Upon startup of the XT-8 cartridge, all probes diffused toward the SAM, creating non-specific signal and variable signal potentials. By applying a short scan to the cartridge post initial wetting, the voltage pulses all non-specific probes away from the monolayer and prevents non-specific signal and current potential variability, leaving a specific signal for the detection portion of signal scanning.

Twenty (20) Coriell and five (5) MMQCI control samples (Table 1) were tested that represent wild-type (RM005172: Control E_CF.WT) and all heterozygous and/or mutant genotypes included in a GenMark CF panel. In addition, three (3) wild-type and three (3) representative heterozygous patient genomic DNA samples (delF508, G542X, and R117H) were tested. One sample previously demonstrated to result in a high level of 1717-1G>A (see Table 3) low signal calls will be tested in quadruplicate. Table 1 summarizes each of the samples used in addition to the mutation(s) that each sample represents.

TABLE 1

Samples used for EI Coriell Controls

| Sample | Vendor ID | Genotype | Final Concentration (ng/ul) |
|---|---|---|---|
| 1 | NA12444 | 1717 − 1G > A; 7T/7T | 2 |
| 2 | NA18800 | 1898 + 1G > A; delF508; 7T/9T | 2 |
| 3 | NA18799 | 2184delA; delF508; 7T/9T | 32 |
| 4 | NA11859 | 2789 + 5G > A; 7T/7T | 34 |
| 5 | NA07441 | 3120 + 1G > A; 621 + 1G > T; 7T/9T | 37 |
| 6 | NA11275 | 3659delC; delF508; 7T/9T | 22 |
| 7 | NA07381 | 3849 + 10KbC > T; delF508; 7T/9T | 24 |
| 8 | NA11282 | 621 + 1G > T; G85E; 7T/9T | 26 |
| 9 | NA11280 | 711 + 1G > T; 621 + 1G > T; 7T/9T | 34 |
| 10 | NA11290 | A455E; 621 + 1G > T; 9T/9T | 27 |
| 11 | NA11277 | delI507; 7T/7T | 28 |
| 12 | NA11497 | G542X; 7T/9T | 25 |
| 13 | NA12785 | G551D; R347P; 7T/7T | 22 |
| 14 | NA11472 | N1303K; 7T/9T | 23 |
| 15 | NA12585 | R1162X; 7T/7T | 24 |
| 16 | NA13591 | R117H; delF508; 5T/9T | 24 |
| 17 | NA12960 | R334W; 7T/7T | 24 |
| 18 | NA11761 | R553X; G551D; 7T/7T | 22 |
| 19 | NA11284 | R560T; delF508; 7T/9T | 100 |
| 20 | NA11723 | W1282X; 5T/7T | 100 |

TABLE 2

MMQCI controls
MMQCI Controls

| RM002182: Control C_CF.HET1 | RM002183: Control D_CF.HET2 | RM002180: Control A_CF.MUT1 | RM002181: Control B_CF.MUT2 |
|---|---|---|---|
| 1717 − 1G > A | DeltaI507 | 1717 − 1G > A | DeltaI507 |
| 1898 + 1G > A | R553X | 1898 + 1G > A | R553X |
| 2184delA | R117H | 2184delA* | R117H |
| 2789 + 5G > A | | 2789 + 5G > A | |
| 3120 + 1G > A | | 3120 + 1G > A | |
| 3659delC | | 3659delC | |
| 3849 + 10KbC > T | | 3849 + 10KbC > T | |
| 621 + 1G > T | | 621 + 1G > T | |
| 711 + 1G > T | | 711 + 1G > T | |
| A455E | | A455E* | |
| delF508 | | delF508 | |
| G542X | | G542X | |
| G551D | | G551D | |
| G85E | | G85E | |
| N1303K | | N1303K | |
| R1162X | | R1162X | |
| R334W | | R334W | |
| R347P | | R347P | |
| R560T | | R560T | |
| W1282X | | W1282X | |

*Indeterminate scores and/or HET calls are expected for the 2184delA and A455E MUT controls

TABLE 3

Three wild-type and three heterozygous patient samples used.

| Sample ID | Expected Genotype | Concentration (ng/uL) |
|---|---|---|
| MG-700623426 | R117H HET (7T/7T) | 22.37 |
| AM-717863126 | delF508 HET | 43.82 |
| BH-725923126 | G542X HET | 16.65 |
| MW-39031926 | WT | 19.84 |
| RH-95123626 | WT | 29.2 |
| AS-88591326 | WT | 20.02 |

TABLE 4

Lots used in EI validation protocol.

| Cartridge lot (KT020657) | Mfg. Date | Recorded failure modes | # Cartrs. | Group |
|---|---|---|---|---|
| 51327024 | Sep. 1, 2010 | 1717 − 1G > A low signal, 1717 − 1G > A indeterminate scores | 16 | Baseline 1 |
| 51399824 | Jul. 6, 2011 | 1898 + 1G > A/621 + 1G > T/W1282X indeterminate scores due to score shifting | 40 | Baseline 1 |
| 51356860 | Aug. 6, 2011 | 1898 + 1G > A/W1282X indeterminate scores due to score shifting | 16 | Baseline 1 |
| 51521135 | Aug. 31, 2011 | R334W false HET due to score shifting | 24 | Baseline 2 |
| 51414271 | Sep. 8, 2011 | 3120 + 1G > A/3659delC indeterminate scores due to score shifting | 32 | Baseline 2 |
| 51526996 | Oct. 10, 2011 | 2184delA indeterminate score due to score shifting | 16 | Baseline 2 |
| 51554366 | Jun. 15, 2012 | 1717 − 1G > A low signal | 36 | Recently Mfg. 1 |
| 51589222 | Jul. 9, 2012 | N/A | 36 | Recently Mfg. 2 |

Samples were run using two different software protocols: 1) the current Genmark Dx CF protocol: CF on XT-8 IVD; and 2) Assay software incorporating electrode initialization (−150 to +750 mV in 5 s): CF on XT-8 IVD (10)

Implementation of electrode initialization through the proposed software update did not change any physical characteristic of the product or the recommended concentration of input DNA. The acceptable range of DNA input into the assay (2-100 ng/ul) is due to limitations of PCR amplification, which will not be impacted by the software update. However, two Coriell samples were used at 2 ng/ul and two were used at 100 ng/ul to demonstrate that the expected results were observed with DNA inputs at the high and low end of the acceptable range.

EI sought to address 2184delA discordant calls in a CF assay. The CF assay was affected by three unique failure modes, which in some cases can generate miscalls. The three failure modes are 1) EO shifting, 2) Score shifting, and 3) Low signal miscalls.

$E_0$ shifting—Due to variations in the reference electrode, the potential at which the ferrocene label oxidizes is shifted, resulting in a poor fit of the signal trace by the assay software. This results in no calls and, in some cases, miscalls.

Score shifting—Due to the presence of non-specific label which settles near the surface of the gold electrodes, the score (WT:MT signal) is shifted closer to an indeterminate boundary of the assay's calling parameters. This results in no calls and, in some cases, miscalls.

Low signal miscalls—Due to a poorly processed sample, signal can be generated which barely exceeds signal threshold, but is incorrectly fit due to the shape of the signal trace. This results in no calls and, in some cases, miscalls.

Material prone to the error modes outlined above (baseline lots) was tested to determine if the error modes are resolved when electrode initialization is utilized. Material less prone to the error modes outlined above (recently manufactured lots) was tested to ensure that expected wild-type, mutant, and heterozygote genotype calls are made with electrode initialization.

Samples were prepared as follows: MMQCI control samples were obtained from inventory and are ready for use in amplification. The majority of the Coriell control samples were diluted 1:10 in molecular grade water from the stock solutions (final concentration of ~25 ng/ul). Two Coriell samples were run at 2 ng/ul and two were run at 100 ng/ul to cover the recommended range of DNA input into the assay.

Thirty-two (32) samples were processed using the four (4) lots of cartridges outlined in Table 4. One negative control (DCM) sample was included, which contained water rather than input DNA. Baseline lots were processed using both the current software protocol, CF on XT-8 IVD, as well as CF assay software incorporating electrode initialization (−150 to +750 mV in 5 s), CF on XT-8 IVD. Recently manufactured lots were processed using only the CF assay software incorporating electrode initialization, CF on XT-8 IVD. The sample previously demonstrated to result in a high level of 1717-1G>A low signal errors was be run in quadruplicate, while all other samples were run as a single test for a total of 216 tests.

Figure 5A:
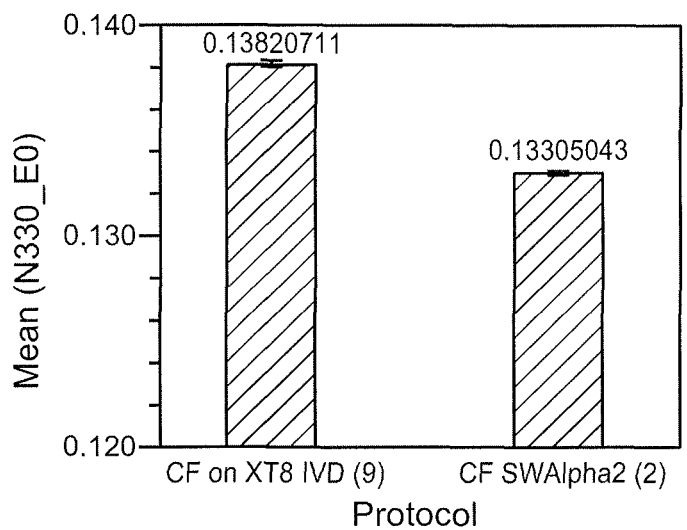
FIG. 5 illustrates that electrode initialization improves CF results relating to Eo shifting.
Figure 5B:
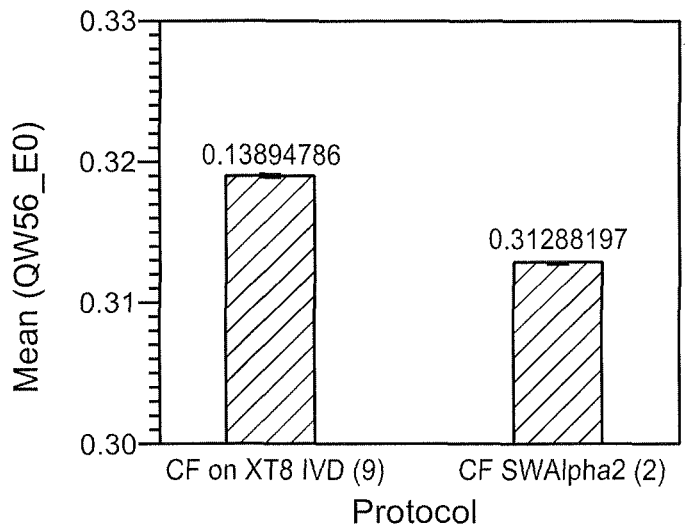

Results $E_0$ stability—Initialization reduced $E_0$ by 0.005V in N330 and by 0.006V in QW56 (FIG. 5). The differences were both significant, p<0.00001 by 2 sample t-test.

Figure 6:
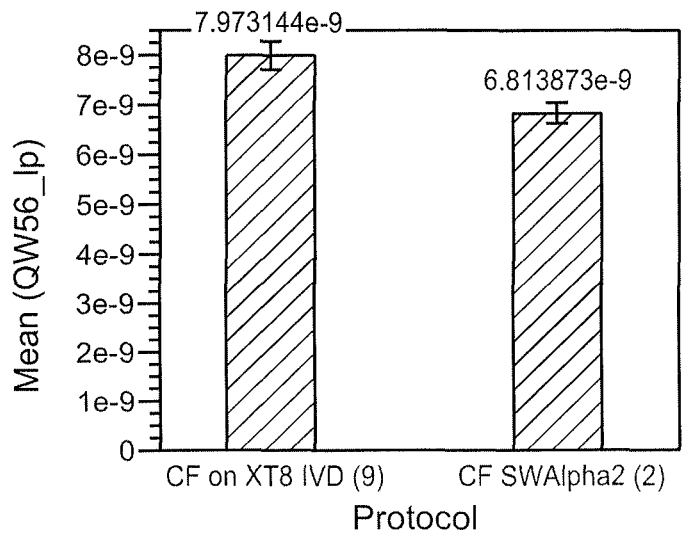
FIG. 6 illustrates that electrode initialization statistically improves CF results relating to score shifting.

Score shift—Initialization reduced background nonspecific QW56 signal by 15% (FIG. 6). The difference is significant, p<0.001 by 2 sample t-test.

Figure 7A:
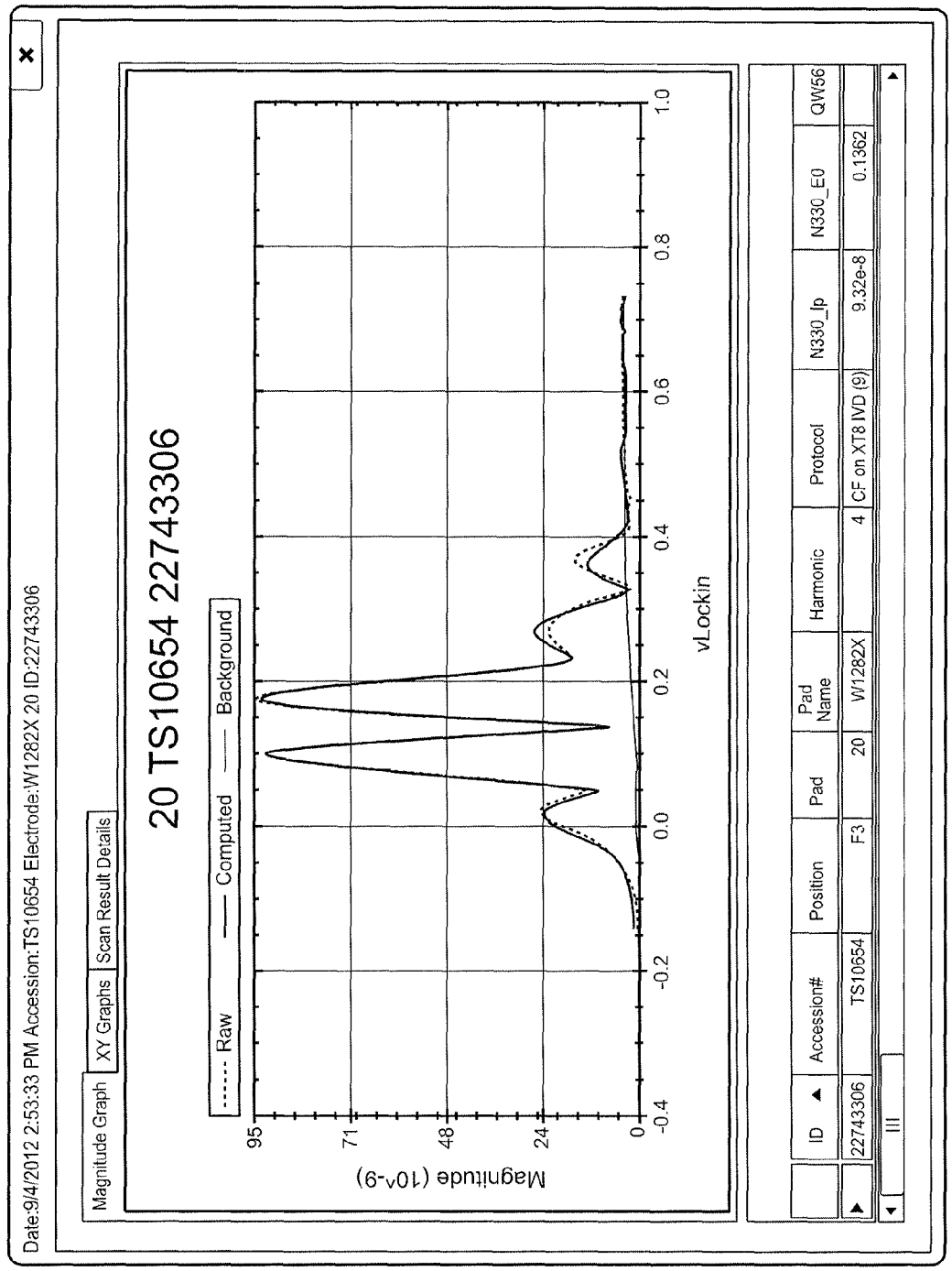
FIG. 7 illustrates that electrode initialization reduces low signal traces.
Figure 7B:
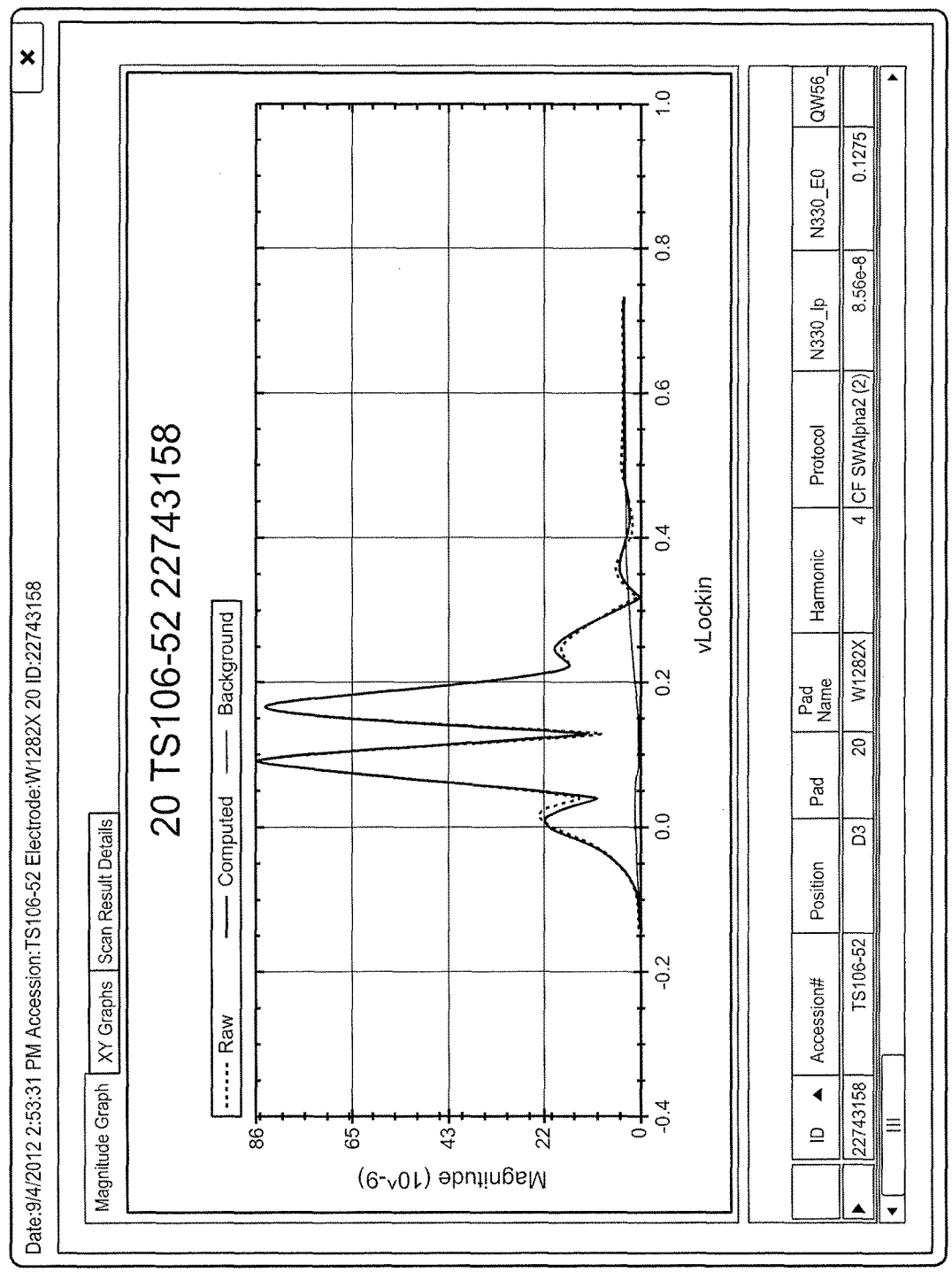
Figure 8A:
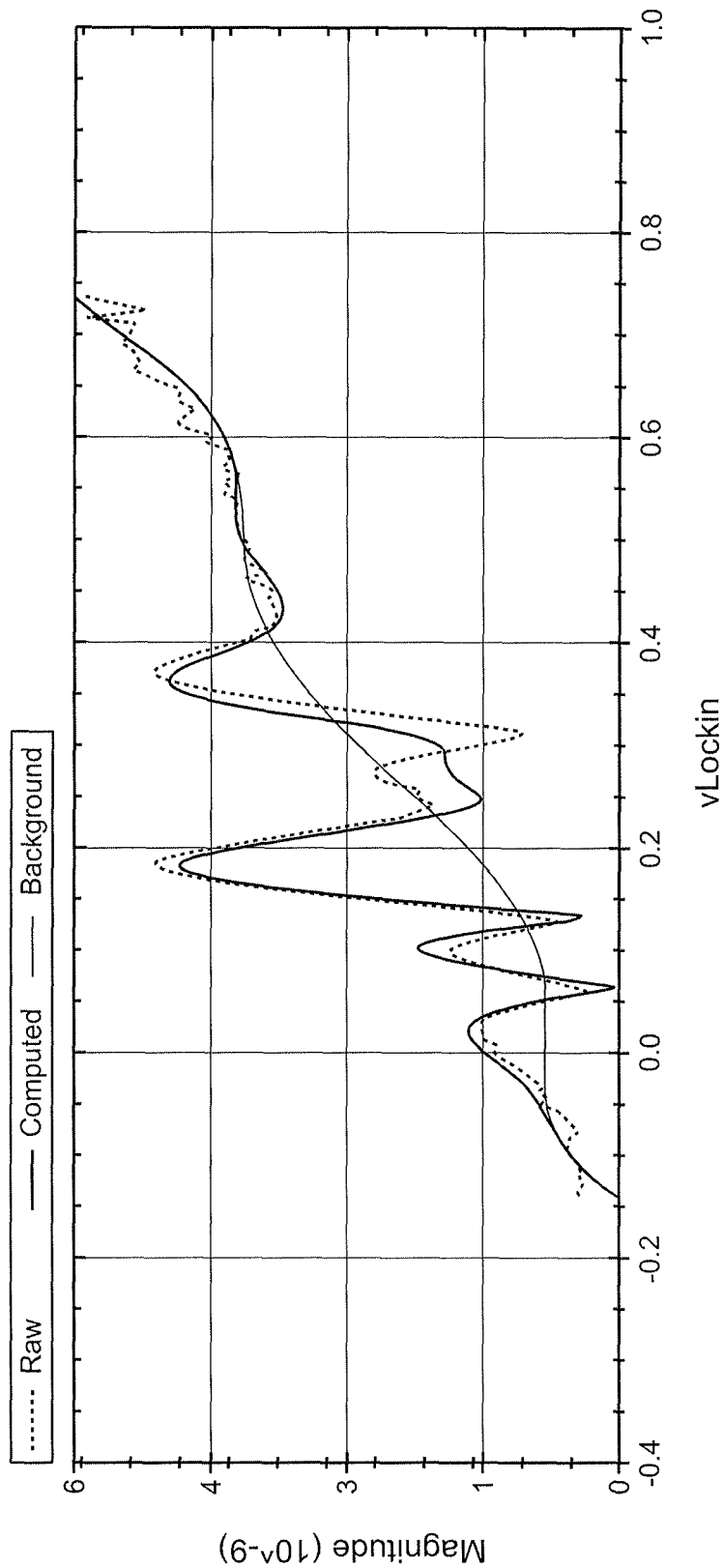
FIG. 8 illustrates false heterozygotes observed without electrode initialization.
Figure 8B:
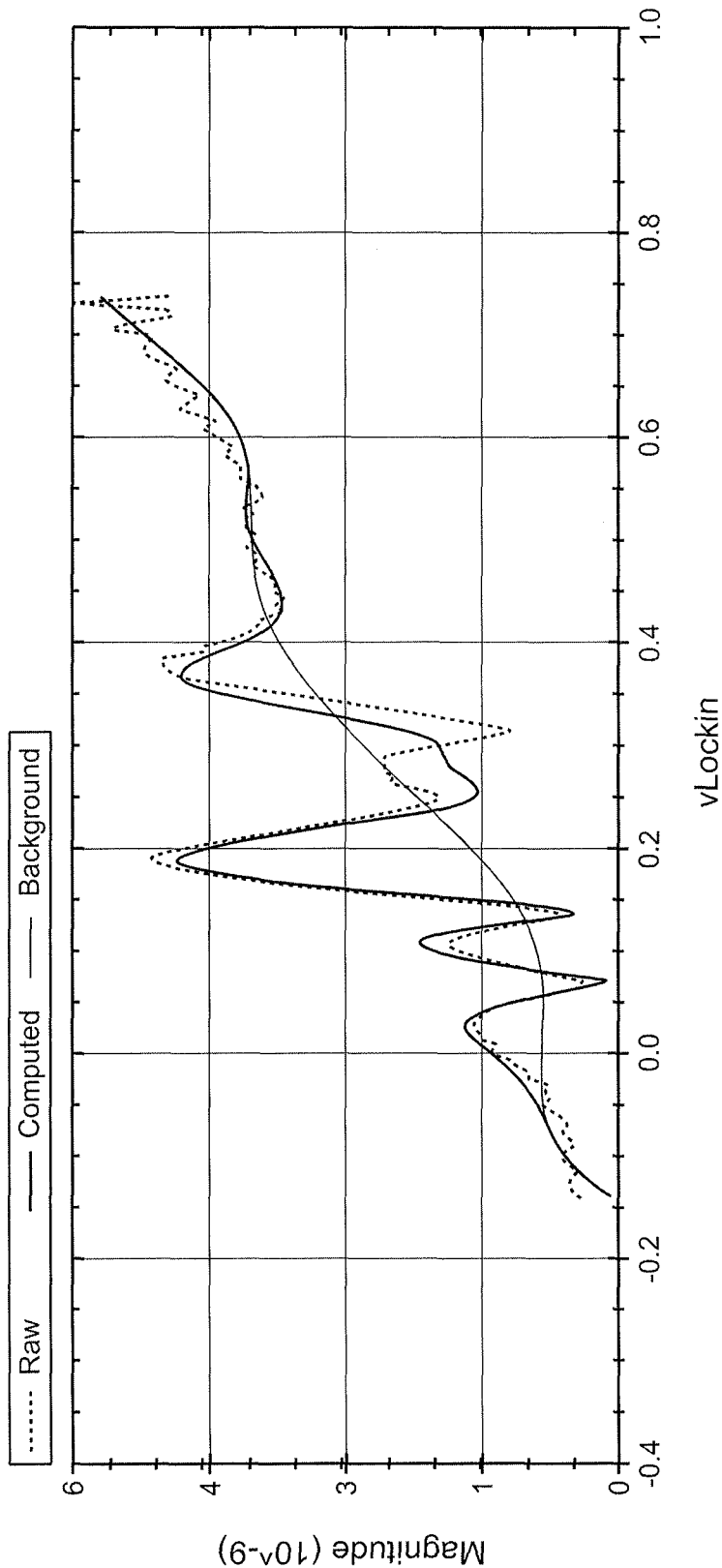
Figure 8C:
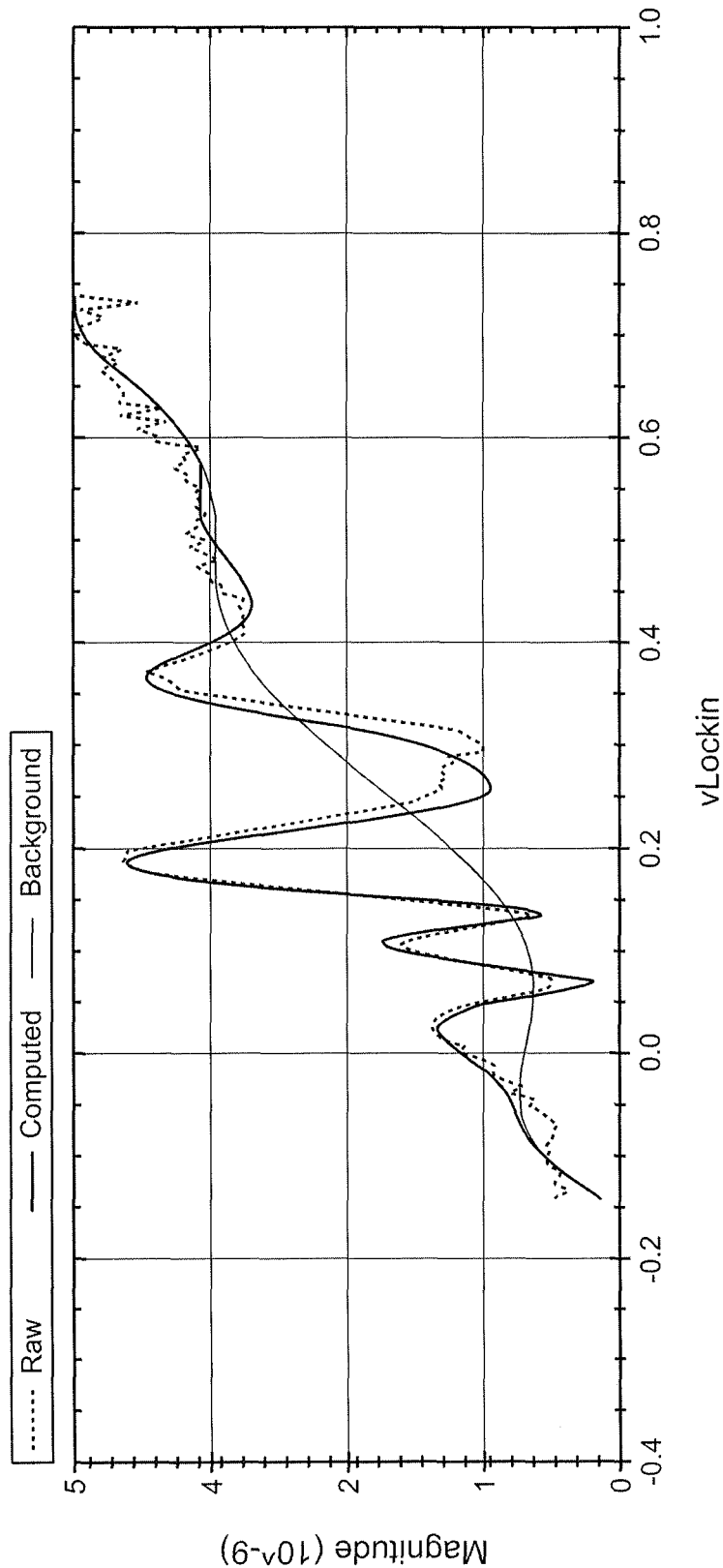
Figure 8D:
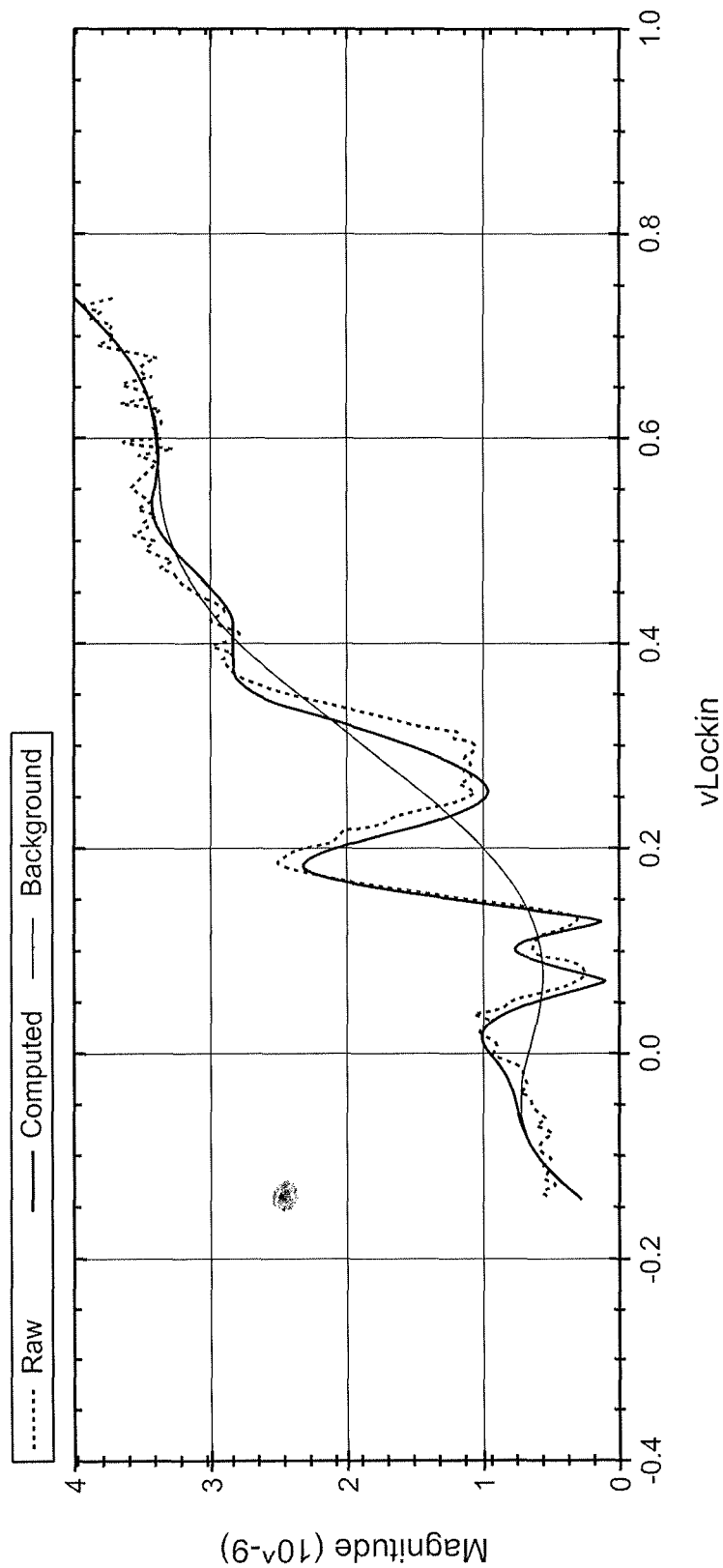
Figure 8E:
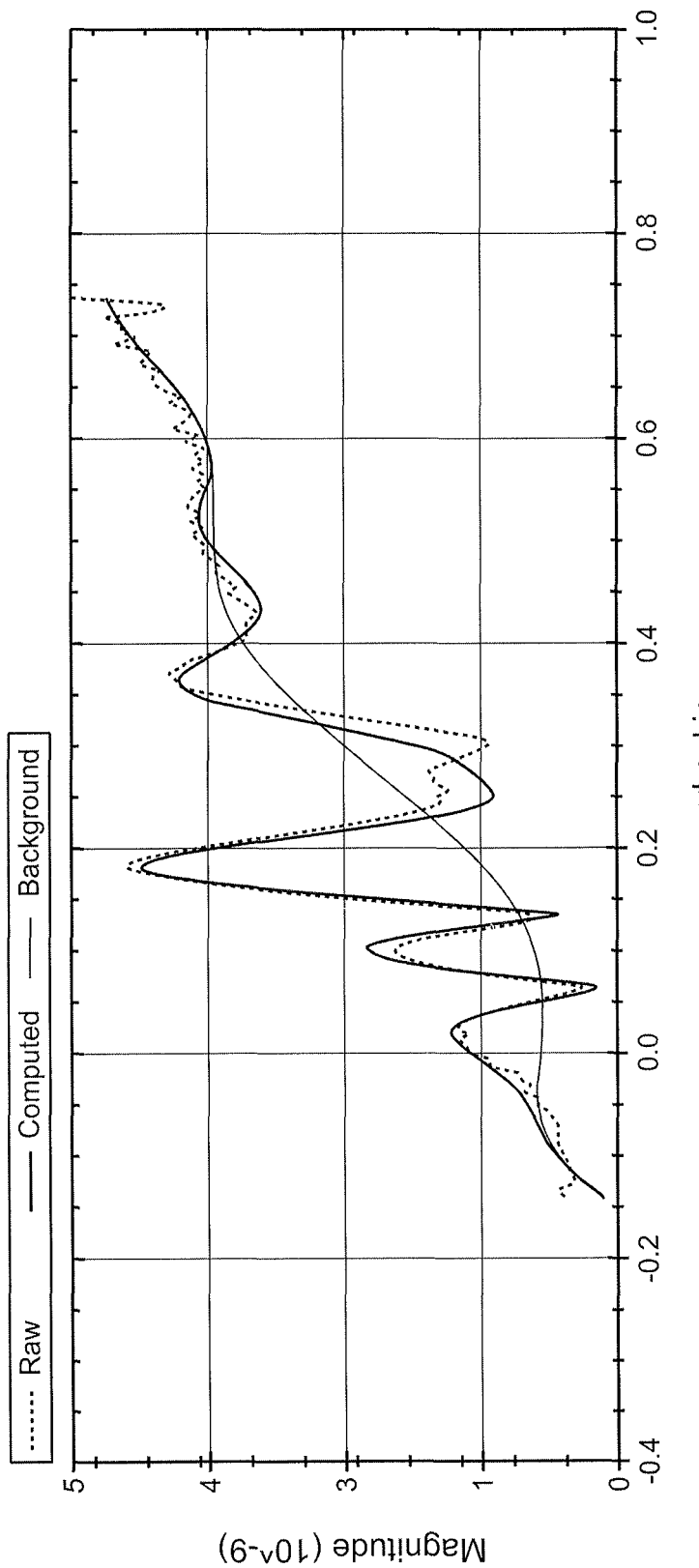
Figure 8F:
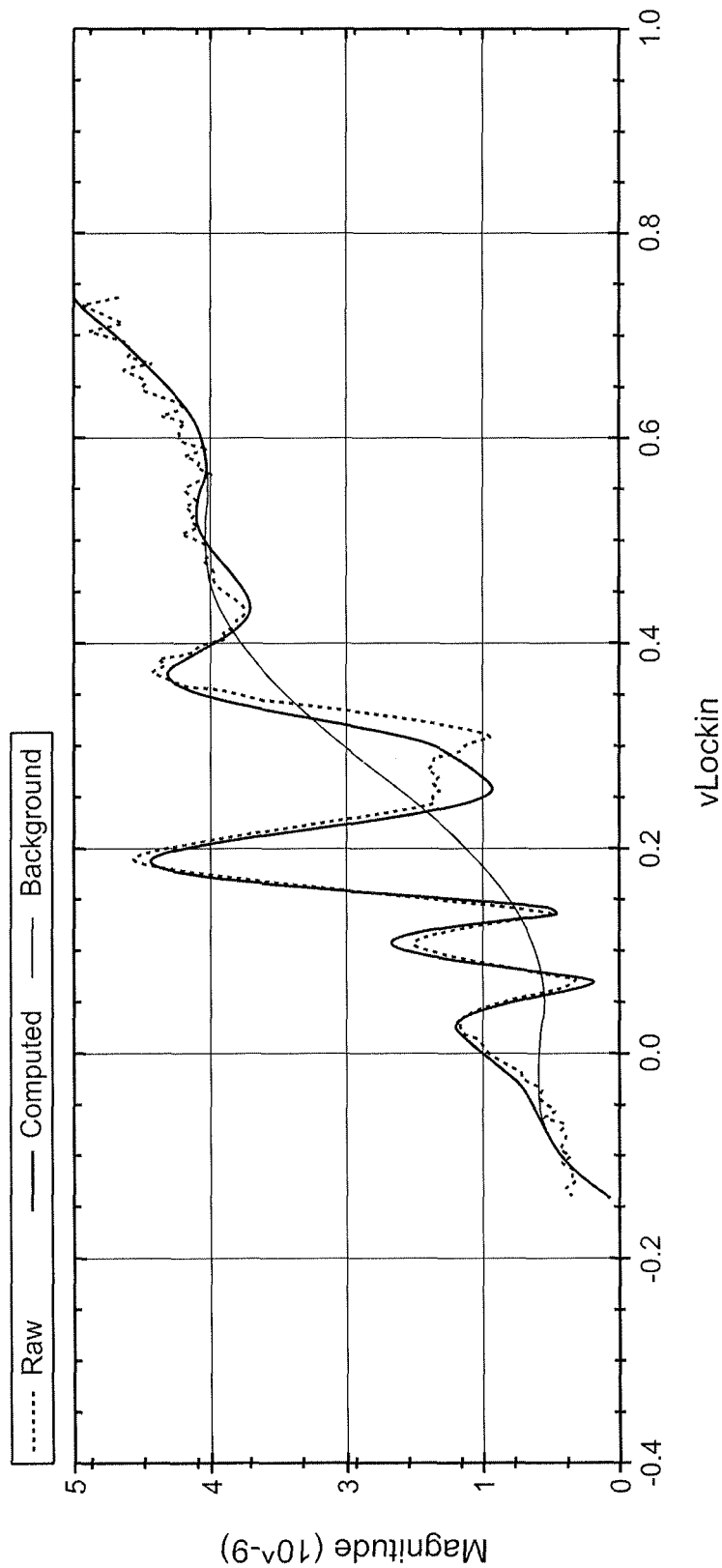
Figure 9A:
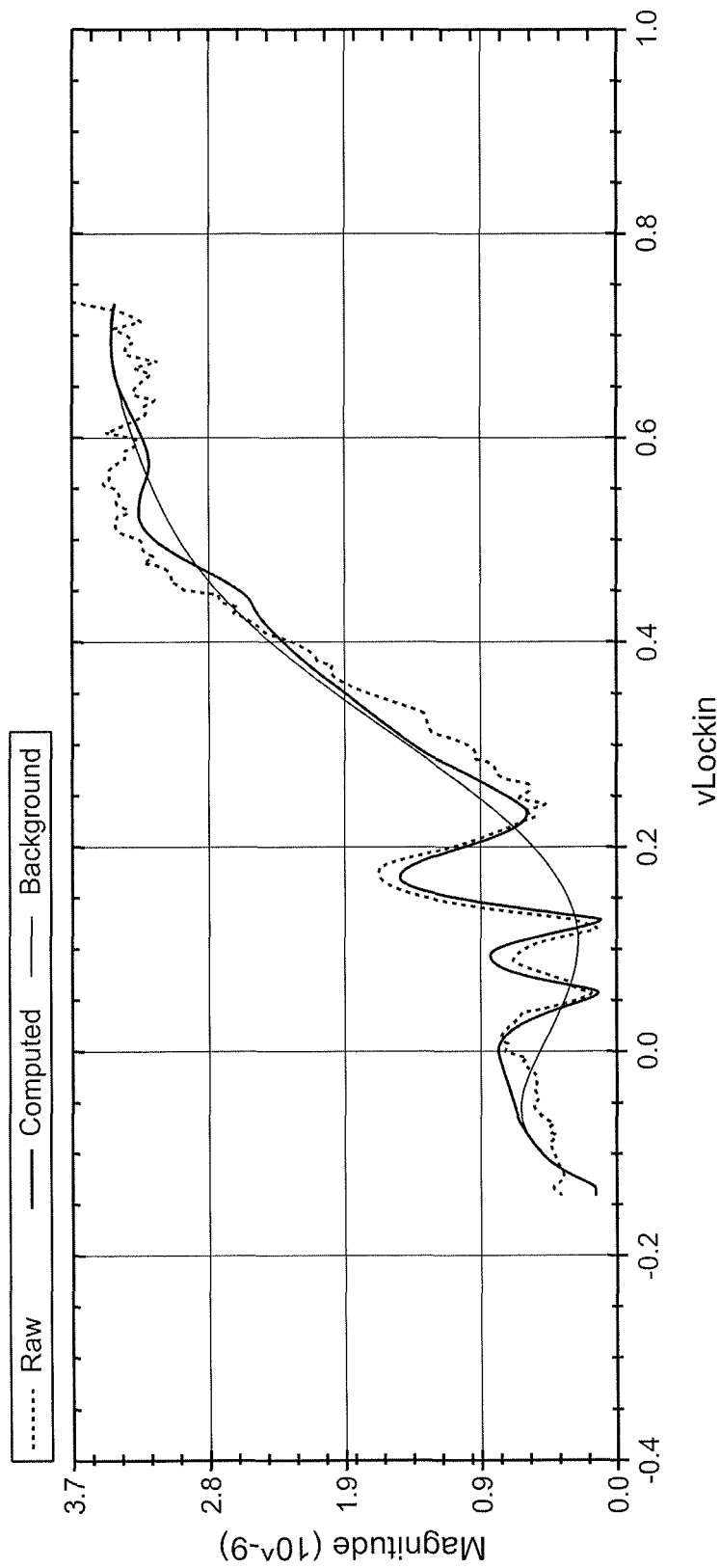
FIG. 9 illustrates that electrode initialization eliminates false heterozygotes.
Figure 9B:
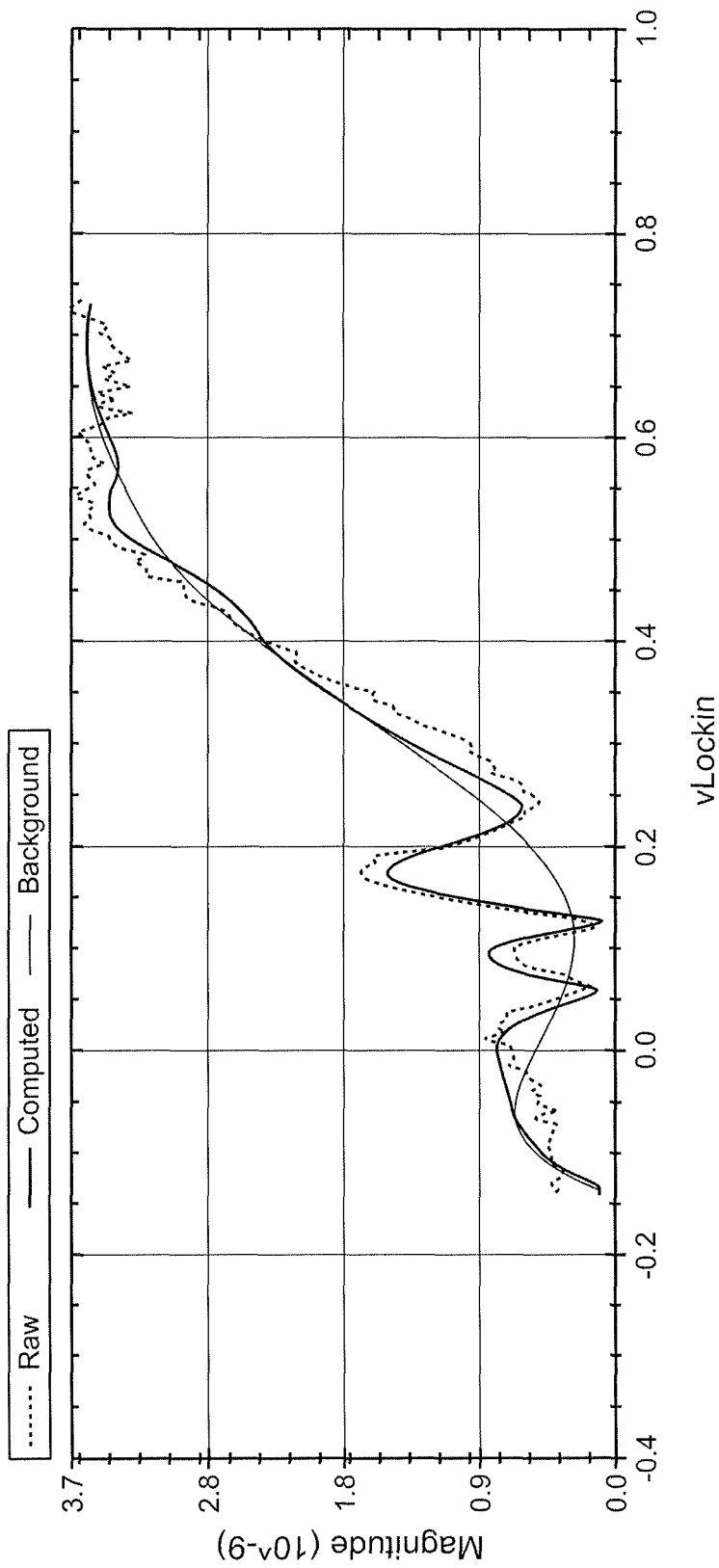
Figure 9C:
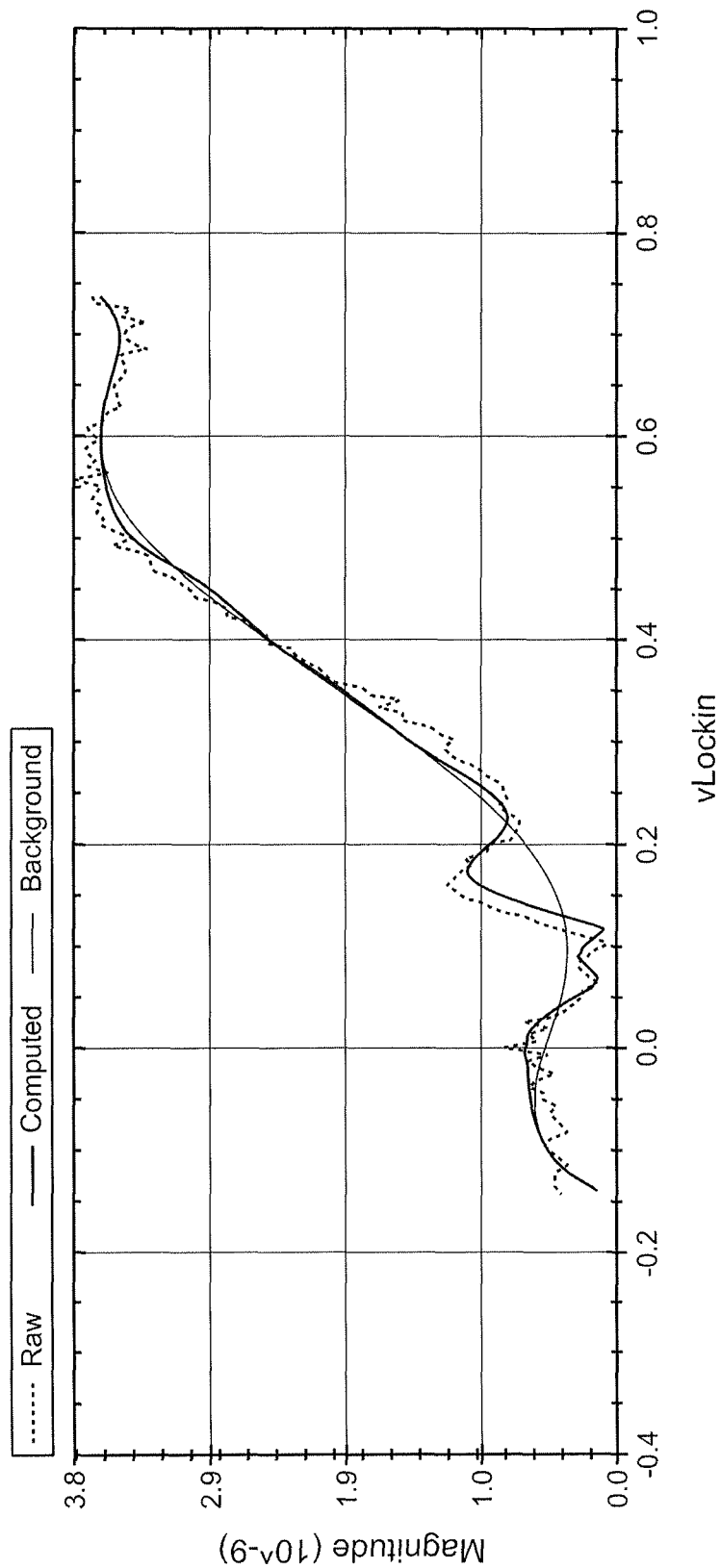
Figure 9D:
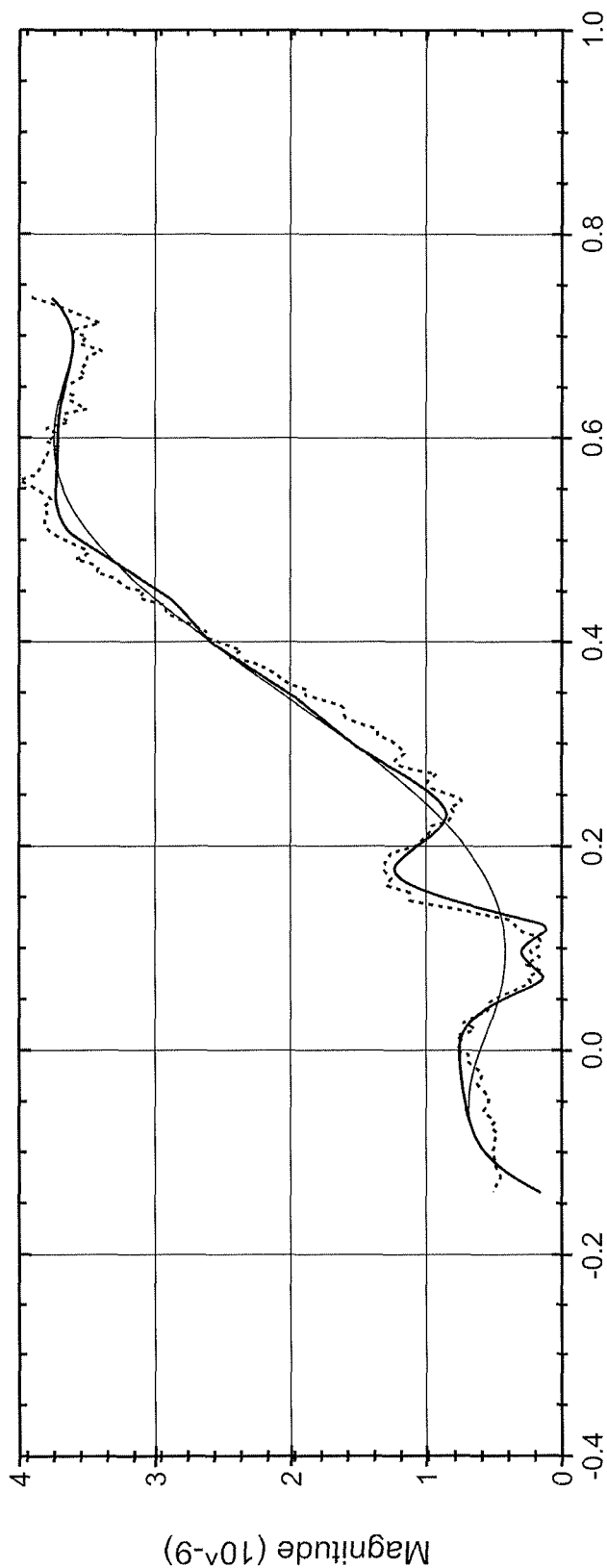

Low signal traces—No false hets with 1717 low (degraded) samples were observed (FIGS. 7, 8, and 9). In FIG. 7, initialization visually reduces a "5th bump" in the 4th harmonic signal. Similarly, in FIGS. 8 and 9, initialization visually reduced a "5th bump" in the 4th harmonic signal, which leads to false het calls in a sample previously demonstrated to result in a high level of 1717-1 G>A signal calls. Tables 5-8 summarize the sample results.

TABLE 5

Summary of patient sample results.

| | | Reported CF Mutation | |
|---|---|---|---|
| Patient Sample | Known CF Het Mutation | Old Protocol | Initialization Protocol |
| 1 | R117H HET | 3120 + aG > A indet, 3659delC indet, 3849 + 10kbC > T indet | ☑ |
| 2 | delF508 HET | 621 + 1G > T indet, R117H indet | ☑ |
| 3 | G542X HET | ☑ | ☑ |
| 4 | WT | 3120 + 1G > A indet | ☑ |
| 5 | WT | 3659delC indet, 3849 + 10kbC > T contradictory, 711 + 1G > T contradictory | ☑ |
| 6 | WT | ☑ | ☑ |

TABLE 6

Summary of MMQCI control sample results.

| MMQCI Control Sample | Known CF Het Mutation | Reported CF Mutation - Old Protocol | Reported CF Mutation - Initialization Protocol |
|---|---|---|---|
| 1 | WT | 3120 + 1G > A indet, 3659delC indet, 3849 + 10kbC > T indet | ✓ |
| 2 | HET for all detected mutations except: delI507, R553X, R117H | ✓ | ✓ |
| 3 | delI507 HET, R553X HET, R117H HET | 3120 + 1G > A contradictory | ✓ |
| 4 | MUT for all detected mutations except: delI507, R553X, R117H | ✓ | ✓ |
| 5 | delta 507 MUT, R553X MUT, R117H MUT | 5/7/9T indet | ✓ |

TABLE 7

Summary of Coriell control sample results.

| Coriell Control Sample | Known CF Het Mutation | Reported CF Mutation - Old Protocol | Reported CF Mutation - Initialization Protocol |
|---|---|---|---|
| 1 | 1717 − 1G > A; 7T/7T | 3894 + 10KbC > T indet | ✓ |
| 2 | 1898 + 1G > A; delF508; 7T/9T | ✓ | ✓ |
| 3 | 2184delA; delF508; 7T/7T | 3894 + 10KbC > T indet | ✓ |
| 4 | 2789 + 5G > A; 7T/7T | 1898 + 1G > A indet OR 3659 DelC indet, 3849 + 10KbC > T indet | ✓ |
| 5 | 3120 + 1G > A; 621 + 1G > T; 7T/9T | 3659delC indet | ✓ |
| 6 | 3659delC; delF508; 7T/9T | 3120 + 1G > A HET, 3849 + 10KbC > T HET | ✓ |
| 7 | 3849 + 10KbC > T; delF508; 7T/9T | 3659delC indet AND/OR 3120 + 1G > A indet | ✓ |
| 8 | 621 + 1G > T; G85E; 7T/9T | 3659delC indet AND 3849 + 10kbC > T indet | ✓ |
| 9 | 711 + 1G > T; 621 + 1G > T; 7T/9T | 711 + 1G > T HET; 621 + 1G > T HET; 3659delC HET | ✓ |
| 10 | A455E; 621 + 1G > T; 9T/9T | 3659delC indet | ✓ |
| 11 | delI507; 7T/7T | 3659delC indet | ✓ |
| 12 | G542X; 7T/9T | ✓ | ✓ |
| 13 | G551D; R347P; 7T/7T | ✓ | ✓ |
| 14 | N1303K; 7T/9T | 1898 + 1G > A indet | ✓ |
| 15 | R1162X; 7T/7T | A455E contradictory | ✓ |
| 16 | R117H; delF508; 5T/9T | 3659delC indet | ✓ |
| 17 | R334W; 7T/7T | R560T HET; delF508 HET; 3659delC HET; 7T/9T | ✓ |
| 18 | R553X; G551D; 7T/7T | ✓ | ✓ |
| 19 | R560T; delF508; 7T/9T | R560T HET; delF508 HET; 3659delC HET; 7T/9T | ✓ |
| 20 | W1282X; 5T/7T | 3659delC indet, 1898 + 1G > A indet | ✓ |

TABLE 8

Demonstrates failure rate of EI protocol to 0.01%

| Lot | QC Date | Field Protocol | Complaint Date Range | Total Kits Shipped | NSB | E0 | NSB/E0 Failure Rate |
|---|---|---|---|---|---|---|---|
| 51589255-51554348-51589254-51527012 51653007 | Apr. 12, 2012-Jun. 27, 2012 | CF (10) | Oct. 26, 2012-Jan. 03, 2013 (only 51653007) | 44 | 1 | 0 | 0.09% |
| 51554100-51651799 | Apr. 17, 2012 | CF (10) | Oct. 26, 2012-Jan. 03, 2013 (only 51651799) | 15 | 0 | 0 | 0.00% |
| 51589504 | Sep. 5, 2012 | CF (10) | Sep. 27, 2012-Dec. 14, 2012 | 29 | 0 | 0 | 0.00% |
| 51554098 | Oct. 18, 2012 | CF (10) | Nov. 26, 2012-Dec. 7, 2012 | 22 | 0 | 0 | 0.00% |
| 51554408 | Oct. 29, 2012 | CF (10) | Nov. 28, 2012-Jan. 09, 2013 | 81 | 0 | 0 | 0.00% |
| 51589506 | Nov. 20, 2012 | CF (10) | Dec. 20, 2012-Jan. 11, 2013 | 53 | 0 | 0 | 0.00% |
| 51589312 | Dec. 27, 2012 | CF (10) | N/A | 40 | 0 | 0 | 0.00% |
| Totals Protocol Results | | | | 284 | 1 | 0 | 0.01% |

Example 2: Electrode Initialization Times

Figure 10:
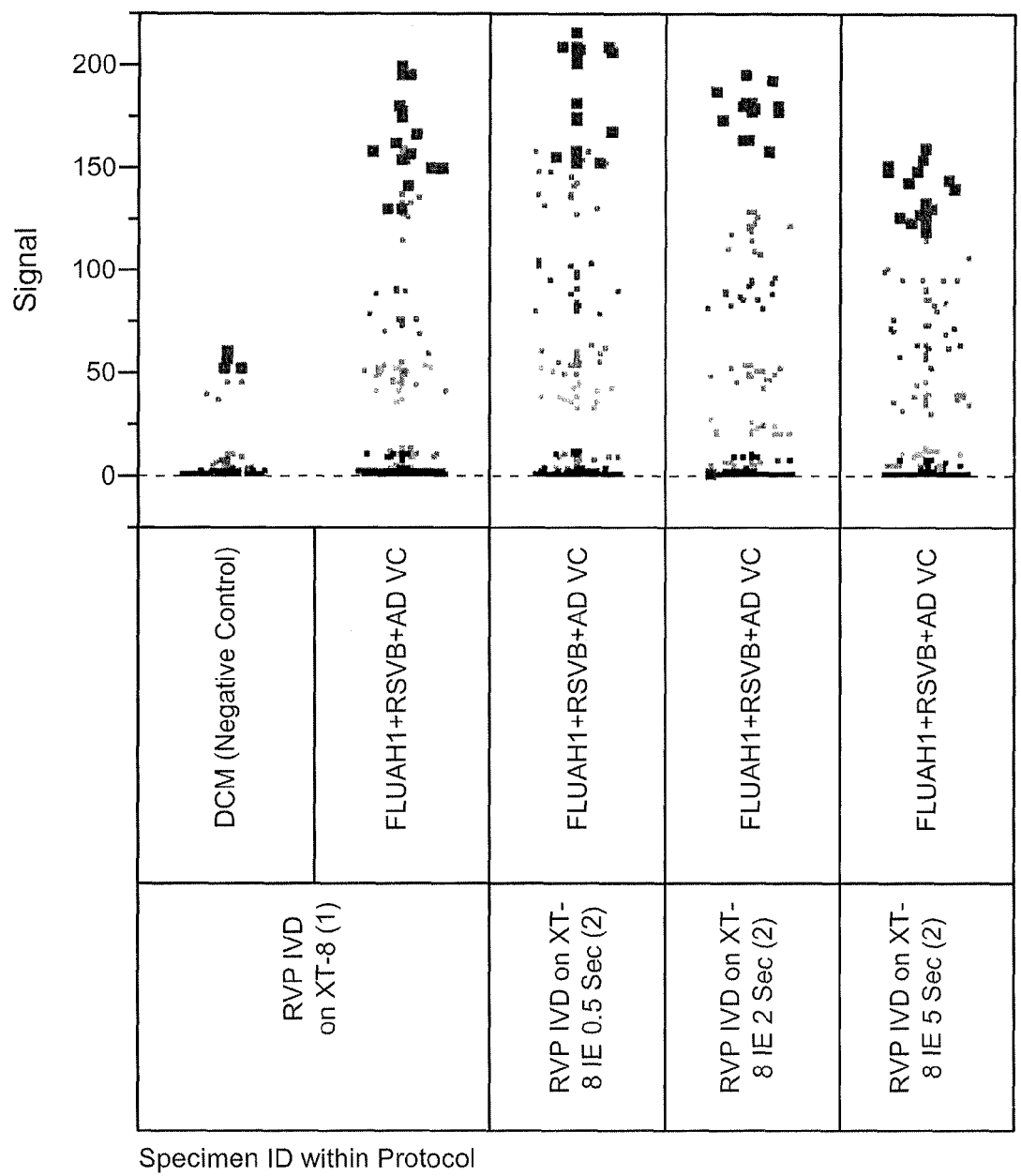
FIG. 10 illustrates signal improvement at different electrode initialization time periods.
Figure 11:
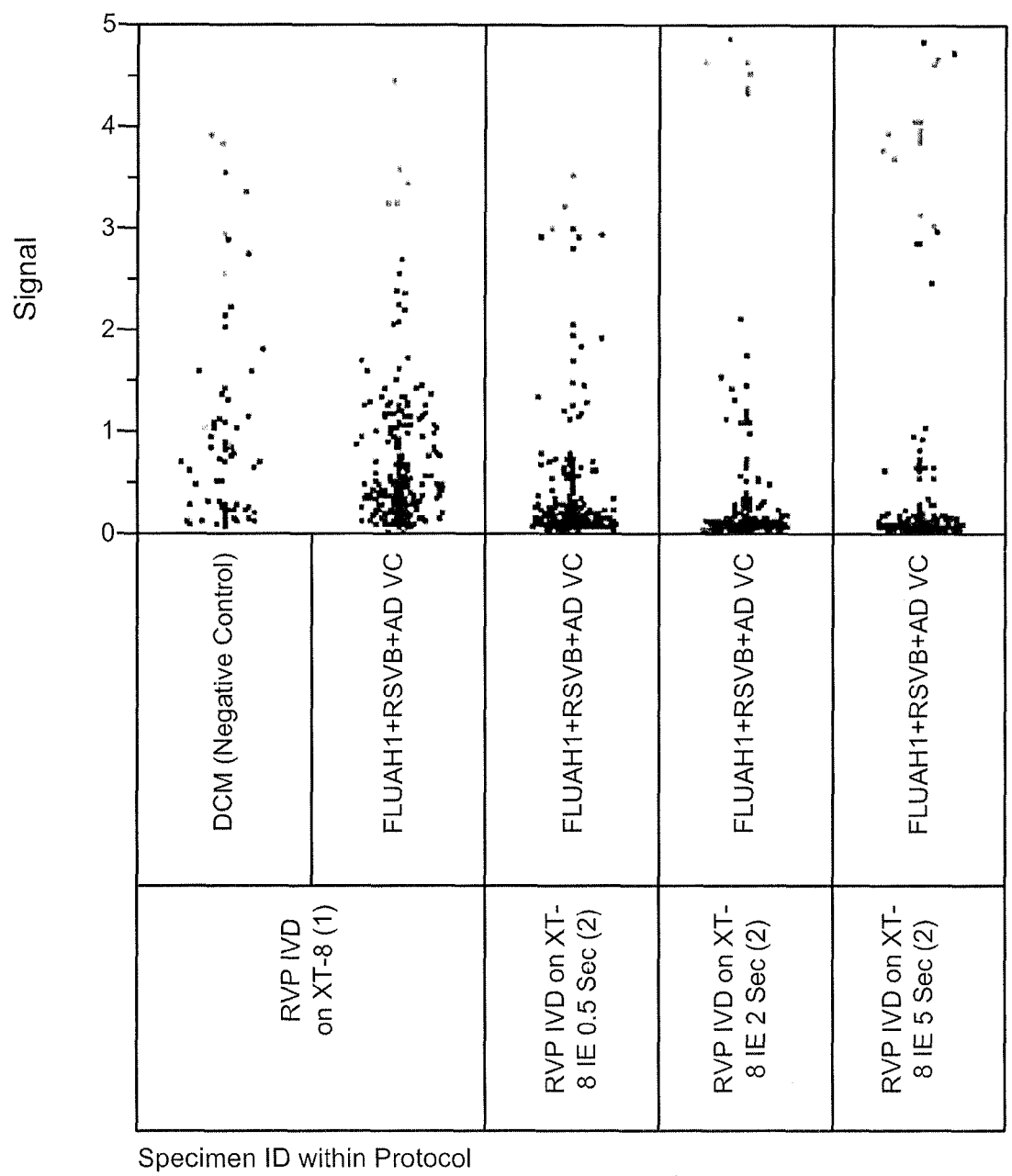
FIG. 11 illustrates noise reduction at different electrode initialization time periods.
Figures 12, 12A:
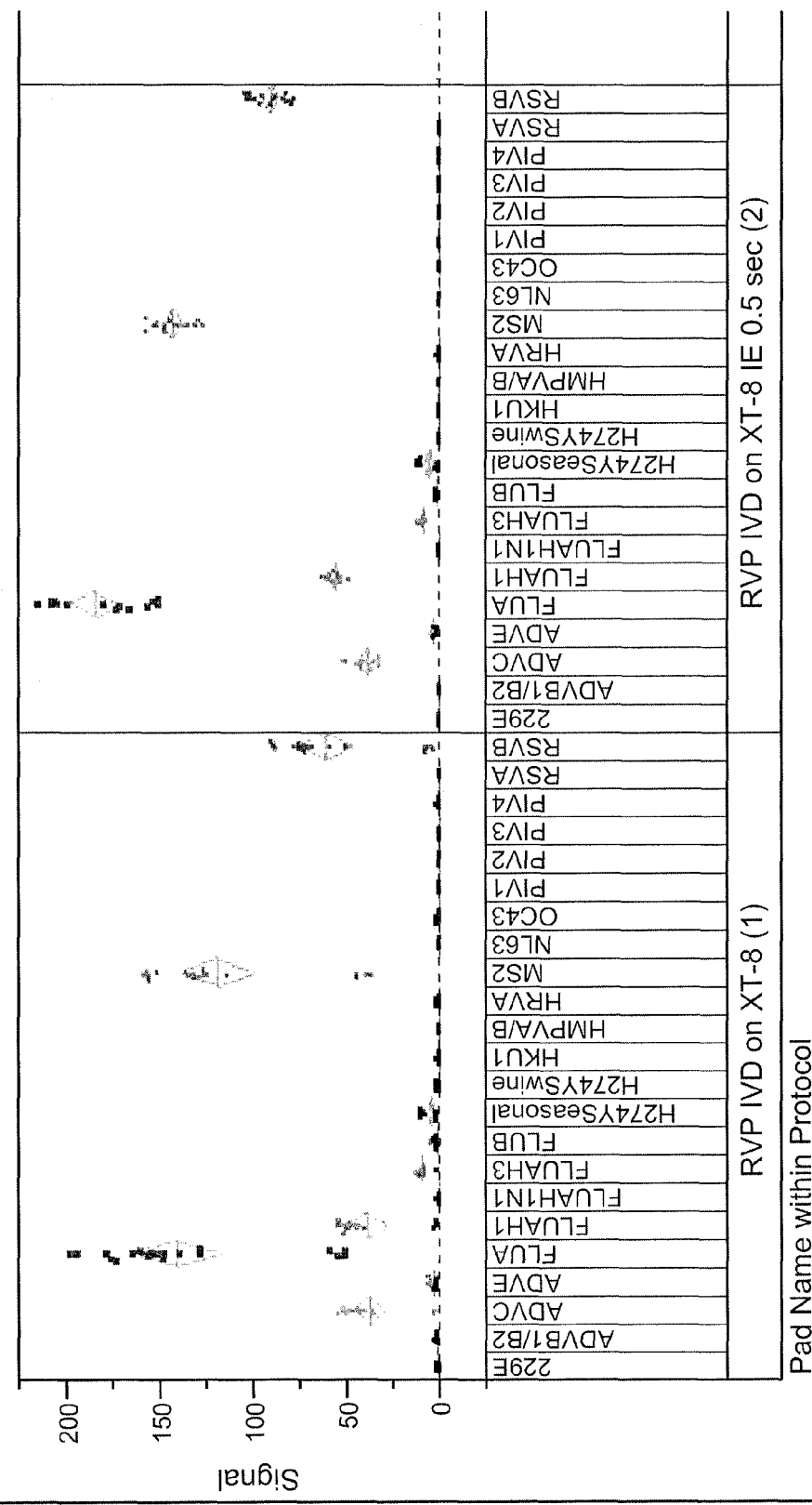
FIG. 12 illustrates signal improvement at different electrode initialization time periods.
Figure 12B:
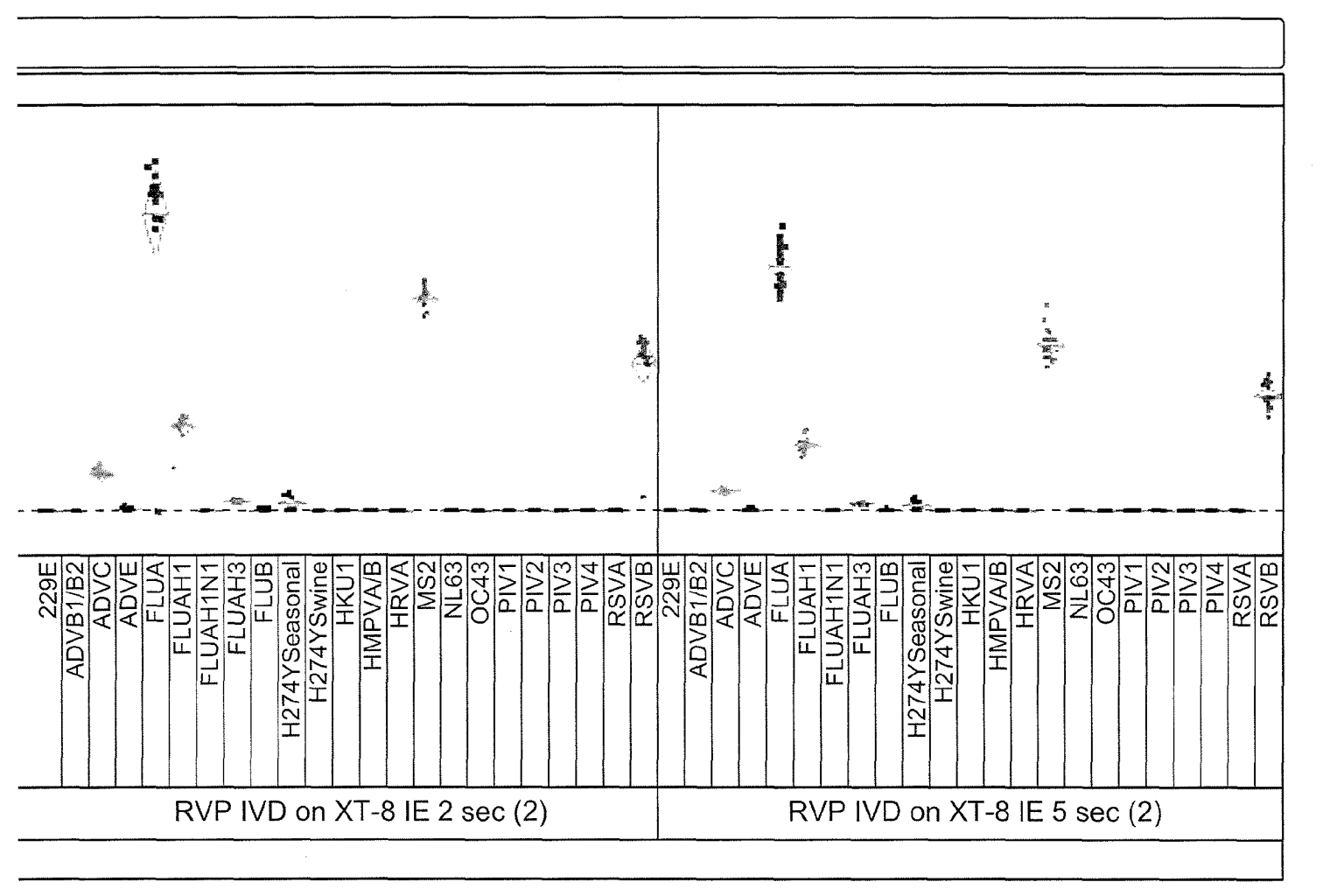
Figure 13B:
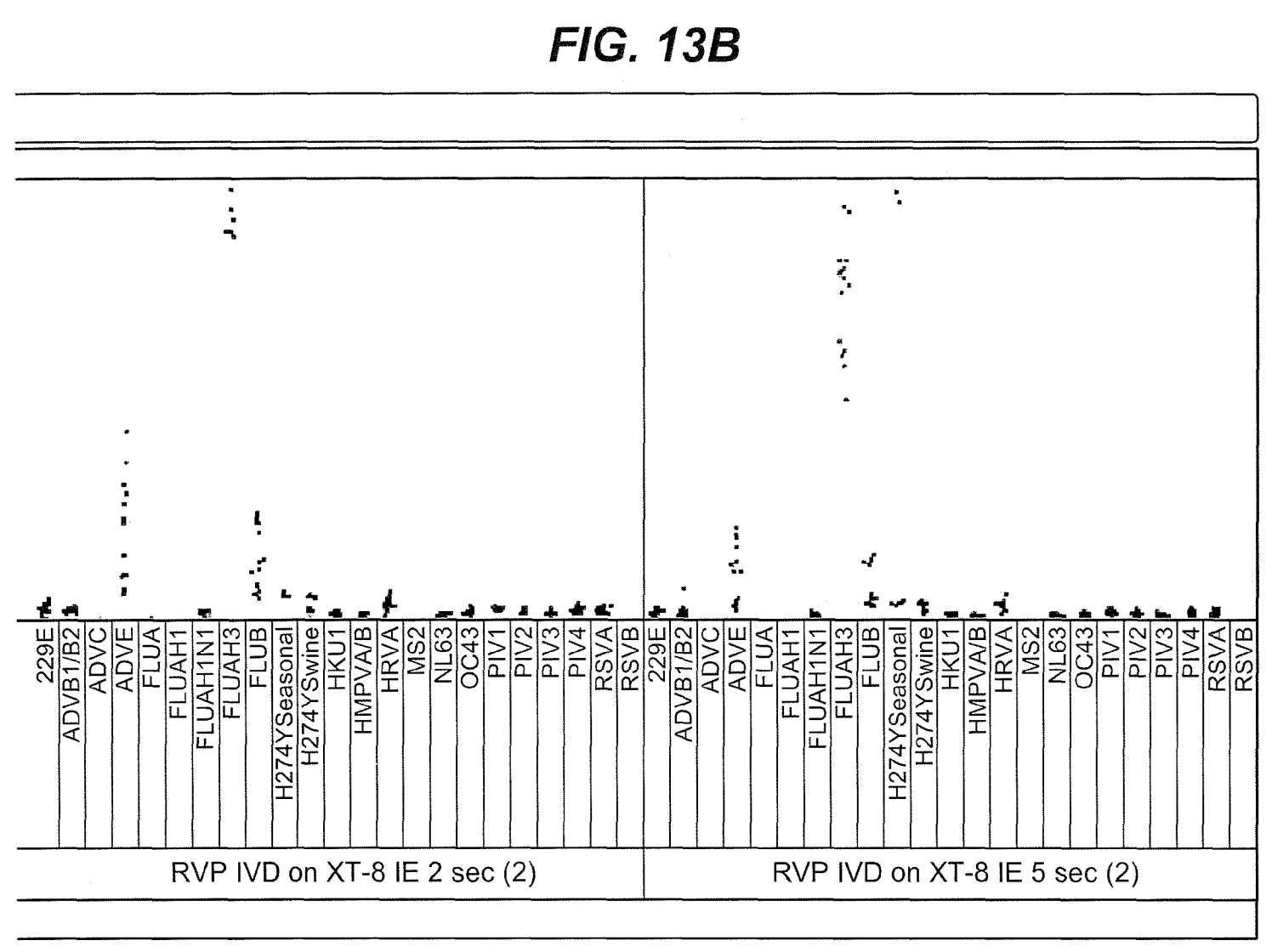

Electrode Initialization (EI) was tested at different initialization time periods using the markers FLUA, MS2, RSVB, FluA H1, and ADVC at 0.5 seconds, 2 seconds, and 5 seconds. FIGS. 10 and 12 show that an initialization scan results in increased signal using the initialization time periods indicated. Furthermore, FIGS. 11 and 13 show that an initialization scan results in decreased noise using each of the initialization time periods indicated.

Figure 14:
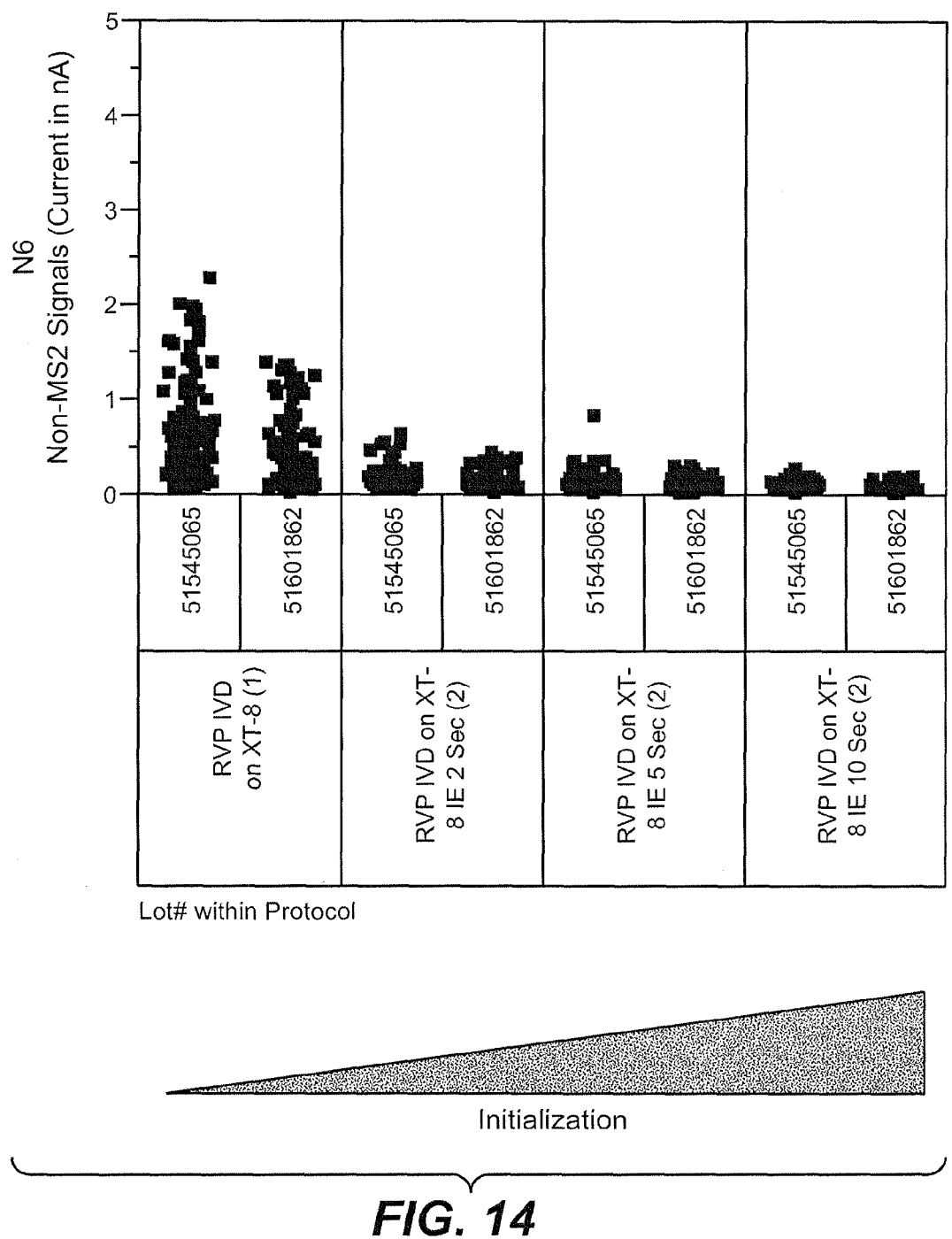
FIG. 14 illustrates reduced background signals at different electrode initialization time periods.
Figure 15:
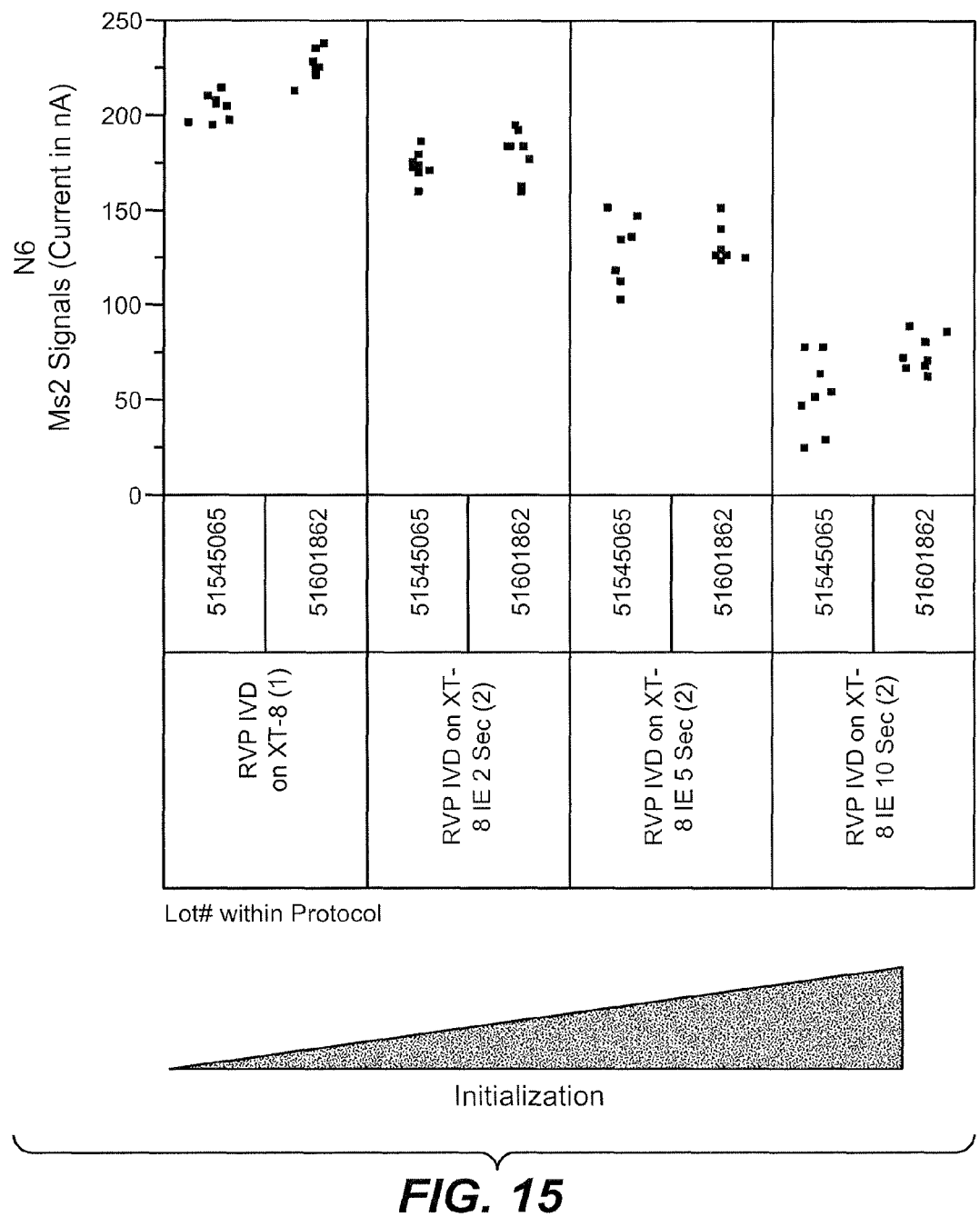
FIG. 15 illustrates reduced MS2 signals at different electrode initialization time periods.

EI was further tested at different initialization time periods was tested. Initialization scans were test at 0, 2, 5, and 10 seconds using MS2 signals as a control. FIG. 14 shows that background signals decreased using EI. FIG. 15 shows that MS2 positive signals decreased slightly with EI. However, FIG. 16 demonstrates that the overall signal to noise ratio increased significantly following an initialization scan.

The example set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

What is claimed is:

1. A method for detecting the presence of a target nucleic acid in a sample, the method comprising:
    a) providing an electrode comprising a monolayer and a capture probe;
    b) initializing the electrode comprising applying an electronic signal completed in 0.5 to 5 seconds to the electrode, said initializing being completed before forming an assay complex comprising said capture probe, said target nucleic acid and a label probe comprising an electron transfer moiety, wherein said initializing comprises a voltage sweep from 150 mV to 750 mV and reduces non-specific binding of free-floating label probes to said electrode;
    c) after said initializing, hybridizing the probe to said target nucleic acid and to said capture probe to form an assay complex; and
    d) electronically detecting the presence or absence of said target nucleic acid in said sample, wherein the detecting provides a higher signal-to-noise ratio than a method wherein no initializing step b) is performed.

2. The method of claim 1 wherein said voltage sweep is done for at least 1.0 seconds.

3. The method of claim 1, wherein the monolayer is a self-assembled monolayer.

4. The method of claim 3, wherein the self-assembled monolayer comprises insulators.

5. The method of claim 3, wherein the self-assembled monolayer comprises conductive oligomers.

6. The method of claim 1, wherein the capture probe further comprises an attachment linker.

7. The method of claim 1, wherein the electron transfer moiety is a metallocene.

8. The method of claim 7, wherein the metallocene is a ferrocene.

9. The method of claim 8, wherein the ferrocene is a ferrocene derivative.

10. The method of claim 1, wherein the electrode is gold.

11. The method of claim 2, wherein electrode initialization is performed for 1 second.

12. The method of claim 2, wherein electrode initialization is performed for 2 seconds.

13. The method of claim 2, wherein electrode initialization is performed for 5 seconds.

14. A method for detecting the presence of a target nucleic acid in a sample, the method comprising:
    a) hybridizing a target nucleic acid and a signal probe;
    b) providing the hybridized target nucleic acid and signal probe to an electrode comprising a monolayer and a capture probe;
    c) applying an electronic signal which is completed in 0.5 to 5 seconds;
    d) after applying the electronic signal, hybridizing the probe and target nucleic acid to the capture probe; and
    e) electronically detecting the presence or absence of said target nucleic acid in said sample.

15. A method for reducing background nonspecific signal in a sample, the method comprising:
    a) hybridizing a target nucleic acid and a signal probe;
    b) providing the hybridized target nucleic acid and signal probe to an electrode comprising a capture probe;
    b) applying an initialization voltage scan which is completed in 0.5 to 5 seconds;
    c) after applying the initialization voltage scan, hybridizing the probe and target nucleic acid to a capture probe; and
    d) applying a second voltage scan to electronically detect the presence or absence of said target nucleic acid in said sample.

16. The method of claim 1, wherein said initializing increases the non-linear harmonic response.

17. The method of claim 1, wherein said initializing reduces the 5th bump in the 4th harmonic signal.

18. The method of claim 1, wherein said electronically detecting is at the third, fourth or fifth harmonics.

19. The method of claim 1, wherein said initializing reduces background nonspecific signal by about 15%.

\* \* \* \* \*